(12) United States Patent
Ji et al.

(10) Patent No.: US 9,738,628 B2
(45) Date of Patent: Aug. 22, 2017

(54) SUBSTITUTED 1H-INDAZOL-1-OL ANALOGS AS INHIBITORS OF BETA CATENIN/TCF PROTEIN-PROTEIN INTERACTIONS

(71) Applicant: University of Utah Research Foundation, Salt Lake City, UT (US)

(72) Inventors: Haitao Ji, Salt Lake City, UT (US); Binxun Yu, Lanzhou (CN); Min Zhang, Salt Lake City, UT (US); Wenxing Guo, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/017,296

(22) Filed: Feb. 5, 2016

(65) Prior Publication Data

US 2016/0297801 A1   Oct. 13, 2016

Related U.S. Application Data

(63) Continuation of application No. 14/377,839, filed as application No. PCT/US2013/025474 on Feb. 10, 2013, now Pat. No. 9,284,299.

(60) Provisional application No. 61/597,640, filed on Feb. 10, 2012.

(51) Int. Cl.
| | |
|---|---|
| C07D 403/06 | (2006.01) |
| C07D 403/12 | (2006.01) |
| C07D 413/06 | (2006.01) |
| C07D 401/14 | (2006.01) |
| C07D 405/06 | (2006.01) |
| C07D 405/14 | (2006.01) |
| C07D 413/14 | (2006.01) |

(52) U.S. Cl.
CPC ......... *C07D 403/06* (2013.01); *C07D 401/14* (2013.01); *C07D 403/12* (2013.01); *C07D 405/06* (2013.01); *C07D 405/14* (2013.01); *C07D 413/06* (2013.01); *C07D 413/14* (2013.01)

(58) Field of Classification Search
CPC .............................. C07D 403/06; C07D 403/12
See application file for complete search history.

(56) References Cited

U.S. PATENT DOCUMENTS

| | | | |
|---|---|---|---|
| 5,039,677 A | 8/1991 | Raeymaekers et al. | |
| 5,298,520 A | 3/1994 | Baker et al. | |
| 6,069,282 A | 5/2000 | Fritz-Langhals et al. | |
| 2006/0042026 A1 | 3/2006 | Glenn et al. | |
| 2010/0256208 A1 | 10/2010 | Gore et al. | |
| 2015/0025114 A1 | 1/2015 | Ji | |

FOREIGN PATENT DOCUMENTS

WO   WO 2013/120045   2/2013

OTHER PUBLICATIONS

Targeted Cancer Therapies, http://www.cancer.gov/aboutcancer/treatment/types/targetedtherapies/targetedtherapiesfactsheet, retrieved Dec. 8, 2015.*
Golub et al, 1999, Science, vol. 531, p. 531-537.*
Thakur, 2013, J. Cell. Mol. Med., vol. 17, No. 4, p. 449-456.*
U.S. Appl. No. 61/597,640, filed Feb. 10, 2012, Ji (University of Utah Research Foundation).
International Search Report and Written Opinion of the International Searching Authority mailed on May 2, 2013 for application PCT/US2013/025474, filed on Feb. 10, 2013 (Applicant—University of Utah Research Foundation) (19 pages).
International Preliminary Report on Patentability mailed on Aug. 21, 2014 for application PCT/US2013/025474, filed on Feb. 10, 2013 (Applicant—University of Utah Research Foundation) (5 pages).
Restriction Requirement issued by the U.S. Patent and Trademark Office on Jun. 30, 2015 for U.S. Appl. No. 14/377,839, filed Aug. 8, 2014 (Inventor—Haitao, et al. // Applicant—University of Utah Research Foundation) (10 pages).
Response filed on Sep. 30, 2015 to Restriction Requirement issued by the U.S. Patent and Trademark Office on Jun. 30, 2015 for U.S. Appl. No. 14/377,839, filed Aug. 8, 2014 (Inventor—Haitao, et al. // Applicant—University of Utah Research Foundation) (16 pages).
Amendment filed on Oct. 13, 2015 for U.S. Appl. No. 14/377,839, filed Aug. 8, 2014 (Inventor—Haitao, et al. // Applicant—University of Utah Research Foundation) (11 pages).
Notice of Allowance issued by the U.S. Patent and Trademark Office on Nov. 12, 2015 for U.S. Appl. No. 14/377,839, filed Aug. 8, 2014 (Inventor—Haitao, et al. // Applicant—University of Utah Research Foundation) (10 pages).

* cited by examiner

Primary Examiner — Rebecca Anderson
Assistant Examiner — Karen Cheng
(74) Attorney, Agent, or Firm — Ballard Spahr LLP

(57) ABSTRACT

In one aspect, the invention relates to substituted 1H-benzo[d][1,2,3]triazol-1-ol analgoues, derivatives thereof, and related compound; synthetic methods for making the compounds; pharmaceutical compositions comprising the compounds; and methods of treating disorders, e.g. various tumors and cancers, associated with β-catenin/Tcf protein-protein interaction dysfunction using the compounds and compositions. This abstract is intended as a scanning tool for purposes of searching in the particular art and is not intended to be limiting of the present invention.

20 Claims, 2 Drawing Sheets

SEQUENCE LISTING

```
<160> NUMBER OF SEQ ID NOS: 6

<210> SEQ ID NO 1
<211> LENGTH: 46
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains biotin)

<400> SEQUENCE: 1

Gly Gly Gly Asp Asp Leu Gly Ala Asn Asp Glu Leu Ile Ser Phe Lys
1               5                   10                  15

Asp Glu Gly Glu Gln Glu Glu Lys Ser Ser Glu Asn Ser Ser Ala Glu
            20                  25                  30

Arg Asp Leu Ala Asp Val Lys Ser Ser Leu Val Asn Glu Lys
        35                  40                  45

<210> SEQ ID NO 2
<211> LENGTH: 46
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains FITC)

<400> SEQUENCE: 2

Gly Gly Gly Asp Asp Leu Gly Ala Asn Asp Glu Leu Ile Ser Phe Lys
1               5                   10                  15

Asp Glu Gly Glu Gln Glu Lys Ser Ser Glu Asn Ser Ser Ala Glu
            20                  25                  30

Arg Asp Leu Ala Asp Val Lys Ser Ser Leu Val Asn Glu Lys
        35                  40                  45

<210> SEQ ID NO 3
<211> LENGTH: 56
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains biotin)

<400> SEQUENCE: 3

Asp Thr Asp Pro Thr Ala Pro Pro Tyr Asp Ser Leu Leu Val Phe Asp
1               5                   10                  15

Tyr Glu Gly Ser Gly Ser Glu Ala Ala Ser Leu Ser Ser Leu Asn Ser
            20                  25                  30

Ser Glu Ser Asp Lys Asp Gln Asp Tyr Asp Tyr Leu Asn Glu Trp Gly
        35                  40                  45

Asn Arg Phe Lys Lys Leu Ala Lys
        50                  55

<210> SEQ ID NO 4
<211> LENGTH: 56
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains FITC)

<400> SEQUENCE: 4

Asp Thr Asp Pro Thr Ala Pro Pro Tyr Asp Ser Leu Leu Val Phe Asp
1               5                   10                  15

Tyr Glu Gly Ser Gly Ser Glu Ala Ala Ser Leu Ser Ser Leu Asn Ser
            20                  25                  30

Ser Glu Ser Asp Lys Asp Gln Asp Tyr Asp Tyr Leu Asn Glu Trp Gly
        35                  40                  45

Asn Arg Phe Lys Lys Leu Ala Lys
        50                  55

<210> SEQ ID NO 5
<211> LENGTH: 44
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains biotin)
```

```
<400> SEQUENCE: 5

Gln Arg Val Gln Val Leu Pro Asp Ala Asp Thr Leu Leu His Phe Ala
1               5                   10                  15

Thr Glu Ser Thr Pro Asp Gly Phe Ser Cys Ser Ser Ser Leu Ser Ala
            20                  25                  30

Leu Ser Leu Asp Glu Pro Phe Ile Gln Lys Asp Lys
        35                  40

<210> SEQ ID NO 6
<211> LENGTH: 44
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: modified N-terminus (contains FITC)

<400> SEQUENCE: 6

Gln Arg Val Gln Val Leu Pro Asp Ala Asp Thr Leu Leu His Phe Ala
1               5                   10                  15

Thr Glu Ser Thr Pro Asp Gly Phe Ser Cys Ser Ser Ser Leu Ser Ala
            20                  25                  30

Leu Ser Leu Asp Glu Pro Phe Ile Gln Lys Asp Lys
        35                  40
```

SUBSTITUTED 1H-INDAZOL-1-OL ANALOGS AS INHIBITORS OF BETA CATENIN/TCF PROTEIN-PROTEIN INTERACTIONS

CROSS-REFERENCE TO RELATED APPLICATIONS

This Application is a Continuation of U.S. application Ser. No. 14/377,839 filed on Aug. 8, 2014, which is a National Phase Application of International Application No. PCT/US2013/025474, filed Feb. 10, 2013, which claims the benefit of U.S. Provisional Application No. 61/597,640, filed on Feb. 10, 2012, which are incorporated herein by reference in their entireties.

REFERENCE TO SEQUENCE LISTING

The Sequence Listing submitted Jun. 27, 2016 as a text file named "21101.0263U3_SL, " created on Jun. 24, 2016, and having a size of 4,118 bytes, is hereby incorporated by reference pursuant to 37 C.F.R. §1.52(e)(5).

BACKGROUND

The canonical Wnt/β-catenin pathway is of particular importance in regulating cell proliferation, differentiation and cell-cell communication. The aberrant activation of Wnt/β-catenin signaling leads to the initiation and progression of many cancers such as colorectal cancers (P. Morin, et al. *Science* 275 (1997) 1787-1790), hepatocellular carcinoma (A., de La Coste, et al. *Proc. Natl. Acad. Sci. U S. A.* 95 (1998) 8847-8851), breast cancers (C. Scheel, E. N. Eaton, S. H. Li, et al. *Cell* 145 (2011) 926-940), leukemia (D. Lu, et al. *Proc. Natl. Acad. Sci. U S. A.* 101 (2004) 3118-3123), and multiple myeloma (K. Sukhdeo, et al. *Proc. Natl. Acad. Sci. U S. A.* 104 (2007) 7516-7521). Moreover, cancer stem cells, which are resistant to conventional chemotherapies and are especially virulent, are controlled by the overactivated Wnt/β-catenin signaling (L. Vermeulen, E. De Sousa, F. Melo, et al. *Nat. Cell Biol.* 2010, 12(5), 468-476; C. Scheel, E. N. Eaton, S. Li, et al. *Cell* 2011, 145(6), 926-940). In addition, dysfunction in the Wnt/β-catenin signaling pathway can lead to fibrotic diseases, e.g. pulmonary fibrosis (W. R. Henderson Jr., et al. *Proc. Natl. Acad. Sci. U S. A.* 107 (2010) 14309-14314), liver fibrosis (J. H. Cheng, et al. *Am. J. Physiol. Gastrointest.Liver Physiol.* 294 (2008) G39-G49) and cystic kidney disease (M. A. Lancaster, et al. *Nat. Med.* 15 (2009) 1046-1054).

β-catenin is the key mediator of the canonical Wnt pathway. It is tightly controlled by a multi-protein destruction complex composed of scaffolding protein Axin, tumor suppressor adenomatous polyposis coli (APC), casein kinase 1 (CK1) and glycogen synthase kinase 3β (GSK3β), which phosphorylates β-catenin and induces its ubiquitination and proteasomal degradation (H. Clevers. *Cell* 127 (2006) 469-480). The inhibition of β-catenin degradation in the pathological conditions, usually through the mutation of genes that encode Axin, APC or the N-terminal phosphorylation sites of β-catenin, results in the stabilization and nuclear translocation of cytoplasmic β-catenin (P. Polakis. *Curr. Opin. Genet. Dev.* 17 (2007) 45-51). In the cell nucleus, β-catenin forms a complex with the N-terminus of T-cell factor (Tcf)/Lymphoid enhancer factor (Lef), and activates the transcription of Wnt target genes, such as c-myc, cyclin D1 and survivin, which lead to the initiation and proliferation of cancer cells, fibrotic cells, and/or the self-renewal of cancer stem cells.

The transcriptional over-activation of Wnt/β-catenin target genes is solely dependent on the formation of nuclear β-catenin/Tcf complex. Thus, selective inhibition of β-catenin/Tcf protein-protein interactions is a potentially appealing therapeutic strategy. Despite significant efforts directed to determination of small-molecule inhibitors of β-catenin/Tcf interactions, little progress had been made to date and only four examples have been reported.

Shivdasani and co-workers screened libraries of synthetic and natural compounds and identified six natural products as the inhibitors of β-catenin/Tcf protein-protein interactions. Three compounds were isolated from fungal organisms, and are planar multi-ring perylenequinones, PKF115-584, CGP049090 and PKF222-815. Three compounds were isolated from the Actinomycete strains, ZTM000990, PKF118-310 and PKF118-744. The $IC_{50}$ values of these compounds in an ELISA-based β-catenin/Tcf interaction assay are between 0.64 and 8.7 µM (M. Lepourcelet, Y. P. Chen, D. S. France, et al. *Cancer Cell* 5 (2004) 91-102). Two compounds, PKF115-584 and CGP049090 (shown in FIG. 1) have been reported to inhibit Tcf reporter activity, block the expression of Wnt target genes and the growth of colon cancer cells. Subsequent studies suggested that these two compounds, PKF115-584 and CGP049090, selectively induced the apoptosis of primary acute myeloid leukemia (AML) (K. S. Minke, P. Staib, A. Puetter, et al. *Eur. J. Haematol.* 82 (2009) 165-175), adrenocortical carcinoma (M. Doghman, J. Cazareth, E. Lalli. *J. Clin. Endocrinol. Metab.* 93 (2008) 3222-3225), B-cell chronic lymphocytic leukemia (CLL) (R. K. Gandhirajan, P. A. Staib, K. Minke, et al. *Neoplasia* 12 (2010) 326-335) and hepatocellular carcinoma (HCC) (W. Wei, M. S. Chua, S. Grepper, et al. *Int. J. Cancer.* 126 (2010) 2426-2436). In the xenograft models of these two compounds, PKF115-584 and CGP049090, suppress the growth of tumors and prolong survival, e.g. xenografts of human multiple myeloma (K. Sukhdeo, M. Mani, Y. Zhang, et al. *Proc. Natl. Acad. Sci. U S. A.* 104 (2007) 7516-7521) and hepatocellular carcinoma (W. Wei, M. S. Chua, S. Grepper, et al. *Int. J. Cancer.* 126 (2010) 2426-2436).

A combination of virtual screening, WaterLOGSY NMR and isothermal titration calorimetry (ITC) studies identified PNU-74654 (shown in FIG. 1; see J. Trosset, C. Dalvit, S. Knapp, et al. *Proteins* 64 (2006) 60-67). The dissociation constant ($K_d$) of this compound with β-catenin is 0.45 µM by ITC. DasGupta and co-workers developed an RNAi-based high-throughput screening method to identify inhibitors of β-catenin-responsive transcription (F. C. Gonsalves, K. Klein, B. B. Carson, et al. *Proc. Natl. Acad. Sci. U S. A.* 108 (2011) 5954-5963), which they used to screen small-molecule libraries. This cell-based assay was designed to identify inhibitors of the Wnt cascade downstream of the multi-protein destruction complex composed of scaffolding protein Axin, tumor suppressor adenomatous polyposis coli (APC), casein kinase 1 (CK1) and glycogen synthase kinase 3β (GSK3β). Three compounds, iCRT3, iCRT5 and iCRT14, were identified in this assay system (shown in FIG. 1). A protein pulldown assay using GST (26 kD)-fused human Tcf4 (residues 1-55, 5.8 kD) and β-catenin revealed that these compounds, iCRT3, iCRT5 and iCRT14, disrupted β-catenin/Tcf interactions, and inhibited the transcription of Wnt target genes and the growth of colon cancer cells.

Recently, An and coworkers identified an organic copper compound, BC21 (NCI-109268; shown in FIG. 1), as an inhibitor of β-catenin/Tcf interaction by virtual screening and a luciferase-based reporter gene assay. The activity of this compound was confirmed by a fluorescence polarization assay using the shorter peptide segment of human Tcf4 (residue 8-30) (W. Tian, X. Han, M. Yan, et al. *Biochemistry* (2012), ASAP. DOI: 10.1021/bi201428h). However, the known inhibitors of β-catenin/Tcf protein-protein interactions discussed above are either not good drug candidates (PKF115-584, CGP049090 and BC21), or possess weak activity (PNU-74654, iCRT3, iCRT5 and iCRT14).

WO 98/42296 discloses purified β-catenin proteins and conventional heterogeneous bioassays, such as ELISA, to screen inhibitors of β-catenin/Tcf interactions. WO 01/19353A2 discloses potential "targetable" pockets that may be responsible for β-catenin/Tcf4 interactions. Also described therein is a in silico screening algorithm and inhibitors were identified by an ELISA screening. WO 02/44378A2 discloses a luciferase reporter gene assay for screening inhibitors of β-catenin/Tcf interaction. WO02/096430A1 discloses cephalosoporin derivatives as possible inhibitors to disrupt β-catenin/Tcf interaction. WO 03/006447A2 discloses PNU-74654 and related compounds identified via a combination of virtual screening, WaterLOGSY NMR and isothermal titration calorimetry (ITC) studies. US 2004/0005313A1 and US 2006/0165699A1 describes the use of microarray technology, Northern blot and RT-PCR analyses of a group of target genes regulated by β-catenin/Tcf complexes, and used this information to identify possible inhibitors. WO 2008/147713A1 discloses debromohymenialdesine (dBHD) and related derivatives as inhibitors of β-catenin/Tcf protein-protein interactions. JP2008/214243A discloses aureothin as an inhibitor of β-catenin/Tcf interaction. WO 2009/097113A2 describes the compounds iCRT3, iCRT5, and iCRT14, as well as related derivative, that were identified through an RNAi-based high-throughput screenings. WO 2010/014043A1 discloses that RUNX3 forms a ternary complex with the β-catenin/Tcf complex and attenuates the Wnt signaling. The phosphorylation of RUNX3 is reported to diminish the formation of the ternary complex, thus increasing Wnt signaling. The inhibition of RUNX3 phosphorylation by inhibitors is a possible therapeutic approach targeting this pathway. U.S. Pat. No. 7,999,089B1 describes RNA aptamers that bind to β-catenin and disrupt the β-catenin/Tcf complex.

Despite advances in research directed to identifying inhibitors the Wnt signaling pathway generally, and specifically inhibitors of β-catenin/Tcf interactions, there remains a scarcity of compounds that are both potent, efficacious, and selective inhibitors of β-catenin/Tcf interactions and also effective in the treatment of cancers and other diseases associated with uncontrolled cellular proliferation, e.g. fibrotic diseases, associated with β-catenin/Tcf dysfunction. These needs and other needs are satisfied by the present invention.

SUMMARY

In accordance with the purpose(s) of the invention, as embodied and broadly described herein, the invention, in one aspect, relates to compounds useful as inhibitors of β-catenin/Tcf protein-protein interactions, methods of making same, pharmaceutical compositions comprising same, and methods of treating disorders, e.g. various tumors and cancers, associated with a β-catenin/Tcf protein-protein interaction dysfunction or a Wnt pathway dysregulation using same.

Disclosed are compounds having a structure represented by a formula:

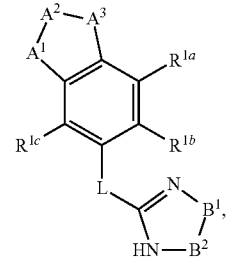

wherein $A^1$ is selected from —N═, —NH—, and —$CR^{2a}$═; wherein $A^2$ is selected from ═N—, (C═O), (C═S), and ═$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N═, —O—, and —S—; wherein $B^2$ is selected from ═N—, (C═O), (S═O), and (C═S); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are compounds having a structure represented by a formula:

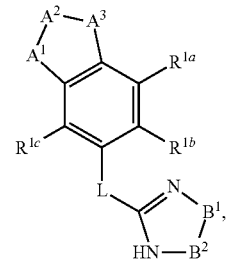

wherein $A^1$ is selected from —N═, —NH—, and —$CR^{2a}$═; wherein $A^2$ is selected from ═N—, (C═O), (C═S), and ═$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N═, —O—, and —S—; wherein $B^2$ is selected from ═N—, (C═O), and (S═O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are compounds having a structure represented by a formula:

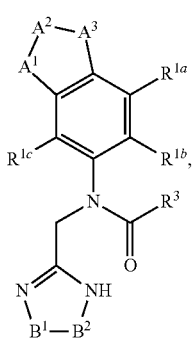

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —$NH_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —$NH_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are compounds having a structure represented by a formula:

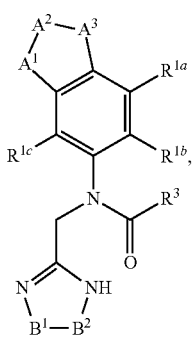

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —$NH_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —$NH_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are pharmaceutical compositions comprising a therapeutically effective amount of a disclosed compound and a pharmaceutically acceptable carrier.

Also disclosed are synthetic methods for making the disclosed compounds. In a further aspect, disclosed are the products of the disclosed synthetic methods.

Also disclosed are methods for the treatment of a disorder associated with a β-catenin/Tcf protein-protein interaction dysfunction in a mammal comprising the step of administering to the mammal a therapeutically effective amount of a disclosed compound, or a pharmaceutically acceptable salt, hydrate, solvate, or polymorph thereof.

Also disclosed are methods for the treatment of a disorder associated with a Wnt pathway dysregulation in a mammal comprising the step of administering to the mammal a therapeutically effective amount of a disclosed compound, or a pharmaceutically acceptable salt, hydrate, solvate, or polymorph thereof.

Also disclosed are method for inhibition of β-catenin/Tcf protein-protein interactions in a mammal comprising the step of administering to the mammal a therapeutically effective amount of least one disclosed compound, or a pharmaceutically acceptable salt, hydrate, solvate, or polymorph thereof.

Also disclosed are method for inhibition of the Wnt pathway in a mammal comprising the step of administering to the mammal a therapeutically effective amount of least one disclosed compound, or a pharmaceutically acceptable salt, hydrate, solvate, or polymorph thereof.

Also disclosed are methods for inhibiting β-catenin/Tcf protein-protein interactions in at least one cell, comprising the step of contacting the at least one cell with an effective amount of least one disclosed compound, or a pharmaceutically acceptable salt, hydrate, solvate, or polymorph thereof.

Also disclosed are methods for inhibiting the Wnt pathway in at least one cell, comprising the step of contacting the at least one cell with an effective amount of least one disclosed compound, or a pharmaceutically acceptable salt, hydrate, solvate, or polymorph thereof.

Also disclosed are uses of a disclosed compound, or a pharmaceutically acceptable salt, hydrate, solvate, or polymorph thereof. In a further aspect, the invention relates to pharmaceutical compositions comprising a pharmaceutically acceptable carrier and an effective amount of a disclosed compound, or a pharmaceutically acceptable salt, hydrate, solvate, or polymorph thereof.

Also disclosed are kits comprising at least one disclosed compound, or a pharmaceutically acceptable salt, hydrate, solvate, or polymorph thereof, and one or more of: (a) at least one agent known to activate the Wnt pathway; (b) at least one agent known to inhibit the Wnt pathway; (c) at least one agent known to treat a disorder of uncontrolled cellular proliferation; or (d) instructions for treating a disorder associated with uncontrolled cellular proliferation.

Also disclosed are methods for manufacturing a medicament comprising combining at least one disclosed compound or at least one disclosed product with a pharmaceutically acceptable carrier or diluent. In a further aspect, the invention relates to the use of a disclosed compound in the manufacture of a medicament for the treatment of a disorder associated with a Wnt pathway dysregulation. In a yet further aspect, the Wnt pathway dysregulation is a β-catenin/Tcf protein-protein interactions dysfunction. In a still further aspect, the invention relates to the use of a disclosed compound in the manufacture of a medicament for the treatment of a disorder of uncontrolled cellular proliferation.

Also disclosed are uses of a disclosed compound or a disclosed product in the manufacture of a medicament for the treatment of a disorder associated with a β-catenin/Tcf protein-protein interactions dysfunction in a mammal.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
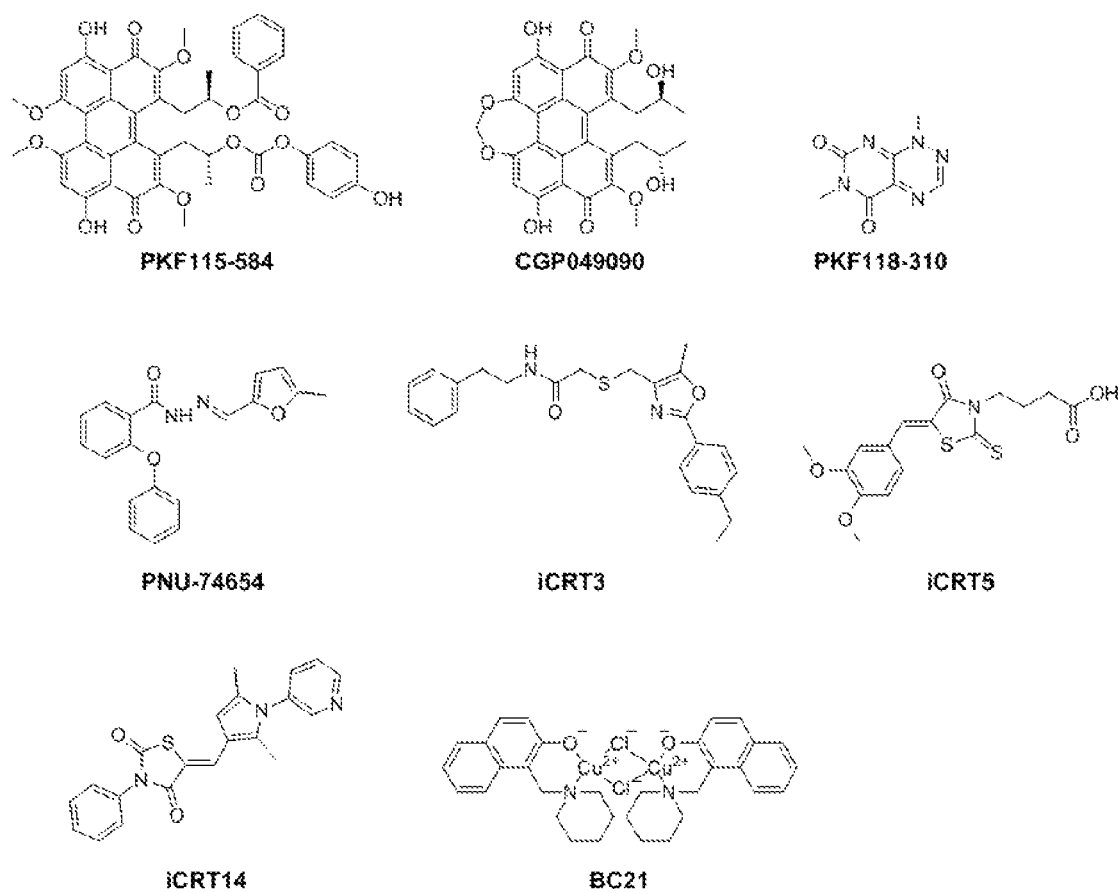
FIG. 1 shows chemical structures of six known β-catenin/Tcf inhibitors, PKF115-584, CGP049090, PNU-74654, iCRT3, iCRT5 and iCRT14.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dode cyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O-A^2O)_a-$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle," as used herein refers to single and multi-cyclic aromatic or non-aromatic ring systems in which at least one of the ring members is other than carbon. Heterocycle includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, brosylate, and halides.

The terms "hydrolysable group" and "hydrolysable moiety" refer to a functional group capable of undergoing hydrolysis, e.g., under basic or acidic conditions. Examples of hydrolysable residues include, without limitatation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

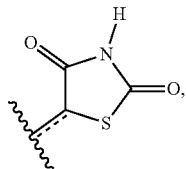

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

It is also appreciated that certain compounds described herein can be present as an equilibrium mixture of tautomers. For example, ketones with an α-hydrogen can exist in an equilibrium mixture of the keto form and the enol form.

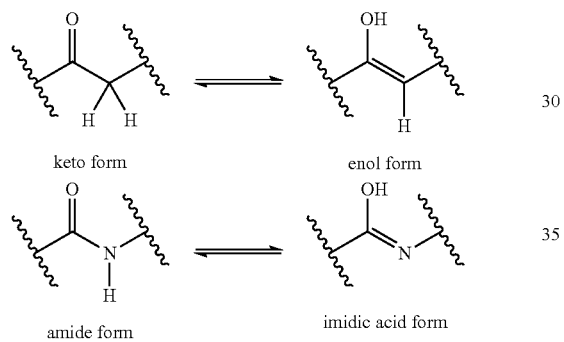

keto form    enol form amide form    imidic acid form

Likewise, amides with an N-hydrogen can exist in an equilibrium mixture of the amide form and the imidic acid form. As another example, tetrazoles can exist in two tautomeric forms, N$^1$-unsubstituted and N$^2$-unsubstituted, as shown below.

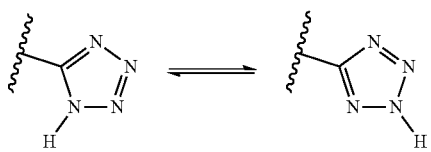 [SMILES: *c1nnn[nH]1 ; *c1nn[nH]n1]

Unless stated to the contrary, the invention includes all such possible tautomers.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

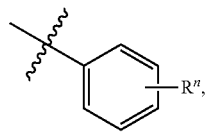

which is understood to be equivalent to a formula:

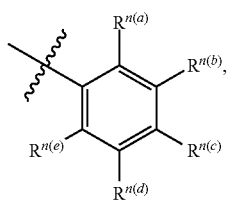

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of β-catenin/Tcf protein-protein interactions, and thus down-regulating Wnt signaling.

In one aspect, the compounds of the invention are useful in the treatment of disorders, e.g. various tumors and cancers, associated with a β-catenin/Tcf protein-protein interaction dysfunction or a Wnt pathway dysregulation using same, and other diseases in which β-catenin/Tcf or the Wnt signaling pathway are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

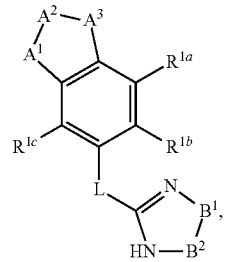

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —NH—, —N(OH)—, —S— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), (S═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In one aspect, the invention relates to a compound having a structure represented by a formula:

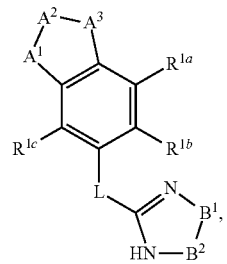

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In one aspect, the invention relates to a compound having a structure represented by a formula:

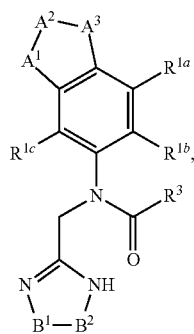

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-Ar$^1$, —(C1-C6)-Ar$^2$, and —(C1-C6)-Cy$^1$; wherein Ar$^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In one aspect, the invention relates to a compound having a structure represented by a formula:

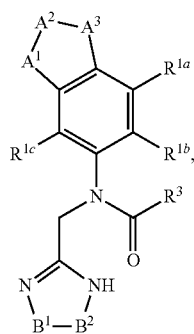

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-Ar$^1$, —(C1-C6)-Ar$^2$, and —(C1-C6)-Cy$^1$; wherein Ar$^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In a further aspect, the compound has a structure represented by a formula listed below:

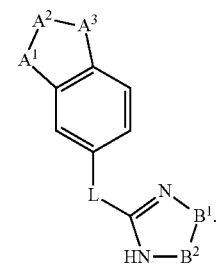

In a further aspect, the compound has a structure represented by a formula listed below:

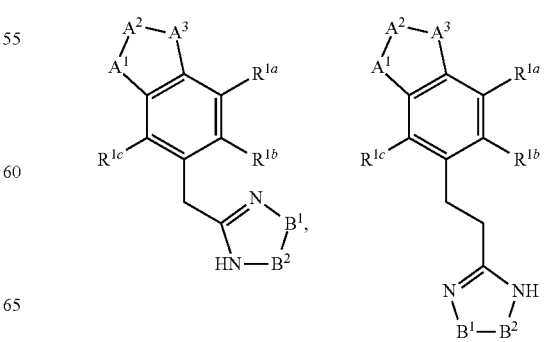

-continued
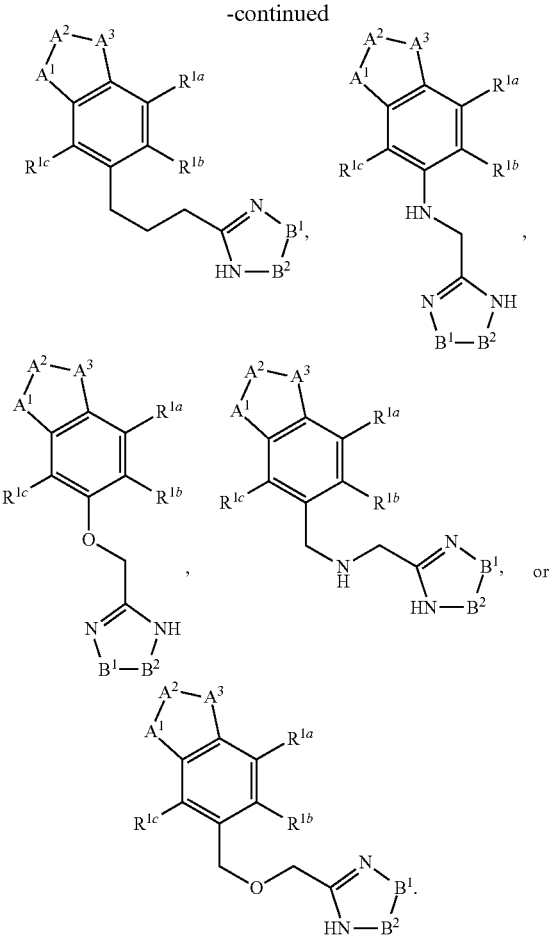
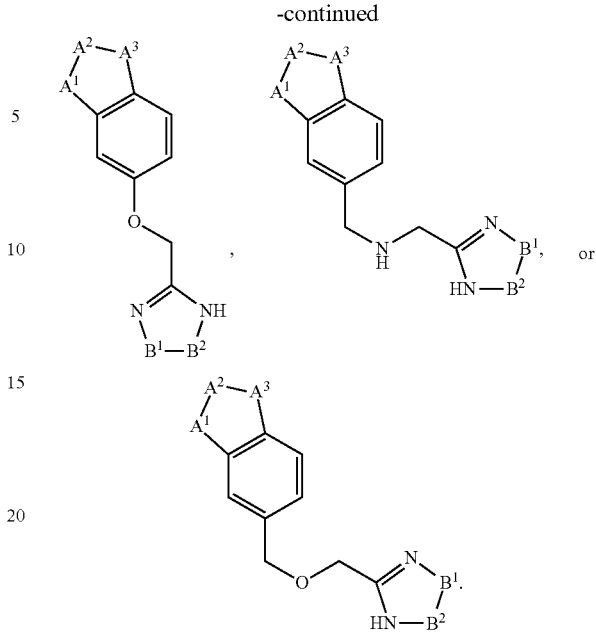
In a further aspect, the compound has a structure represented by a formula listed below:
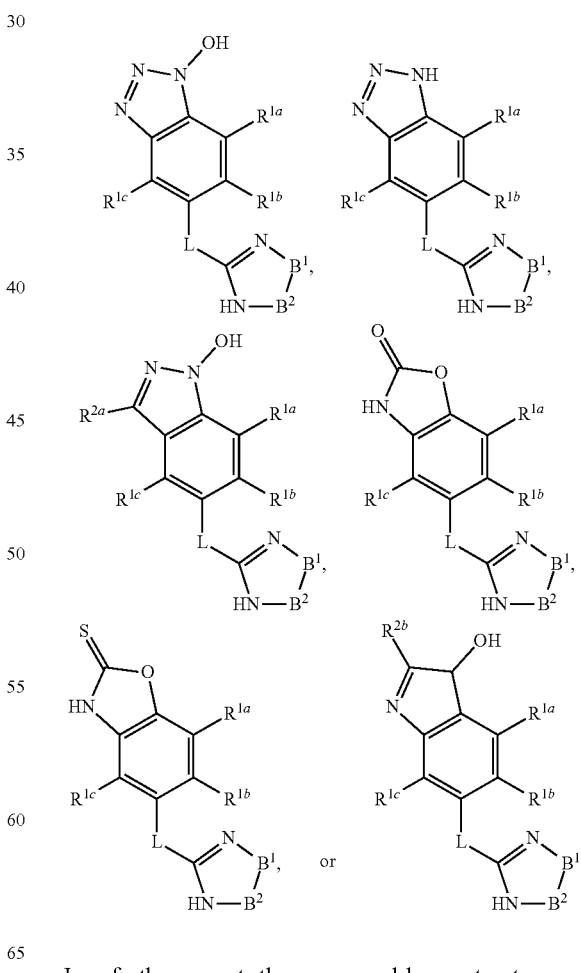
In a further aspect, the compound has a structure represented by a formula listed below:
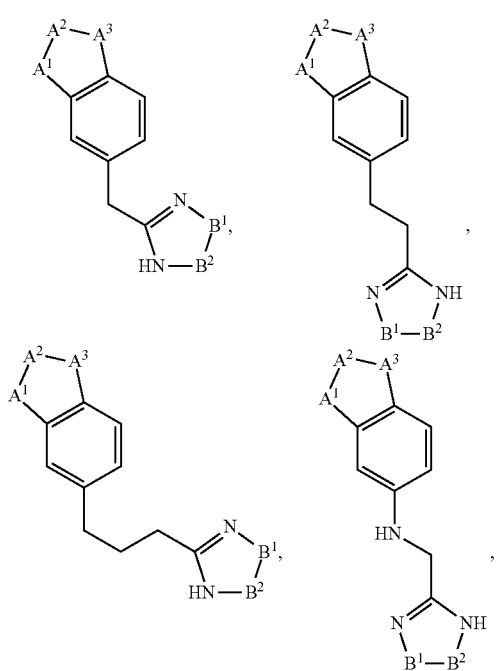
In a further aspect, the compound has a structure represented by a formula listed below:

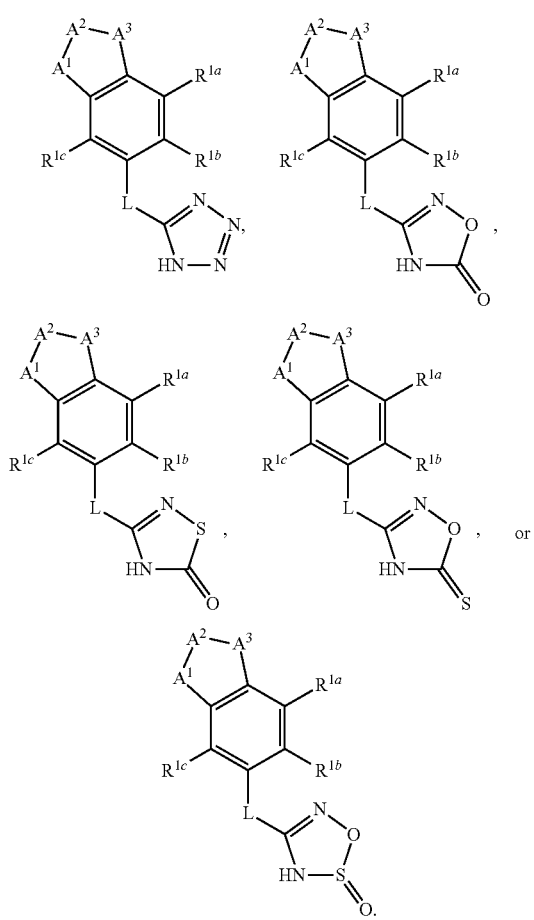
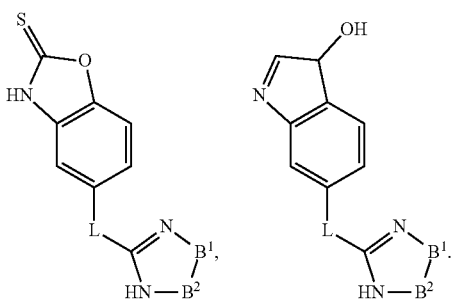
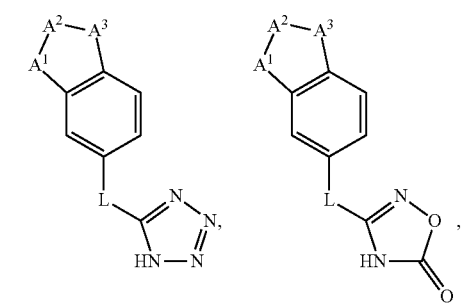
In a further aspect, the compound has a structure represented by a formula listed below:
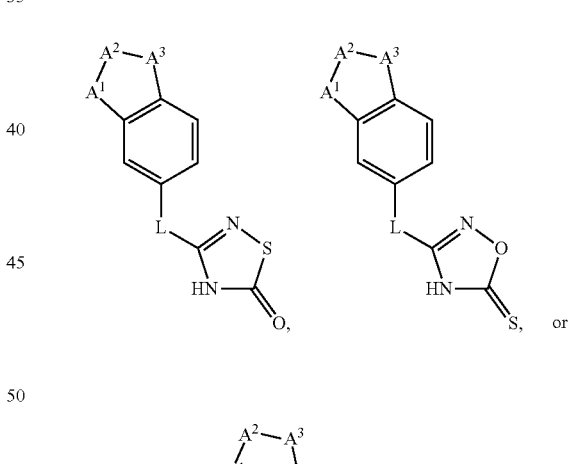
In a further aspect, the compound has a structure represented by a formula listed below:
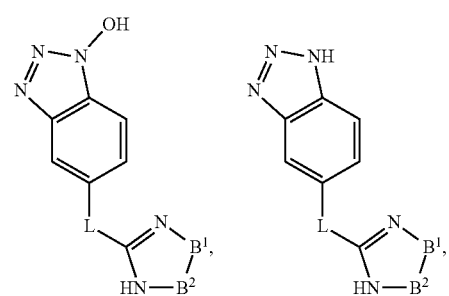
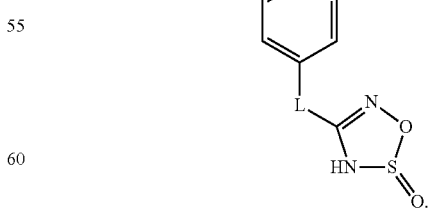
In a further aspect, the compound has a structure represented by a formula listed below:

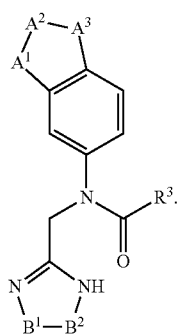
In a further aspect, the compound has a structure represented by a formula listed below:
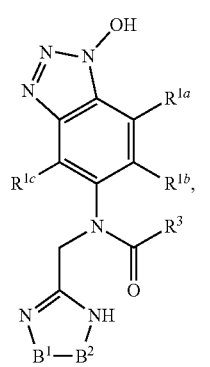 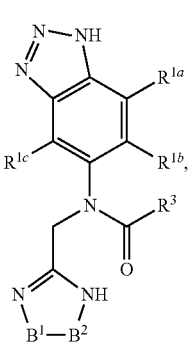
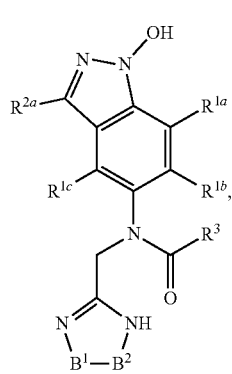 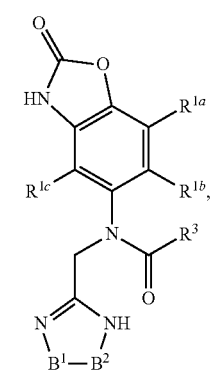
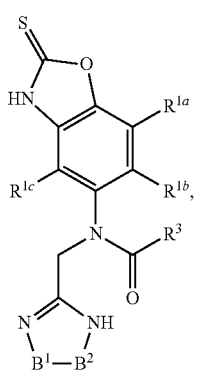 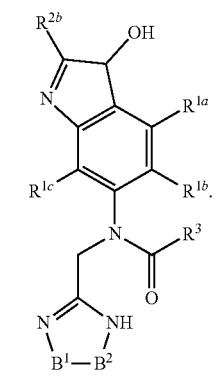
In a further aspect, the compound has a structure represented by a formula listed below:
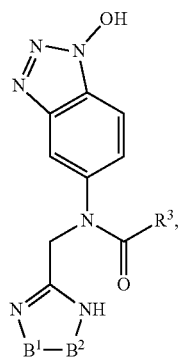 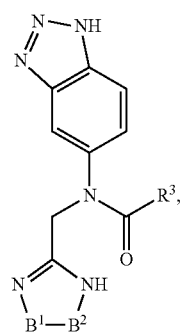
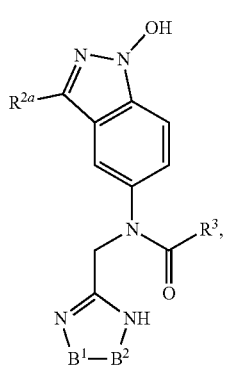 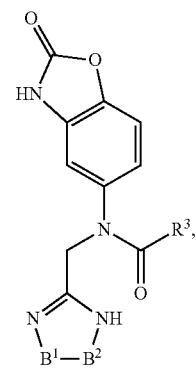
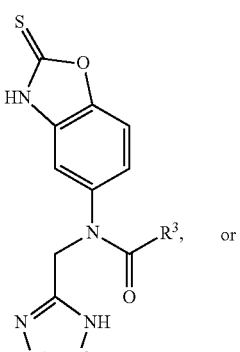 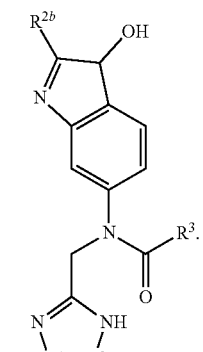
In a further aspect, the compound has a structure represented by a formula listed below:
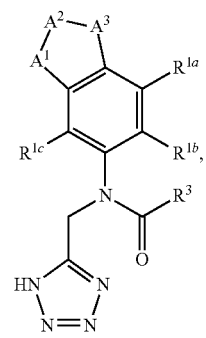 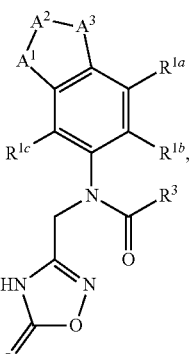

-continued
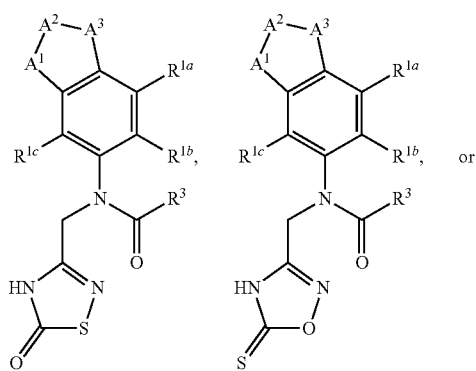
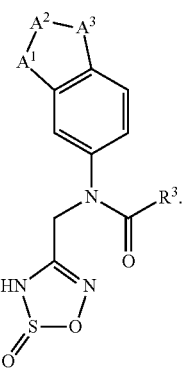 or
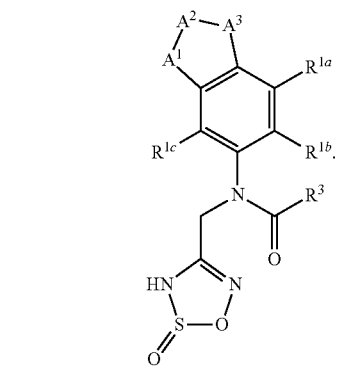
In a further aspect, the compound has a structure represented by a formula listed below:
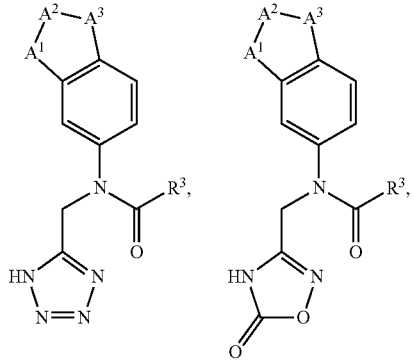
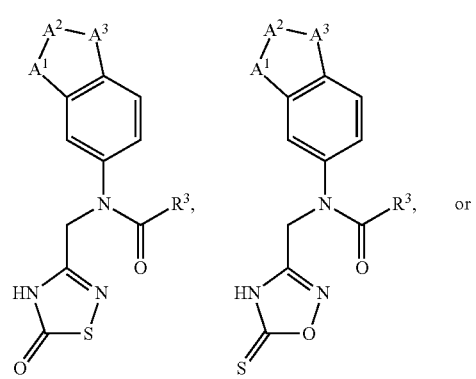
-continued
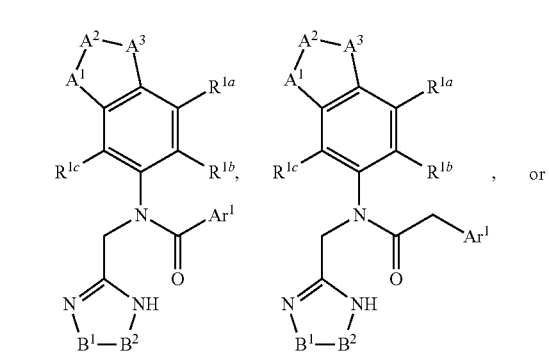
In a further aspect, the compound has a structure represented by a formula listed below:
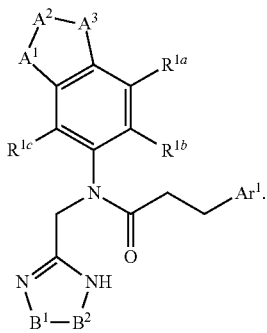
In a further aspect, the compound has a structure represented by a formula listed below:
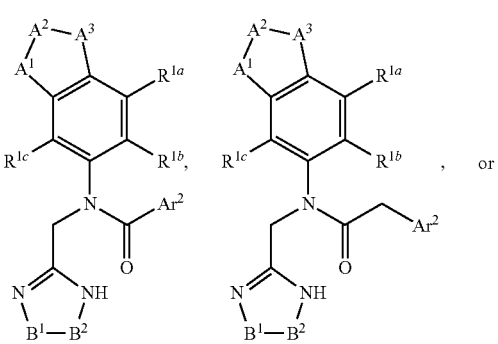

-continued

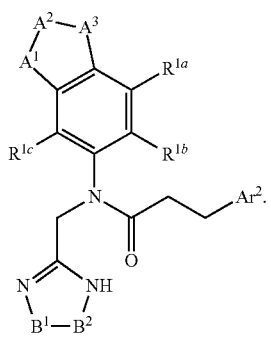

In a further aspect, the compound has a structure represented by a formula listed below:

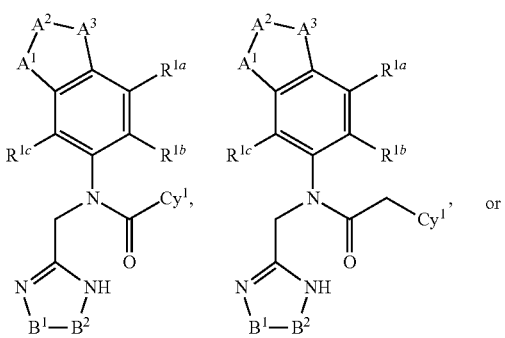

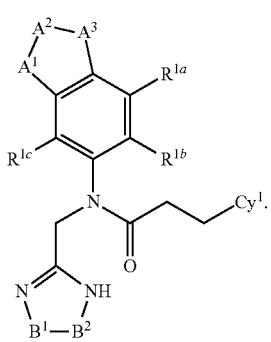

In a further aspect, the compound has a structure represented by a formula listed below:

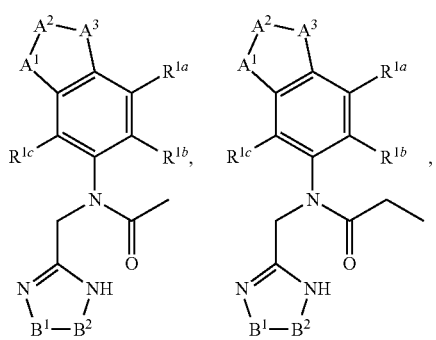

-continued

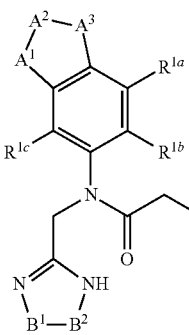, or 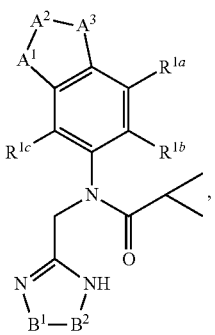,

In a further aspect, the compound has a structure represented by a formula listed below:

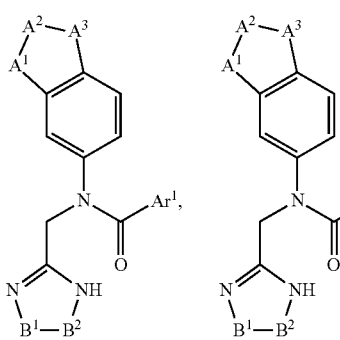

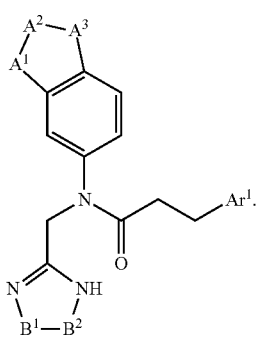

In a further aspect, the compound has a structure represented by a formula listed below:

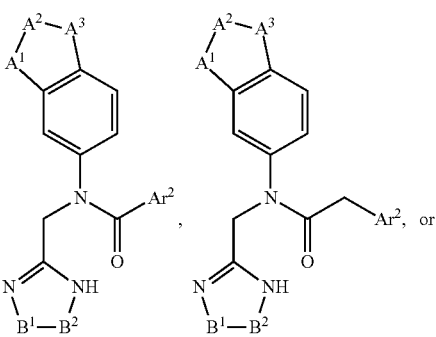

-continued

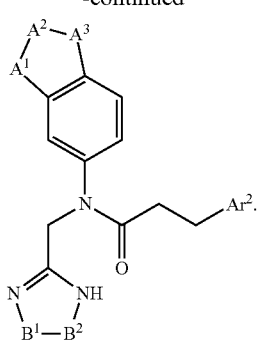

In a further aspect, the compound has a structure represented by a formula listed below:

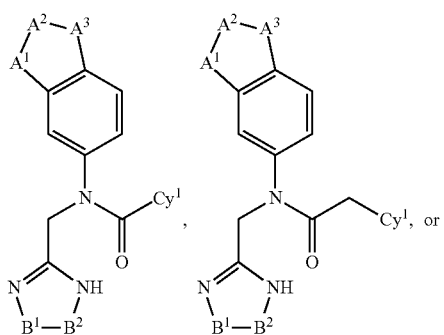

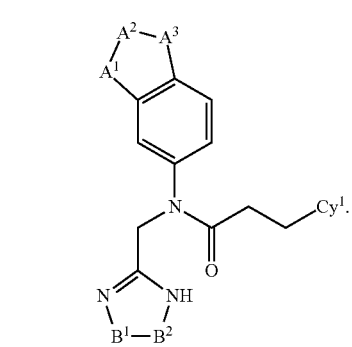

In a further aspect, the compound has a structure represented by a formula listed below:

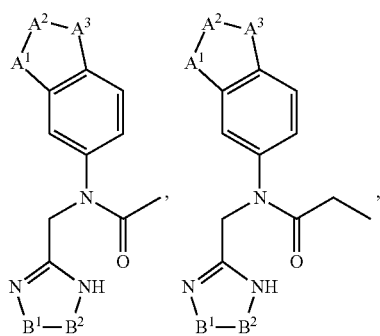

-continued

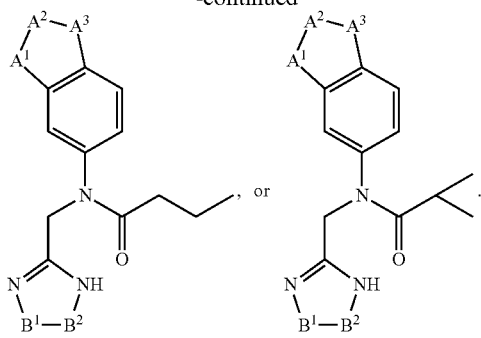

In a further aspect, the compound has a structure represented by a formula listed below:

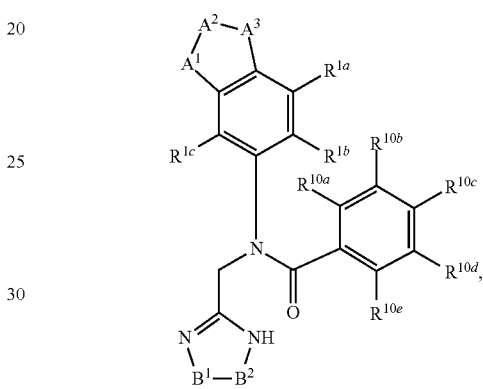

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, the compound has a structure represented by a formula listed below:

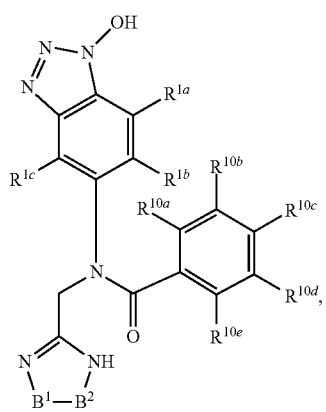

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, the compound has a structure represented by a formula listed below:

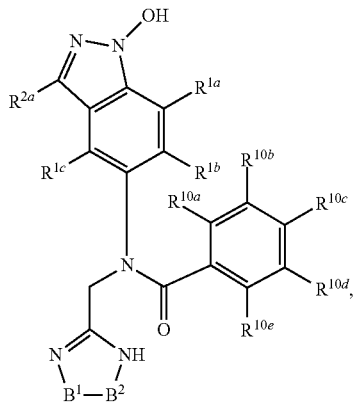

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, the compound has a structure represented by a formula listed below:

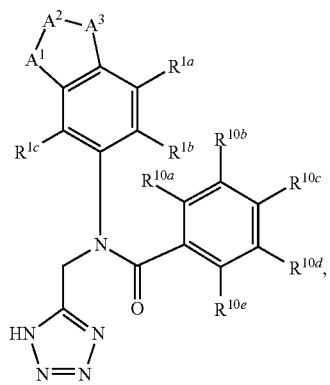

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, the compound has a structure represented by a formula listed below:

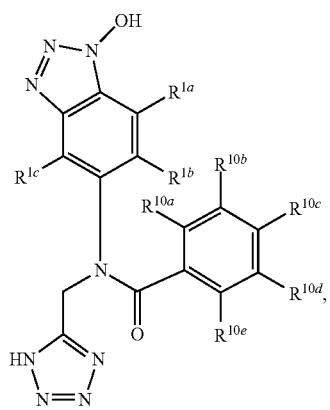

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, the compound has a structure represented by a formula listed below:

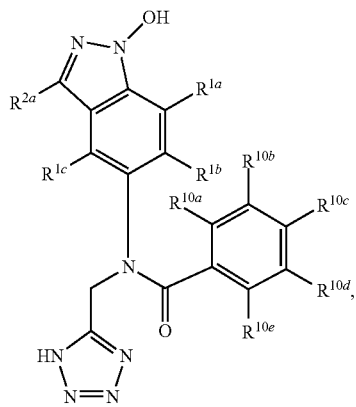

wherein each of $R^{10a}$, $R^{10b}$, $R^{10c}$, $R^{10d}$, and $R^{10e}$ is independently selected from hydrogen, halogen, —OH, —NH$_2$, C1-C3 haloalkyl, C1-C3 polyhaloalkyl, and C1-C3 alkoxy, provided that at least two of $R^{10a}$, $R^{10b}$, $R^{10c}$, $R^{10d}$, and $R^{10e}$ are hydrogen.

In a further aspect, L is selected from —CH$_2$—, —(CH$_2$)$_2$—, —(CH$_2$)$_3$—, —OCH$_2$—, and —CH$_2$OCH$_2$—. In a yet further aspect, L is selected from —CH$_2$—, —(CH$_2$)$_2$—, and —(CH$_2$)$_3$—. In a still further aspect, L is selected from —OCH$_2$— and —CH$_2$OCH$_2$—. In an even further aspect, In a further aspect, L is selected from —NHCH$_2$— and —CH$_2$NHCH$_2$—. In a yet further aspect, L is —CH$_2$—. In a still further aspect, L is —(CH$_2$)$_2$—. In an even further aspect, L is —(CH$_2$)$_3$—. In a yet further aspect, L is —OCH$_2$—. In a still further aspect, L is —NHCH$_2$—. In an even further aspect, L is —CH$_2$NHCH$_2$—. In a still further aspect, L is —CH$_2$OCH$_2$—.

It is appreciated that certain disclosed compounds can be present as an equilibrium mixture of tautomers. For example, in certain aspects, the invention relates to compounds having structures represented by a formula:

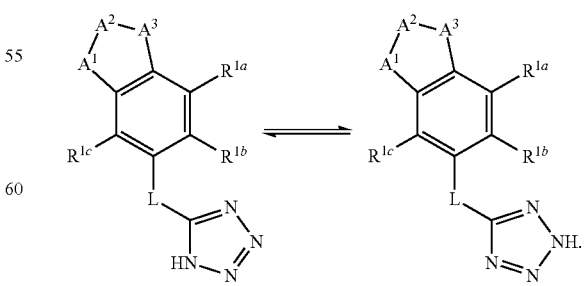

For example, in certain aspects, the invention also relates to compounds having structures represented by a formula:

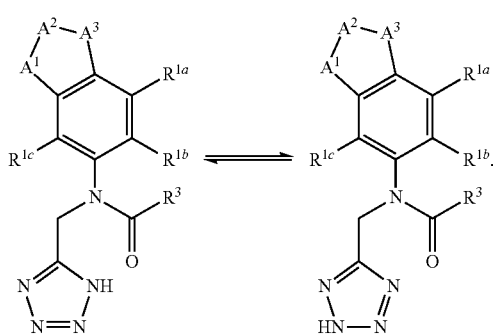
Unless stated to the contrary, the invention includes all such possible tautomers.
2. Example Compounds
In one aspect, a compound can be present as:
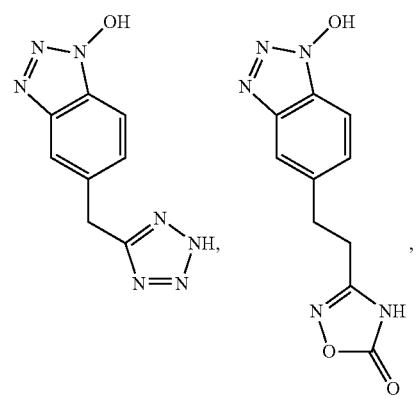
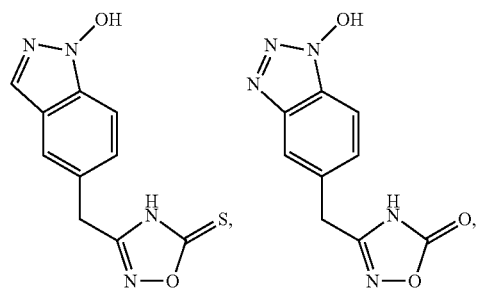
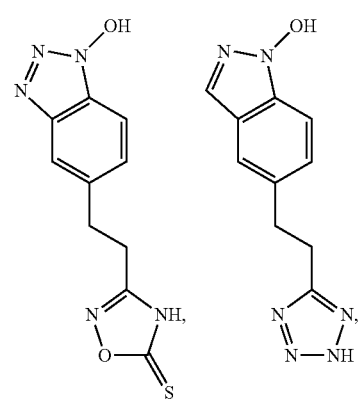
-continued
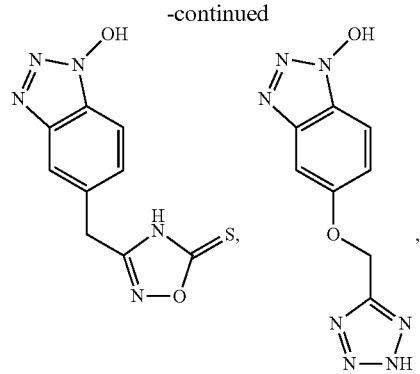
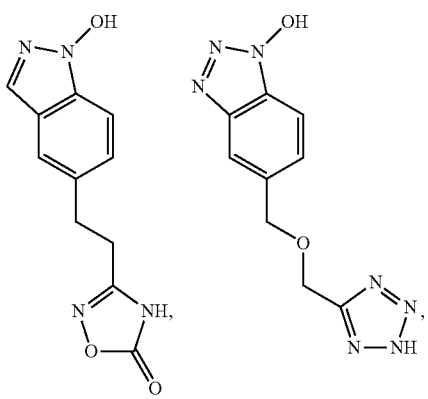
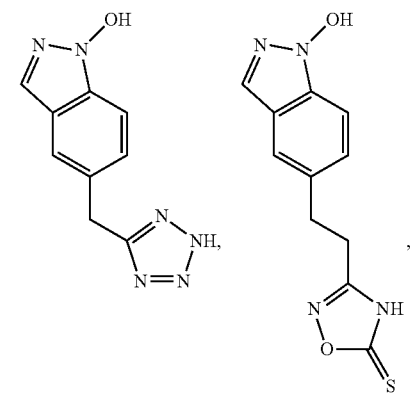
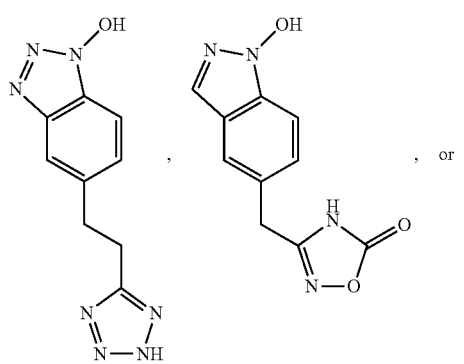

-continued
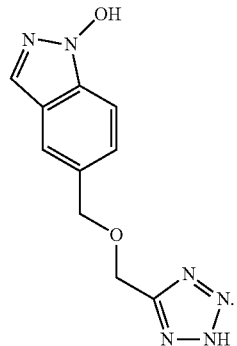
In one aspect, a compound can be present as:
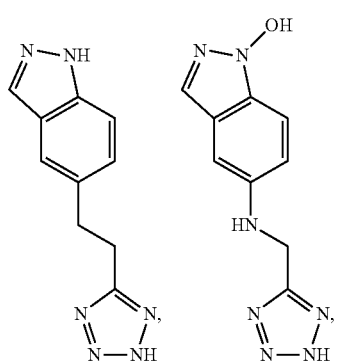
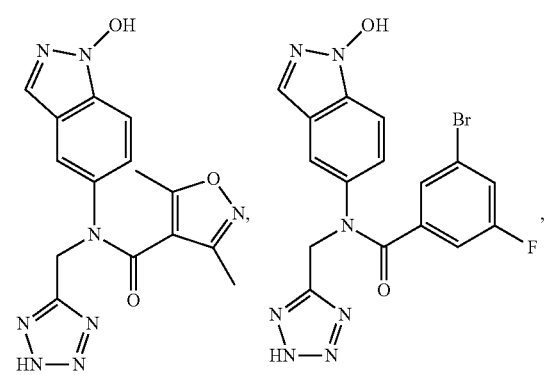
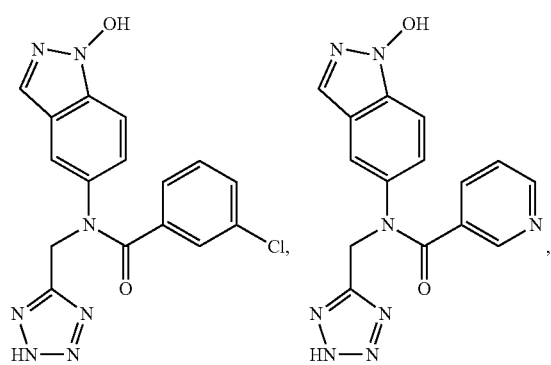
-continued
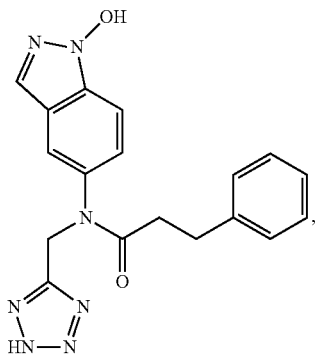
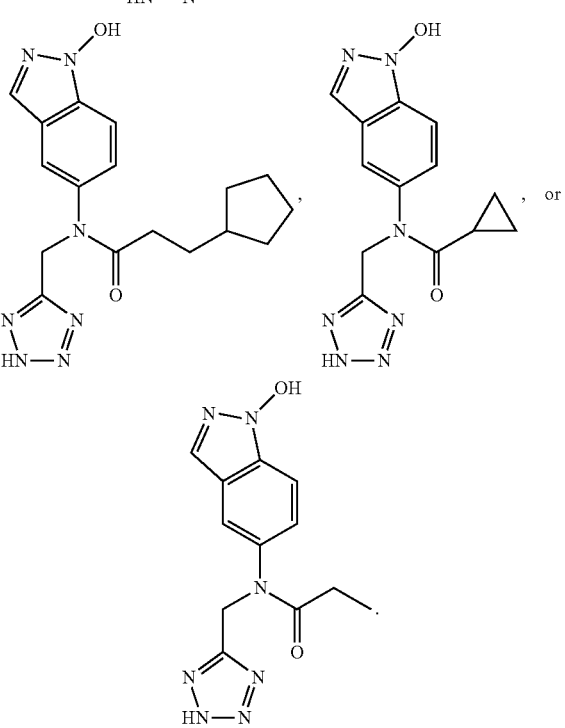
In one aspect, a compound can be present as:
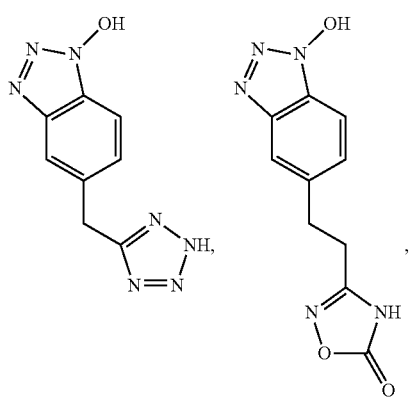

-continued
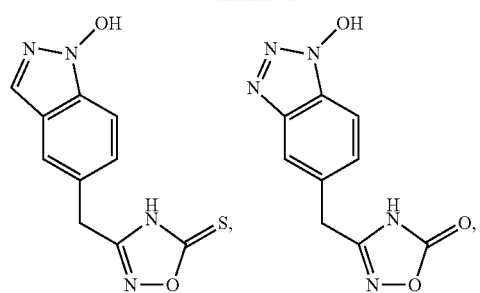

-continued
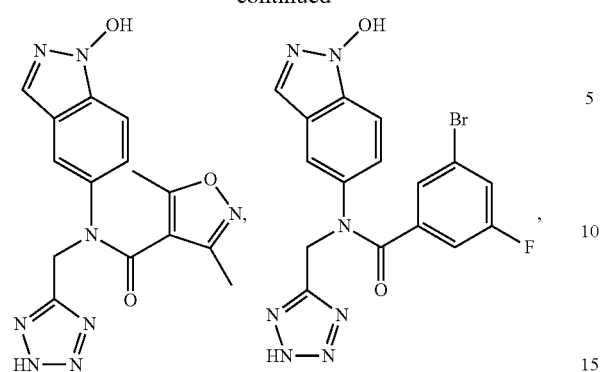
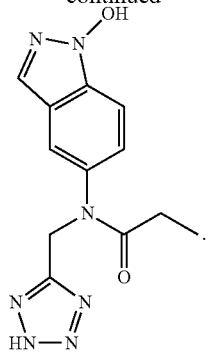
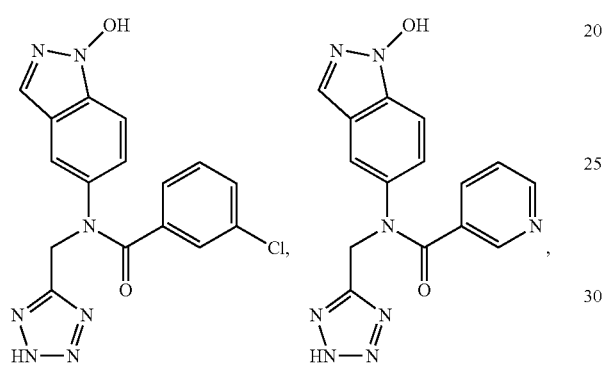
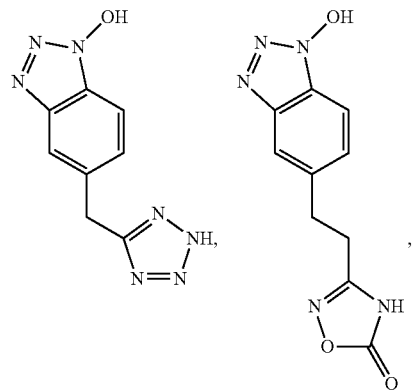
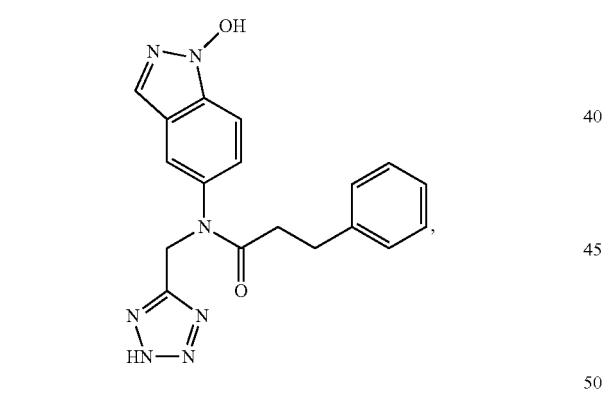
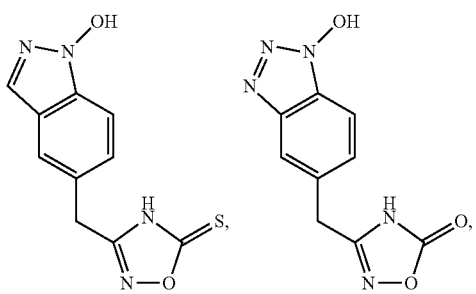
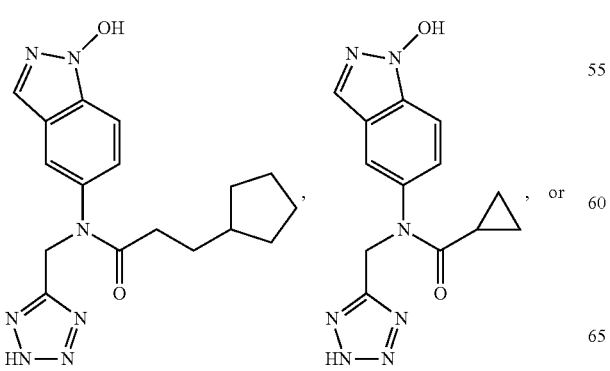
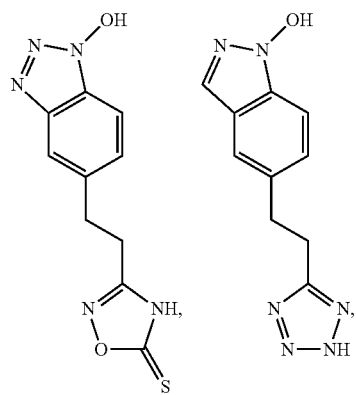
In one aspect, a compound can be present as:

-continued
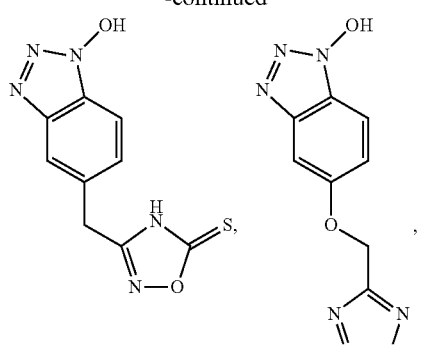
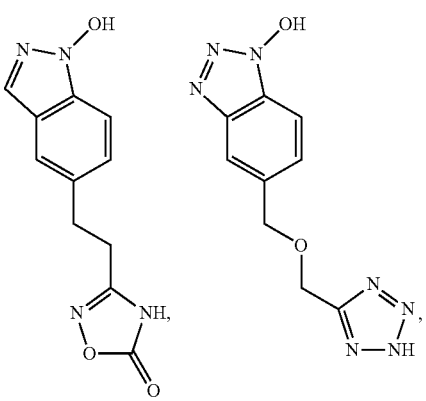
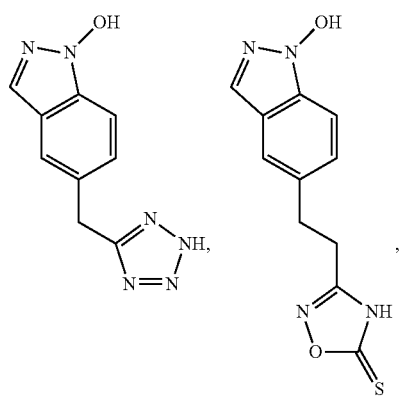
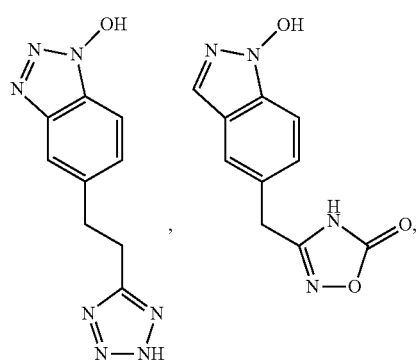
-continued
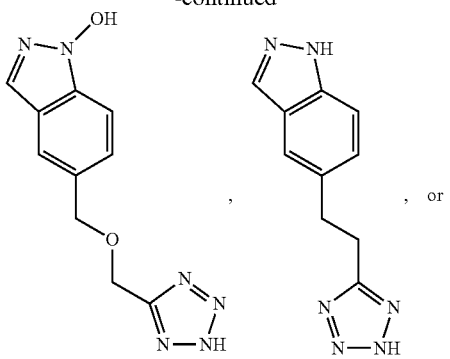
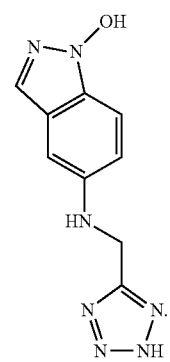 [SMILES: On1ncc2cc(NCc3nn[nH]n3)ccc21]
In one aspect, a compound can be present as:
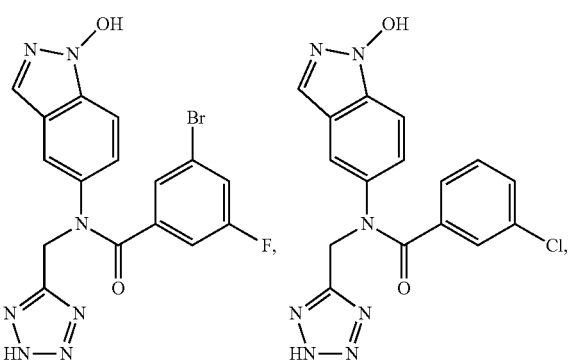
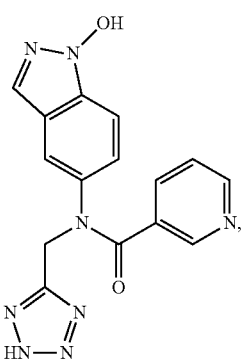

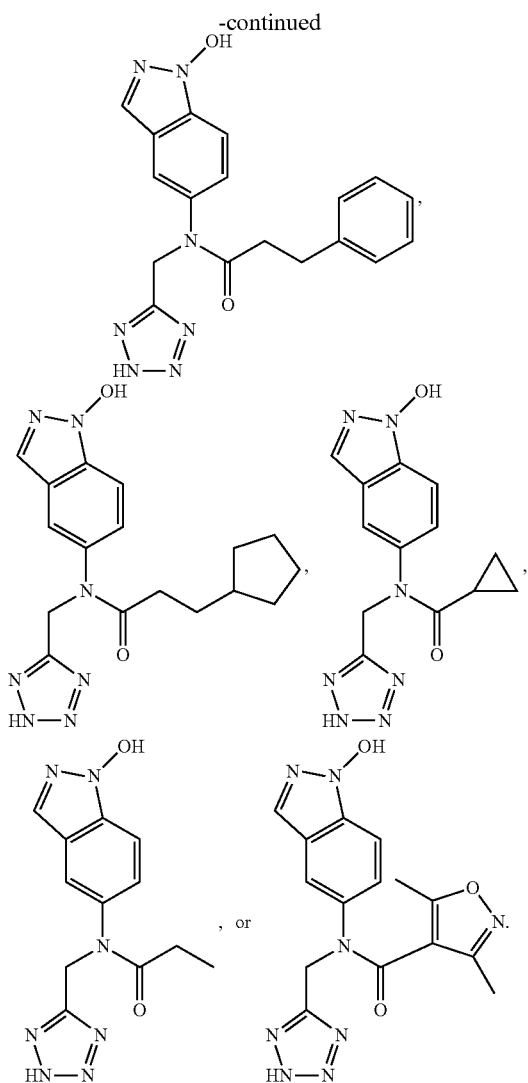

C. Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require inhibition of β-catenin/Tcf protein-protein interactions an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 miligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting β-catenin/Tcf protein-protein interactions (e.g., treatment of one or more disorders of uncontrolled cellular proliferation associated with β-catenin/Tcf protein-protein interaction dysfunction or Wnt dysregulation) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed pharmaceutical compositions can be prepared from the disclosed compounds. It is also understood that the disclosed pharmaceutical compositions can be employed in the disclosed methods of using.

D. Methods of Using the Compounds and Compositions

The pharmaceutical compositions and methods of the present invention can further comprise other therapeutically active compounds as noted herein which are usually applied in the treatment of the above mentioned pathological conditions.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

1. Treatment Methods

The compounds disclosed herein are useful for treating, preventing, ameliorating, controlling or reducing the risk of a variety of disorders wherein the patient or subject would benefit from inhibition or negative modulation of β-catenin/Tcf protein-protein interaction. In one aspect, a treatment can include selective inhibition of β-catenin/Tcf protein-protein interaction to an extent effective to effect down-regulation of Wnt pathway signaling activity. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which β-catenin/Tcf protein-protein interaction inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

In one aspect, provided is a method for treating a disorder of uncontrolled cellular proliferation, comprising: administering to a subject at least one disclosed compound; at least one disclosed pharmaceutical composition; and/or at least one disclosed product in a dosage and amount effective to treat the disorder in the subject. In a further aspect, provided is a method for treating or preventing a disorder characterized by fibrosis, comprising: administering to a subject at least one disclosed compound; at least one disclosed pharmaceutical composition; and/or at least one disclosed product in a dosage and amount effective to treat the disorder in the subject. Also provided is a method for the treatment of a disorder in a mammal comprising the step of administering to the mammal at least one disclosed compound, composition, or medicament.

The invention is directed at the use of described chemical compositions to treat diseases or disorders in patients (preferably human) wherein β-catenin/Tcf protein-protein interaction inhibition would be predicted to have a therapeutic effect, such as disorders of uncontrolled cellular proliferation (e.g. tumors and cancers) and disorders characterized by fibrosis (e.g. polycystic kidney disease), by administering one or more disclosed compounds or products.

The compounds disclosed herein are useful for treating, preventing, ameliorating, controlling or reducing the risk of a variety of disorders of uncontrolled cellular proliferation. In one aspect, the disorder of uncontrolled cellular proliferation is associated with dysregulation of the Wnt signaling pathway. In a further aspect, the Wnt signaling pathway dysregulation is associated with a β-catenin/Tcf protein-protein interaction dysfunction.

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

Examples of disorders associated with β-catenin/Tcf protein-protein interaction dysfunction include a disorder of uncontrolled cellular proliferation. In a yet further aspect, the disorder of uncontrolled cellular proliferation is cancer. In a yet further aspect, the cancer is a myeloma. In an even further aspect, the cancer is colorectal cancer. In a still further aspect, the cancer is breast cancer. In a yet further aspect, the cancer is prostate cancer.

It is understood that cancer refer to or describe the physiological condition in mammals that is typically characterized by unregulated cell growth. The cancer may be multi-drug resistant (MDR) or drug-sensitive. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, cervical cancer, ovarian cancer, peritoneal cancer, liver cancer, e.g., hepatic carcinoma, bladder cancer, colorectal cancer, endometrial carcinoma, kidney cancer, and thyroid cancer.

In various aspects, further examples of cancers are basal cell carcinoma, biliary tract cancer; bone cancer; brain and CNS cancer; choriocarcinoma; connective tissue cancer;

esophageal cancer; eye cancer; cancer of the head and neck; gastric cancer; intra-epithelial neoplasm; larynx cancer; lymphoma including Hodgkin's and Non-Hodgkin's lymphoma; melanoma; myeloma; neuroblastoma; oral cavity cancer (e.g., lip, tongue, mouth, and pharynx); retinoblastoma; rhabdomyosarcoma; rectal cancer; cancer of the respiratory system; sarcoma; skin cancer; stomach cancer; testicular cancer; uterine cancer; cancer of the urinary system, as well as other carcinomas and sarcomas In a further aspect, the cancer is a hematological cancer. In a still further aspect, the hematological cancer is selected from acute myeloid leukemia (AML), acute lymphoblastic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), Hodgkin lymphoma, Non-Hodgkin lymphoma, multiple myeloma, solitary myeloma, localized myeloma, and extramedullary myeloma. In a still further aspect, the cancer is selected from chronic lymphocytic leukemia, small lymphocytic lymphoma, B-cell non-Hodgkin lymphoma, and large B-cell lymphoma.

In a further aspect, the cancer is a cancer of the brain. In a still further aspect, the cancer of the brain is selected from a glioma, medulloblastoma, primitive neuroectodermal tumor (PNET), acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor. In a yet further aspect, the glioma is selected from ependymoma, astrocytoma, oligodendroglioma, and oligoastrocytoma. In an even further aspect, the glioma is selected from juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, multifocal gliomatous tumor, multicentric glioblastoma multiforme tumor, paraganglioma, and ganglioglioma.

In one aspect, the cancer can be a cancer selected from cancers of the blood, brain, genitourinary tract, gastrointestinal tract, colon, rectum, breast, kidney, lymphatic system, stomach, lung, pancreas, and skin. In a further aspect, the cancer is selected from prostate cancer, glioblastoma multiforme, endometrial cancer, breast cancer, and colon cancer. In a further aspect, the cancer is selected from a cancer of the breast, ovary, prostate, head, neck, and kidney. In a still further aspect, the cancer is selected from cancers of the blood, brain, genitourinary tract, gastrointestinal tract, colon, rectum, breast, livery, kidney, lymphatic system, stomach, lung, pancreas, and skin. In a yet further aspect, the cancer is selected from a cancer of the lung and liver. In an even further aspect, the cancer is selected from a cancer of the breast, ovary, testes and prostate In a still further aspect, the cancer is a cancer of the breast. In a yet further aspect, the cancer is a cancer of the ovary. In an even further aspect, the cancer is a cancer of the prostate. In a still further aspect, the cancer is a cancer of the testes.

In various aspects, disorders associated with a β-catenin/Tcf protein-protein interaction dysfunction include disorders characterized by fibrosis. In a further aspect, the fibrotic disease is selected from pulmonary fibrosis, liver fibrosis, and polycystic kidney disease.

The compounds are further useful in a method for the prevention, treatment, control, amelioration, or reducation of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a β-catenin/Tcf protein-protein interaction inhibitor for improving treatment outcomes in the context of disorders of uncontrolled cellular proliferation, including cancer. That is, in one aspect, the invention relates to a cotherapeutic method comprising the step of administering to a mammal an effective amount and dosage of at least one compound of the invention in connection with cancer therapy.

In a further aspect, adminstration improves treatment outcomes in the context of cancer therapy. Adminstration in connection with cancer therapy can be continuous or intermittent. Adminstration need not be simultaneous with therapy and can be before, during, and/or after therapy. For example, cancer therapy can be provided within 1, 2, 3, 4, 5, 6, 7 days before or after administration of the compound. As a further example, cancer therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-cancer therapeutic agents. In a further aspect, the anti-cancer therapeutic agent is selected from 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphaIfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®.

In another aspect, the subject compounds can be administered in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphaIfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™ Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In another aspect, the subject compound can be used in combination with 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone AcetateDexamethasone Sodium PhosphateDexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, *Erwinia* L-asparaginase, Estramustine, EthyolEtopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, GemzarGleevec™, Gliadel R Wafer, GM-CSF, Goserelin, Granulocyte-Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab TiuxetanIdamycin®, Idarubicin, Ifex®, IFN-alphalfosfamide, IL-11IL-2Imatinib mesylate, Imidazole CarboxamideInterferon alfa, Interferon Alfa-2b (PEG Conjugate), Interleukin-2, Interleukin-11, Intron A® (interferon alfa-2b) Iressa®, Irinotecan, Isotretinoin, Ixabepilone, Ixempra™, K, Kidrolase (t), L, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, M, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, MustineMutamycin®, Myleran®, Mylocel™, Mylotarg®, N, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, O, Octreotide, Octreotide acetate, Ofatumumab, Oncospar®, Oncovin®, Ontak®, Onxal™, Oprelvekin, Orapred®, Orasone®, Oxaliplatin, P, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, R, Raloxifene, Revlimid®, Rheumatrex®, Rituxan®, Rituximab, Roferon-A® (Interferon Alfa-2a) Romiplostim, Rubex®, Rubidomycin hydrochloride, S, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, T, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, V, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, X, Xeloda®, Z, Zanosar®, Zevalin™, Zinecard®, Zoladex®, Zoledronic acid, Zolinza, Zometa®

In the treatment of conditions which require inhibition or negative modulation of β-catenin/Tcf protein-protein interaction, an appropriate dosage level will generally be about 0.01 to 1000 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting or negatively modulating β-catenin/Tcf protein-protein interaction in at least one cell, comprising the step of contacting the at least one cell with at least one compound of the invention, in an amount effective to negatively modulate β-catenin/Tcf protein-protein interaction in the at least one cell. In a further aspect, the cell is mammalian, for example human. In a further aspect, the cell has been isolated from a subject prior to the contacting step. In a further aspect, contacting is via administration to a subject.

In various aspects, disclosed are methods for the treatment of a disorder of uncontrolled cellular proliferation in a mammal comprising the step of administering to the mammal an effective amount of at least one compound having a structure represented by a formula:

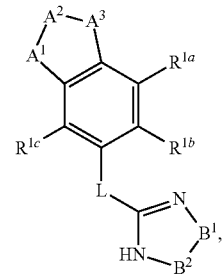

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for the treatment of a disorder of uncontrolled cellular proliferation associated with a β-catenin/Tcf protein-protein interaction dysfunction in a mammal comprising the step of administering to the mammal an effective amount of at least one compound having a structure represented by a formula:

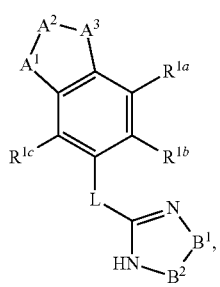

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in a mammal comprising the step of administering to the mammal an effective amount of at least one compound having a structure represented by a formula:

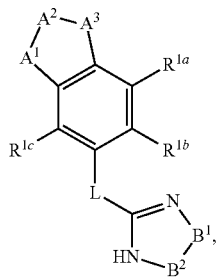

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for down-regulation of the Wnt pathway in a mammal comprising the step of administering to the mammal an effective amount of at least one compound having a structure represented by a formula:

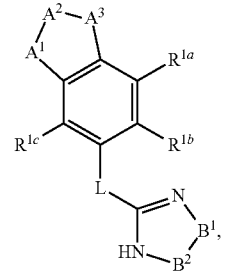

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in at least one cell comprising the step comprising the step of contacting the cell with an effective amount of at least one compound having a structure represented by a formula:

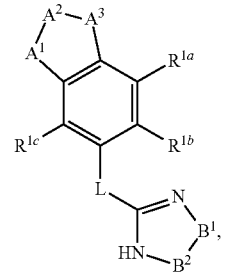

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In various aspects, disclosed are methods for the treatment of a disorder of uncontrolled cellular proliferation in a mammal comprising the step of administering to the mammal an effective amount of at least one compound having a structure represented by a formula:

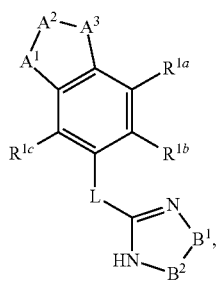

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for the treatment of a disorder of uncontrolled cellular proliferation associated with a β-catenin/Tcf protein-protein interaction dysfunction in a mammal comprising the step of administering to the mammal an effective amount of at least one compound having a structure represented by a formula:

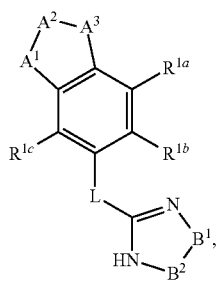

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in a mammal comprising the step of administering to the mammal an effective amount of at least one compound having a structure represented by a formula:

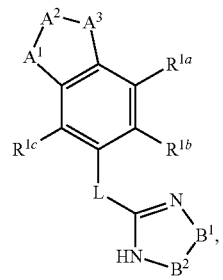

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for down-regulation of the Wnt pathway in a mammal comprising the step of administering to the mammal an effective amount of at least one compound having a structure represented by a formula:

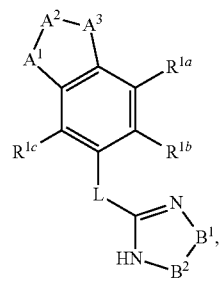

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in at least one cell comprising the step comprising the step of contacting the cell with an effective amount of at least one compound having a structure represented by a formula:

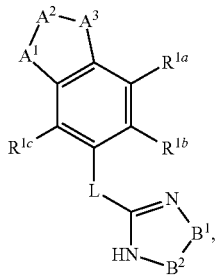

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In various aspects, disclosed are methods for the treatment of a disorder of uncontrolled cellular proliferation in a mammal comprising the step of administering to the mammal an effective amount of at least one compound having a structure represented by a formula:

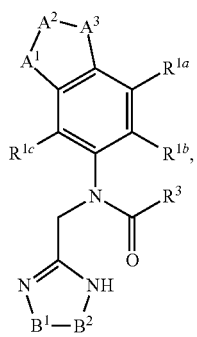

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), (C═S), and (S═O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-Ar$^1$, —(C1-C6)-Ar$^2$, and —(C1-C6)-Cy$^1$; wherein Ar$^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for the treatment of a disorder of uncontrolled cellular proliferation associated with a β-catenin/Tcf protein-protein interaction dysfunction in a mammal comprising the step of administering to the mammal an effective amount of at least one compound having a structure represented by a formula:

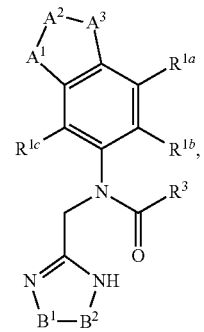

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), (C═S), and (S═O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein R³ is selected from C1-C6 alkyl, C1-C6 monohaloalkyl, C1-C6 polyhaloalkyl, Ar¹, Ar², Cy¹, —(C1-C6)-Ar¹, —(C1-C6)-Ar², and —(C1-C6)-Cy¹; wherein Ar¹ is phenyl substituted with 0-3 substituents independently selected from halogen, —OH, —NH₂, C1-C3 haloalkyl, C1-C3 polyhaloalkyl, and C1-C3 alkoxy; wherein Ar² is monocyclic heteroaryl substituted with 0-3 substituents independently selected from halogen, —OH, —NH₂, C1-C3 haloalkyl, C1-C3 polyhaloalkyl, and C1-C3 alkoxy; and wherein Cy¹ is C3-C6 cycloalkyl or C2-C5 heterocycloalkyl substituted with 0-3 substituents independently selected from halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in a mammal comprising the step of administering to the mammal an effective amount of at least one compound having a structure represented by a formula:

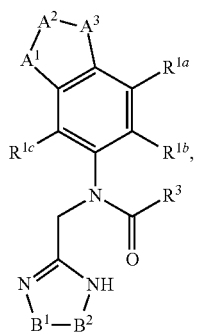

wherein A¹ is selected from —N=, —NH—, and —CR²ᵃ=; wherein A² is selected from =N—, (C=O), (C=S), and =CR²ᵇ—; wherein A³ is selected from —N(OH)— and —O—; provided that valency is satisfied for A¹, A², and A³; wherein L is selected from —CH₂—, —(CH₂)₂—, —(CH₂)₃—, —OCH₂—, —NHCH₂—, —CH₂NHCH₂—, and —CH₂OCH₂—; wherein B¹ is selected from —N=, —O—, and —S—; wherein B² is selected from =N—, (C=O), (C=S), and (S=O); provided that valency is satisfied for B¹ and B²; wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy; wherein R³ is selected from C1-C6 alkyl, C1-C6 monohaloalkyl, C1-C6 polyhaloalkyl, Ar¹, Ar², Cy¹, —(C1-C6)-Ar¹, —(C1-C6)-Ar², and —(C1-C6)-Cy¹; wherein Ar¹ is phenyl substituted with 0-3 substituents independently selected from halogen, —OH, —NH₂, C1-C3 haloalkyl, C1-C3 polyhaloalkyl, and C1-C3 alkoxy; wherein Ar² is monocyclic heteroaryl substituted with 0-3 substituents independently selected from halogen, —OH, —NH₂, C1-C3 haloalkyl, C1-C3 polyhaloalkyl, and C1-C3 alkoxy; and wherein Cy¹ is C3-C6 cycloalkyl or C2-C5 heterocycloalkyl substituted with 0-3 substituents independently selected from halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for down-regulation of the Wnt pathway in a mammal comprising the step of administering to the mammal an effective amount of at least one compound having a structure represented by a formula:

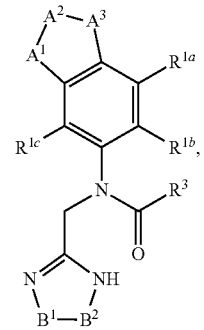

wherein A¹ is selected from —N=, —NH—, and —CR²ᵃ=; wherein A² is selected from =N—, (C=O), (C=S), and =CR²ᵇ—; wherein A³ is selected from —N(OH)— and —O—; provided that valency is satisfied for A¹, A², and A³; wherein L is selected from —CH₂—, —(CH₂)₂—, —(CH₂)₃—, —OCH₂—, —NHCH₂—, —CH₂NHCH₂—, and —CH₂OCH₂—; wherein B¹ is selected from —N=, —O—, and —S—; wherein B² is selected from =N—, (C=O), (C=S), and (S=O); provided that valency is satisfied for B¹ and B²; wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy; wherein R³ is selected from C1-C6 alkyl, C1-C6 monohaloalkyl, C1-C6 polyhaloalkyl, Ar¹, Ar², Cy¹, —(C1-C6)-Ar¹, —(C1-C6)-Ar², and —(C1-C6)-Cy¹; wherein Ar¹ is phenyl substituted with 0-3 substituents independently selected from halogen, —OH, —NH₂, C1-C3 haloalkyl, C1-C3 polyhaloalkyl, and C1-C3 alkoxy; wherein Ar² is monocyclic heteroaryl substituted with 0-3 substituents independently selected from halogen, —OH, —NH₂, C1-C3 haloalkyl, C1-C3 polyhaloalkyl, and C1-C3 alkoxy; and wherein Cy¹ is C3-C6 cycloalkyl or C2-C5 heterocycloalkyl substituted with 0-3 substituents independently selected from halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in at least one cell comprising the step comprising the step of contacting the cell with an effective amount of at least one compound having a structure represented by a formula:

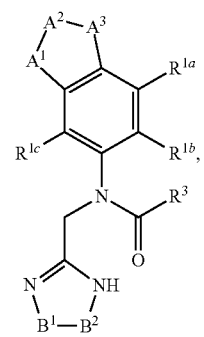

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), (C═S), and (S═O); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

In various aspects, disclosed are methods for the treatment of a disorder of uncontrolled cellular proliferation in a mammal comprising the step of administering to the mammal an effective amount of at least one compound having a structure represented by a formula:

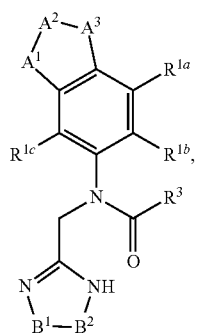

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for the treatment of a disorder of uncontrolled cellular proliferation associated with a β-catenin/Tcf protein-protein interaction dysfunction in a mammal comprising the step of administering to the mammal an effective amount of at least one compound having a structure represented by a formula:

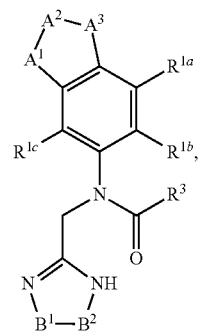

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in a mammal comprising the step of administering to the mammal an effective amount of at least one compound having a structure represented by a formula:

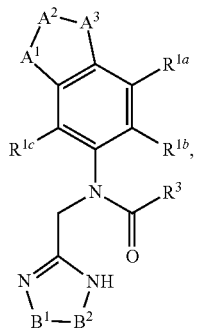

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-Ar$^1$, —(C1-C6)-Ar$^2$, and —(C1-C6)-Cy$^1$; wherein Ar$^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for down-regulation of the Wnt pathway in a mammal comprising the step of administering to the mammal an effective amount of at least one compound having a structure represented by a formula:

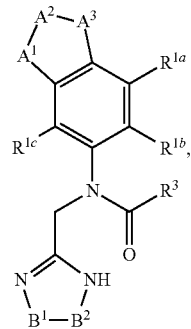

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-Ar$^1$, —(C1-C6)-Ar$^2$, and —(C1-C6)-Cy$^1$; wherein Ar$^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof.

Also disclosed are methods for inhibiting β-catenin/Tcf protein-protein interactions in at least one cell comprising the step comprising the step of contacting the cell with an effective amount of at least one compound having a structure represented by a formula:

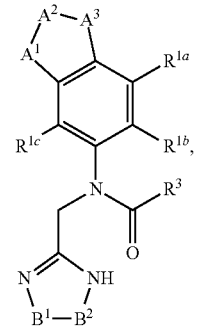

wherein $A^1$ is selected from —N=, —NH—, and —CR$^{2a}$=; wherein $A^2$ is selected from =N—, (C=O), (C=S), and =CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, Ar$^1$, Ar$^2$, Cy$^1$, —(C1-C6)-

$Ar^1$, —(C1-C6)-$Ar^2$, and —(C1-C6)-$Cy^1$; wherein $Ar^1$ is phenyl substituted with 0-3 substituents independently selected from halogen, —OH, —$NH_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —$NH_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

2. Manufacture of a Medicament

In one aspect, the invention relates to a method for the manufacture of a medicament for inhibition of β-catenin/Tcf protein-protein interaction in a mammal comprising combining a therapeutically effective amount of a disclosed compound or product of a disclosed method with a pharmaceutically acceptable carrier or diluent. In a further aspect, the invention relates to a method for the manufacture of a medicament for inhibition of the Wnt signaling pathway in a mammal comprising combining a therapeutically effective amount of a disclosed compound or product of a disclosed method with a pharmaceutically acceptable carrier or diluent.

3. Use of Compounds

In one aspect, the invention relates to the use of a compound having a structure represented by a formula:

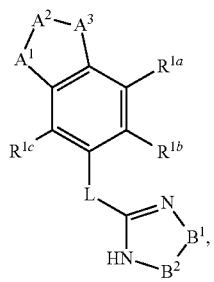

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

In various aspects, the invention relates to the use of a compound having a structure represented by a formula:

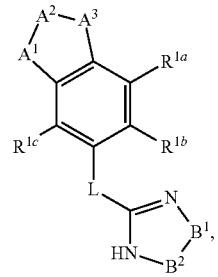

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), and (C=S); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof.

In various aspects, the invention relates to the use of a compound having a structure represented by a formula:

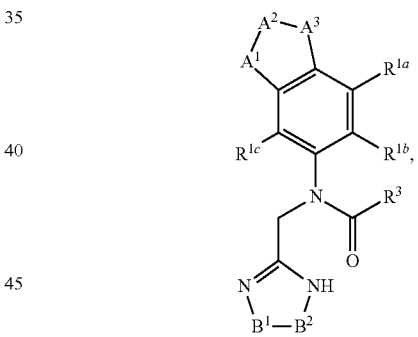

wherein $A^1$ is selected from —N=, —NH—, and —$CR^{2a}$=; wherein $A^2$ is selected from =N—, (C=O), (C=S), and =$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N=, —O—, and —S—; wherein $B^2$ is selected from =N—, (C=O), (C=S), and (S=O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —NH₂, C1-C3 haloalkyl, C1-C3 polyhaloalkyl, and C1-C3 alkoxy; wherein Ar² is monocyclic heteroaryl substituted with 0-3 substituents independently selected from halogen, —OH, —NH₂, C1-C3 haloalkyl, C1-C3 polyhaloalkyl, and C1-C3 alkoxy; and wherein Cy¹ is C3-C6 cycloalkyl or C2-C5 heterocycloalkyl substituted with 0-3 substituents independently selected from halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

In various aspects, the invention relates to the use of a compound having a structure represented by a formula:

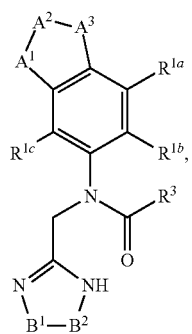

wherein A¹ is selected from —N═, —NH—, and —CR²ᵃ═; wherein A² is selected from ═N—, (C═O), (C═S), and ═CR²ᵇ—; wherein A³ is selected from —N(OH)— and —O—; provided that valency is satisfied for A¹, A², and A³; wherein L is selected from —CH₂—, —(CH₂)₂—, —(CH₂)₃—, —OCH₂—, —NHCH₂—, —CH₂NHCH₂—, and —CH₂OCH₂—; wherein B¹ is selected from —N═, —O—, and —S—; wherein B² is selected from ═N—, (C═O), and (C═S); provided that valency is satisfied for B¹ and B²; wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy; wherein R³ is selected from C1-C6 alkyl, C1-C6 monohaloalkyl, C1-C6 polyhaloalkyl, Ar¹, Ar², Cy¹, —(C1-C6)-Ar¹, —(C1-C6)-Ar², and —(C1-C6)-Cy¹; wherein Ar¹ is phenyl substituted with 0-3 substituents independently selected from halogen, —OH, —NH₂, C1-C3 haloalkyl, C1-C3 polyhaloalkyl, and C1-C3 alkoxy; wherein Ar² is monocyclic heteroaryl substituted with 0-3 substituents independently selected from halogen, —OH, —NH₂, C1-C3 haloalkyl, C1-C3 polyhaloalkyl, and C1-C3 alkoxy; and wherein Cy¹ is C3-C6 cycloalkyl or C2-C5 heterocycloalkyl substituted with 0-3 substituents independently selected from halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

In a further aspect, the compound of the use is a disclosed compound or a product of a disclosed method of making a compound.

In a still further aspect, the use is therapeutic treatment of a mammal. In a yet further aspect, the mammal is human.

In a further aspect, the use is inhibition of β-catenin/Tcf protein-protein interactions. In a still further aspect, the use is inhibition of the Wnt signaling pathway. In a still further aspect, the need for inhibition of β-catenin/Tcf protein-protein interactions is associated with treatment of a disorder of uncontrolled cellular proliferation. In a yet further aspect, inhibition of the Wnt signaling pathway treats a disorder of uncontrolled cellular proliferation.

In a further aspect, the disorder of uncontrolled cellular proliferation is a cancer. In an even further aspect, cancer is a leukemia. In a still further aspect, the cancer is a meyloma. In a yet further aspect, cancer is a solid tumor. In an even further aspect, the cancer is a lymphoma.

In a further aspect, the cancer is selected from the cancer is selected from cancers of the blood, brain, prostate, genitourinary tract, gastrointestinal tract, colon, rectum, breast, livery, kidney, lymphatic system, stomach, lung, pancreas, and skin. In an even further aspect, the cancer is selected from a cancer of the colon, rectum, breast, prostate, liver, skin and lung. In a still further aspect, the cancer is selected from a cancer of the breast, ovary, testes and prostate. In a yet further aspect, the cancer is a cancer of the breast. In various aspect, the cancer is a cancer of the liver. In a still further aspect, the cancer is a cancer of the prostate. In a yet further aspect, the cancer is a cancer of the colon or rectum.

In a further aspect, the disorder is characterized by fibrosis. In a yet further aspect, the fibrotic disorder is selected from pulmonary fibrosis, liver fibrosis, and polycystic kidney disease.

4. Kits

In one aspect, the invention relates to a kit comprising at least one compound having a structure represented by a formula:

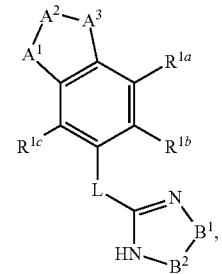

wherein A¹ is selected from —N═, —NH—, and —CR²ᵃ═; wherein A² is selected from ═N—, (C═O), (C═S), and ═CR²ᵇ—; wherein A³ is selected from —N(OH)— and —O—; provided that valency is satisfied for A¹, A², and A³; wherein L is selected from —CH₂—, —(CH₂)₂—, —(CH₂)₃—, —OCH₂—, —NHCH₂—, —CH₂NHCH₂—, and —CH₂OCH₂—; wherein B¹ is selected from —N═, —O—, and —S—; wherein B² is selected from ═N—, (C═O), (C═S), and (S═O); provided that valency is satisfied for B¹ and B²; wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof, and one or more of:

(a) at least one agent known to activate the Wnt pathway;
(b) at least one agent known to inhibit the Wnt pathway;
(c) at least one agent known to treat a disorder of uncontrolled cellular proliferation; or
(d) instructions for treating a disorder associated with uncontrolled cellular proliferation.

In various aspects, the invention relates to a kit comprising at least one compound having a structure represented by a formula:

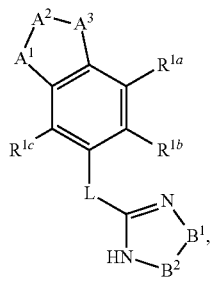

wherein $A^1$ is selected from —N═, —NH—, and —$CR^{2a}$═; wherein $A^2$ is selected from ═N—, (C═O), (C═S), and ═$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof, and one or more of:

(a) at least one agent known to activate the Wnt pathway;
(b) at least one agent known to inhibit the Wnt pathway;
(c) at least one agent known to treat a disorder of uncontrolled cellular proliferation; or
(d) instructions for treating a disorder associated with uncontrolled cellular proliferation.

In various aspects, the invention relates to a kit comprising at least one compound having a structure represented by a formula:

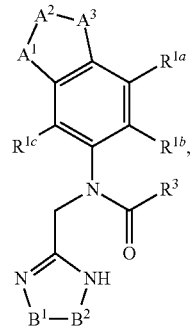

wherein $A^1$ is selected from —N═, —NH—, and —$CR^{2a}$═; wherein $A^2$ is selected from ═N—, (C═O), (C═S), and ═$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N═, —O—, and —S—; wherein $B^2$ is selected from ═N—, (C═O), (C═S), and (S═O); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —$NH_2$, C1-C3 haloalkyl, C1-C3 polyhaloalkyl, and C1-C3 alkoxy; wherein $Ar^2$ is monocyclic heteroaryl substituted with 0-3 substituents independently selected from halogen, —OH, —$NH_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —$NH_2$, C1-C3 haloalkyl, C1-C3 polyhaloalkyl, and C1-C3 alkoxy; or pharmaceutically acceptable salt, ester, hydrate, solvate, or polymorph thereof, or pharmaceutically acceptable salt, ester, hydrate, solvate, or polymorph thereof, and one or more of:

(a) at least one agent known to activate the Wnt pathway;
(b) at least one agent known to inhibit the Wnt pathway;
(c) at least one agent known to treat a disorder of uncontrolled cellular proliferation; or
(d) instructions for treating a disorder associated with uncontrolled cellular proliferation.

In various aspects, the invention relates to a kit comprising at least one compound having a structure represented by a formula:

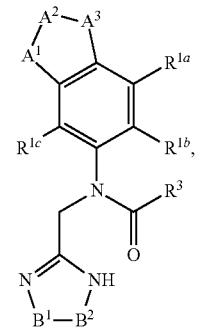

wherein $A^1$ is selected from —N═, —NH—, and —$CR^{2a}$═; wherein $A^2$ is selected from ═N—, (C═O), (C═S), and ═$CR^{2b}$—; wherein $A^3$ is selected from —N(OH)— and —O—; provided that valency is satisfied for $A^1$, $A^2$, and $A^3$; wherein L is selected from —$CH_2$—, —$(CH_2)_2$—, —$(CH_2)_3$—, —$OCH_2$—, —$NHCH_2$—, —$CH_2NHCH_2$—, and —$CH_2OCH_2$—; wherein $B^1$ is selected from —N═, —O—, and —S—; wherein $B^2$ is selected from ═N—, (C═O), and (C═S); provided that valency is satisfied for $B^1$ and $B^2$; wherein each of $R^{1a}$, $R^{1b}$, and $R^{1c}$ is independently selected from hydrogen, halogen, —OH, —$NH_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —$NH_2$, C1-C3 haloalkyl, C1-C3 polyhaloalkyl, and C1-C3 alkoxy; wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$; wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy; wherein Ar$^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein Cy$^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof; or pharmaceutically acceptable salt, ester, hydrate, solvate, or polymorph thereof, and one or more of:

(a) at least one agent known to activate the Wnt pathway;
(b) at least one agent known to inhibit the Wnt pathway;
(c) at least one agent known to treat a disorder of uncontrolled cellular proliferation; or
(d) instructions for treating a disorder associated with uncontrolled cellular proliferation.

In a further aspect, the compound of the kit is a disclosed compound or a product of a disclosed method of making a compound.

In a further aspect, the at least one compound or the at least one product and the at least one agent are co-formulated. In a still further aspect, the at least one compound or the at least one product and the at least one agent are co-packaged.

In a further aspect, the at least one agent is a hormone therapy agent. In a yet further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a yet further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof.

In a further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the disorder of uncontrolled cellular proliferation is associated with a β-catenin/Tcf protein-protein interaction dysfunction. In a still further aspect, the disorder of uncontrolled cellular proliferation is a cancer. In an even further aspect, cancer is a leukemia. In a still further aspect, the cancer is a sarcoma. In a yet further aspect, cancer is a solid tumor. In an even further aspect, the cancer is a lymphoma. In a still further aspect, the cancer is selected from chronic lymphocytic leukemia, small lymphocytic lymphoma, B-cell non-Hodgkin lymphoma, and large B-cell lymphoma. In a yet further aspect, the cancer is selected from cancers of the blood, brain, genitourinary tract, gastrointestinal tract, colon, rectum, breast, livery, kidney, lymphatic system, stomach, lung, pancreas, and skin. In an even further aspect, the cancer is selected from a cancer of the lung and liver. In a still further aspect, the cancer is selected from a cancer of the breast, ovary, testes and prostate. In a yet further aspect, the cancer is a cancer of the breast. In various aspect, the cancer is a cancer of the ovary. In a still further aspect, the cancer is a cancer of the prostate. In a yet further aspect, the cancer is a cancer of the testes.

5. Non-Medical Uses

Also provided are the uses of the disclosed compounds and products as pharmacological tools in the development and standardization of in vitro and in vivo test systems for the evaluation of the effects of inhibitors of β-catenin/Tcf protein-protein interactions in laboratory animals such as cats, dogs, rabbits, monkeys, rats and mice, as part of the search for new therapeutic agents that inhibit β-catenin/Tcf protein-protein interactions.

E. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. Materials

AlphaScreen His-tag fusion detection 10000 assay point kit and Opti-384 plates were purchased from PerkinElmer (Waltham, Mass.). 96-Well Microfluor 2 black plates were purchased from Thermo Fisher Scientific (Waltham, Mass.). β-catenin (residues 138-686) was cloned into a pEHISTEV vector carrying a N-terminal 6× histidine (obtained from Dr. Hanting Liu, St. Andrew University, UK) and transformed into *E. coli* BL21 DE3 (Novagen). Cells were cultured in LB medium with 30 g/mL kanamycin until the $OD_{600}$ was approximately 0.8, and then protein expression was induced with 400 μM of IPTG at 20° C. overnight. Cells were lysed by sonication and the proteins were purified by Ni-NTA affinity chromatography (Qiagen 30210) and dialyzed against a buffer containing 20 mM of HEPES (pH=7.5), 200 mM of NaCl, 10% glycerol, and 5 mM of DTT. Proteins were aliquoted and stored at −80° C.

C-terminal biotinylated or fluorescein-labeled oligopeptides, as well as unlabeled oligopeptides were synthesized from core facility of the University of Utah, as shown in Table 1.

TABLE 1

| Peptide/SEQ ID NO: | Sequences |
|---|---|
| Biotinylated Tcf4 45-mer SEQ ID NO: 1 | H-[7]GGGDDLGANDELISFKDEGE QEEKSSENSSAERDLADVKSSL VNE[51]K(Biotin)-NH$_2$ |
| Fluorescein-labeled Tcf4 45-mer SEQ ID NO: 2 | H-[7]GGGDDLGANDELISFKDEGE QEEKSSENSSAERDLADVKSSL VNE[51]K(FITC)-NH$_2$ |
| Biotinylated E-cadherin 55-mer SEQ ID NO: 3 | H-[819]DTDPTAPPYDSLLVFDYE GSGSEAASLSSLNSSESDKDQD YDYLNEWGNRFKKLA[873]K(Biotin)-NH$_2$ |
| Fluorescein-labeled E-cadherin 55-mer SEQ ID NO: 4 | H-[819]DTDPTAPPYDSLLVFDYE GSGSEAASLSSLNSSESDKDQD YDYLNEWGNRFKKLA[873]K(FITC)-NH$_2$ |
| Biotinylated APC-R3 43-mer SEQ ID NO: 5 | H-[1477]QRVQVLPDADTLLHFAT ESTPDGFSCSSSLSALSLDEP FIQKD[1519]K(Biotin)-NH$_2$ |
| Fluorescein-labeled APC-R3 43-mer SEQ ID NO: 6 | H-[1477]QRVQVLPDADTLLHFAT ESTPDGFSCSSSLSALSLDEPF IQKD[1519]K(FITC)-NH$_2$ |

2. Preparation of 5-((1H-tetrazol-5-yl)methyl)-1H-benzo[d][1,2,3]triazol-1-ol (Compound 1).

The overall synthesis scheme (Synthesis Scheme 1) for the preparation of Compound 1 is shown below. The synthesis proceeds through the intermediates indicated (Compounds 29, 30, 31, 32 and 33). The yield for each synthetic step was as indicated.

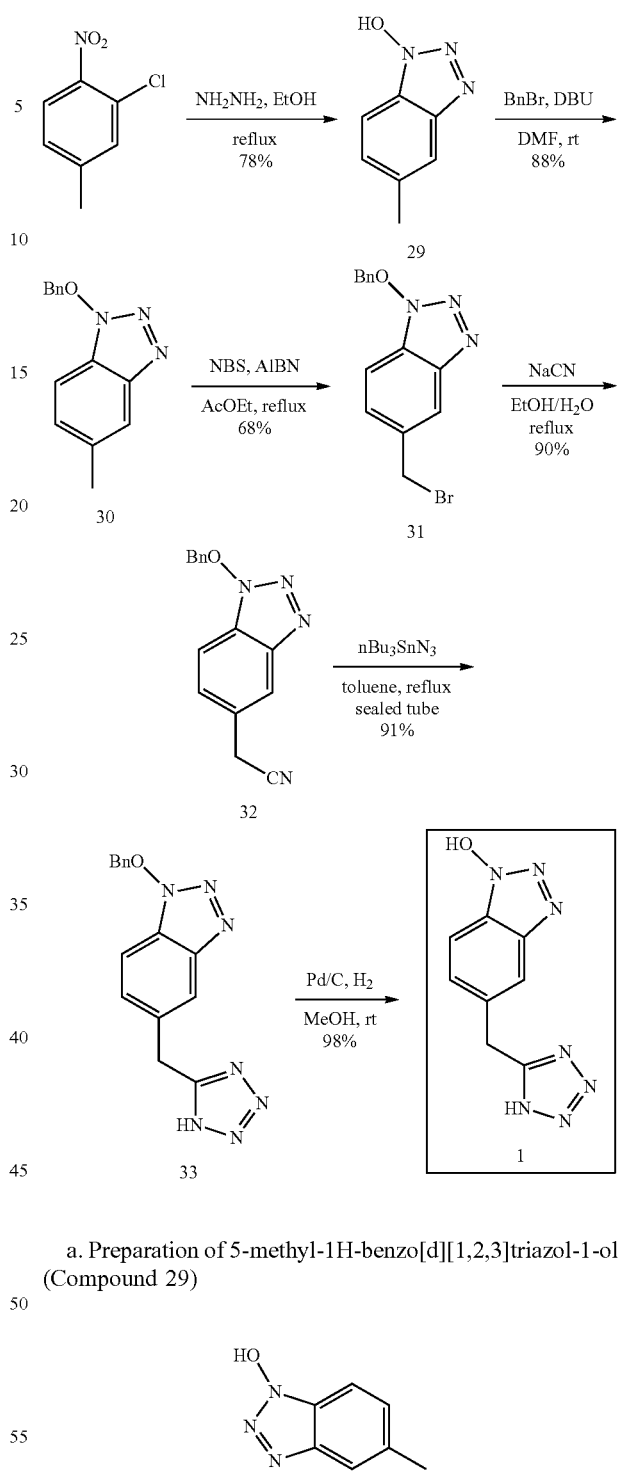

a. Preparation of 5-methyl-1H-benzo[d][1,2,3]triazol-1-ol (Compound 29)

To a solution of 2-chloro-4-methyl-1-nitrobenzene (4.0 g, 23.3 mmol) in EtOH (50 mL) was added hydrazine hydrate (21.3 mL, 232.0 mmol, 10 equiv.). The mixture was stirred under reflux for 24 h, and then the solvent was removed by rotary evaporation. The residue was taken in 50 mL of cold water and acidified with HCl 1.5 M to pH 4. The product precipitated and was isolated by filtration. Drying under high vacuum at 40° C. gave the desired product 29 (2.7 g, 78% yield) as a white solid: mp 183-184° C.

b. Preparation of 1-(benzyloxy)-5-methyl-1H-benzo[d][1,2,3]triazole (Compound 30).

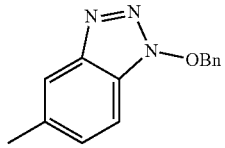 [SMILES: Cc1ccc2c(c1)nnn2OCc1ccccc1]

Benzyl bromide (481.3 mg, 2.81 mmol) was added dropwise to an ice-cooled mixture of 29 (400.0 mg, 2.68 mmol) and DBU (427.5 mg, 2.81 mmol) in $CH_2Cl_2$ (10 mL). The resulting mixture was stirred at rt for 30 min, diluted with water, and extracted with EtOAc (10 mL×2). The extract was washed with water and brine, and dried over $Na_2SO_4$. The solvent was evaporated in vacuo. The residue was purified by column chromatography (silica gel, hexanes:EtOAc=4:1) to yield a colorless oil 30 (564.0 mg, 88% yield).

c. Preparation of 1-(benzyloxy)-5-(bromomethyl)-1H-benzo[d][1,2,3]triazole (Compound 31).

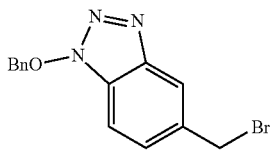 [SMILES: BrCc1ccc2c(c1)nnn2OCc1ccccc1]

A solution of 30 (3.2 g, 13.4 mol) in EtOAc (200 mL) was heated to reflux after which N-bromosuccinimide (2.9 g, 14.8 mol) and AIBN (220 mg, 1.34 mol) were carefully added in a portionwise manner over 5 min. After 3 h the mixture was cooled to room temperature. The solvent was evaporated in vacuo. The toluene (100 mL) was added to the residue. The succinimide, which resulted, was filtered off and washed with toluene (10 mL×3). The solvent was removed under reduced pressure and purified by column chromatography (silica gel hexanes:EtOAc=6:1) to give the desired product 31 (2.9 g, 9.1 mmol, 68% yield) as a colorless solid: mp 91-93° C.

d. Preparation of 2-(1-(benzyloxy)-1H-benzo[d][1,2,3]triazol-5-yl)acetonitrile (Compound 32).

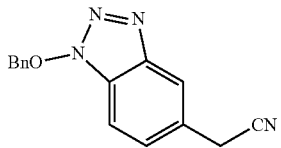 [SMILES: N#CCc1ccc2c(c1)nnn2OCc1ccccc1]

A mixture of compound 31 (313 mg, 0.98 mmol), NaCN (96 mg, 1.97 mmol) in ethanol/$H_2O$ (20 mL/4 mL) was refluxed for 45 min. The mixture was evaporated and the residue was diluted with water and extracted with AcOEt. The extract was washed with water and brine, and dried over $Na_2SO_4$. The solvent was evaporated in vacuo. The residue was purified by column chromatography (silica gel, hexanes:EtOAc=2:1) to yield 32 (232.8 mg, 90%) as a colorless solid: mp 104-106° C.

e. Preparation of 5-((1H-tetrazol-5-yl)methyl)-1-(benzyloxy)-1H-benzo[d][1,2,3]triazole (Compound 33).

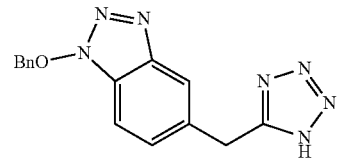 [SMILES: c1ccc(COn2nnc3cc(Cc4nnn[nH]4)ccc32)cc1]

A solution of 32 (135 mg, 0.51 mmol) and n-$Bu_3SnN_3$ (509.4 mg, 1.53 mmol) in toluene (2 mL) was refluxed for 24 h in a sealed tube. The mixture was cooled at room temperature, and acetate acid (0.3 mL) was added. After additional stirring for 2 h at room temperature, the resulting solid was filtered off, washed with hexane, and dried under vacuum to give 33 (142 mg, 91% yield) as white solid: mp 137-138° C. $^1$H NMR (300 MHz, DMSO) δ 7.93 (s, 1H), 7.52 (m, 1H), 7.46 (m, 3H), 7.37 (m, 3H), 5.57 (s, 2H), 4.43 (s, 2H). $^{13}$C NMR (75 MHz, DMSO) δ 155.99, 143.59, 133.97, 133.54, 130.82, 130.27, 130.19, 129.32, 127.22, 119.88, 110.29, 82.88, 29.39. HRMS (ESI) m/z calcd. for $C_{15}H_{12}N_7O$ [M−H]$^-$ 306.1103, found 306.1110.

f. Preparation of 5-((1H-tetrazol-5-yl)methyl)-1H-benzo[d][1,2,3]triazol-1-ol (Compound 1).

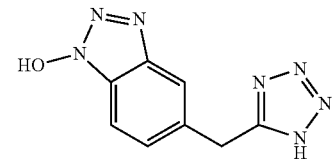 [SMILES: On1nnc2cc(Cc3nnn[nH]3)ccc21]

A solution of 33 (142 mg, 0.46 mol) in EtOH (10 mL) was treated with 10 wt % Pd carbon (15 mg). The reaction mixture was stirred at rt under a hydrogen atmosphere for 10 min. The catalyst was filtered through Celite. The Celite pad was washed with EtOH (10 mL×2). The combined filtrate was concentrated in vacuo to afford 1 (0.28 g, 85% yield) as white solid. $^1$H NMR (300 MHz, cd$_3$od) δ 7.83 (s, 1H), 7.72 (dd, J=8.7, 0.7 Hz, 1H), 7.47 (dd, J=8.7, 1.4 Hz, 1H), 4.51 (s, 2H). $^{13}$C NMR (75 MHz, cd$_3$od) δ 155.90, 142.07, 133.95, 128.50, 127.76, 117.52, 110.80, 48.67, 48.39, 48.11, 47.82, 47.54, 47.25, 46.97, 29.15. HRMS (ESI) m/z calcd. for $C_8H_7N_7ONa$ [M+Na]$^+$ 240.0610, found 240.0614.

3. Preparation of 3-((1-hydroxy-1H-benzo[d][1,2,3]triazol-5-yl)methyl)-1,2,4-oxadiazol-5(4H)-one (2).

The overall synthesis scheme (Synthesis Scheme 2) for the preparation of Compound 2 is shown below. The synthesis proceeds through the intermediates indicated (Compounds 32, 34 and 35). The yield for each synthetic step was as indicated.

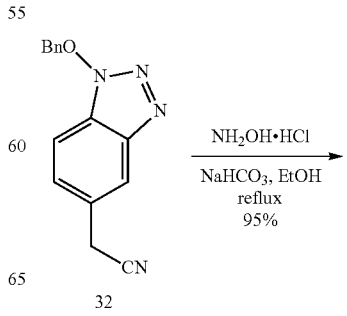

-continued

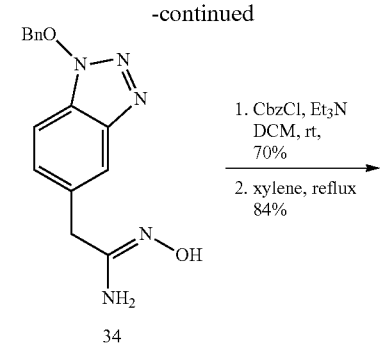

1. CbzCl, Et₃N
DCM, rt,
70%

2. xylene, reflux
84%

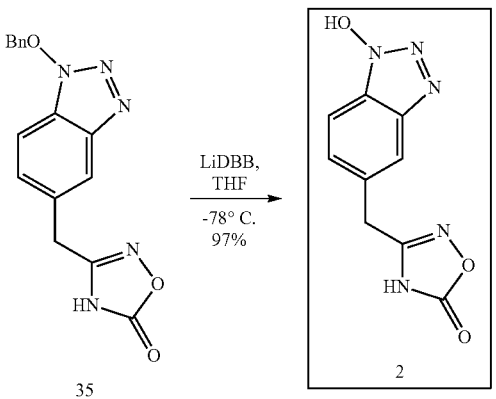

a. Preparation of (Z)-2-(1-(benzyloxy)-1H-benzo[d][1,2,3]triazol-5-yl)-N'-hydroxyacetimidamide (Compound 34).

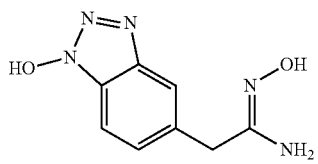 [SMILES: N/C(Cc1ccc2c(c1)nnn2O)=N\O]

A mixture of compound 32 (prepared as described above; 178 mg, 0.67 mmol), NaHCO₃ (453 mg, 5.39 mmol), and hydroxylamine hydrochloride (378 mg, 5.39 mmol) in EtOH (20 mL) was refluxed for 10 h and then was allowed to cool to room temperature. The reaction was filtered, and the residue washed with ethanol. The combined filtrate and washings were concentrated in vacuo. The reaction mixture was diluted with water and extracted with EtOAc. The organic phase was extracted with 1 N HCl (10 mL). The aqueous solution was adjusted to pH 8 with 1 N NaOH and extracted with EtOAc (20 mL×2). The organic solution was washed with water and dried over Na₂SO₄. The solvent was evaporated in vacuo to give the desired product, 34, (190 mg, 95% yield) as a white solid with a melting point of 149-151° C.

b. Preparation of 3-((1-(benzyloxy)-1H-benzo[d][1,2,3]triazol-5-yl)methyl)-1,2,4-oxadiazol-5(4H)-one (Compound 35).

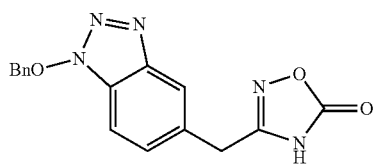 [SMILES: O=c1[nH]c(Cc2ccc3c(c2)nnn3OCc2ccccc2)no1]

Benzyl chloroformate (126 mg, 0.74 mmol) was added dropwise to an ice-cooled mixture of 34 (220 mg, 0.74 mmol) and pyridine (120 mg, 1.48 mmol) in CH₂Cl₂ (5 mL).

The resulting mixture was stirred at 0° C. for 30 min, diluted with water, and extracted with ethyl acetate. The extract was washed with brine and dried over Na₂SO₄. The solvent was evaporated in vacuo. The residue was purified by column chromatography (silica gel, hexanes:EtOAc=1:1) to yield product (223 mg, 70%) as colorless solid with a melting point of 109-111° C. The resulting product was dissolved in xylene (5 mL). The solution was heated under reflux for 3 h, and then was allowed to cool to room temperature. The mixture was purified by column chromatography (silica gel, EtOAc) to yield 35 (140.5 mg, 84% yield) as a white solid: mp 155-157° C. ¹H NMR (500 MHz, DMSO) δ 12.34 (br, 1H), 7.98 (s, 1H), 7.56 (d, J=8.6 Hz, 1H), 7.47 (m, 5H), 7.38 (m, 1H), 5.59 (s, 2H), 4.06 (s, 2H). ¹³C NMR (125 MHz, DMSO) δ 160.43, 159.64, 143.53, 133.97, 131.31, 130.82, 130.27, 130.21, 129.32, 127.37, 120.40, 110.24, 82.90, 31.11. MS (ESI) m/z=346.1 [M+Na]⁺.

c. Preparation of 3-((1-hydroxy-1H-benzo[d][1,2,3]triazol-5-yl)methyl)-1,2,4-oxadiazol-5(4H)-one (Compound 2).

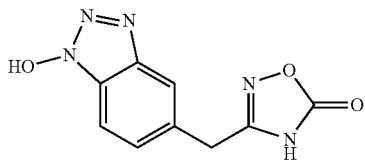 [SMILES: O=c1[nH]c(Cc2ccc3c(c2)nnn3O)no1]

To a solution of 35 (6.0 mg, 5.40 mol) in THF (3 mL) at −78° C. was added excess LiDBB (ca. 0.17 M solution in THF) until the blue color of LiDBB persisted. After 3 h, the reaction was quenched with NH₄Cl (aq, 5 mL). The aqueous phase was washed with EtOAc (10 mL×2) and then was acidified with 1 N HCl to pH to 4. The aqueous phase was exacted with EtOAc (20 mL×2). The organic phase was dried over Na₂SO₄ and concentrated to provide the product 2 (90.2 mg, 97% yield) as white solid. The 0.17 M LiDBB solution in THF was prepared as follows: to a mixture of di-tert-butylbiphenyl (0.37 g, 1.4 mmol) in THF (8 mL) at 0° C. was added lithium metal (60 mg, 8.6 mmol), and the resulting mixture was sonicated at 0° C. for 1 h and then stirred at 0° C. for 1 h. ¹H NMR (500 MHz, DMSO) δ 12.34 (br, 1H), 7.94 (s, 1H), 7.72 (d, J=8.6 Hz, 1H), 7.47 (d, J=8.6 Hz, 1H), 4.08 (s, 2H). ¹³C NMR (125 MHz, DMSO) δ 160.41, 159.72, 130.95, 130.82, 129.36, 127.86, 119.99, 110.60, 31.21. HRMS (ESI) m/z calcd. for C₉H₆N₅O₃[M−H]⁻ 232.0471, found 232.0487.

4. Preparation of 3-((1-hydroxy-1H-benzo[d][1,2,3]triazol-5-yl)methyl)-1,2,4-oxadiazole-5(4H)-thione (Compound 3).

The overall synthesis scheme (Synthesis Scheme 3) for the preparation of Compound 3 is shown below. The synthesis proceeds through the intermediates indicated (Compounds 34 and 36). The yield for each synthetic step was as indicated.

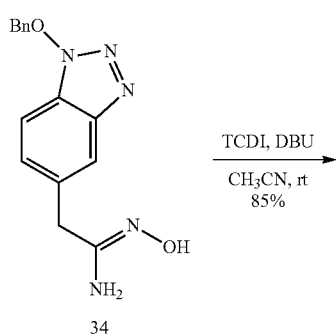

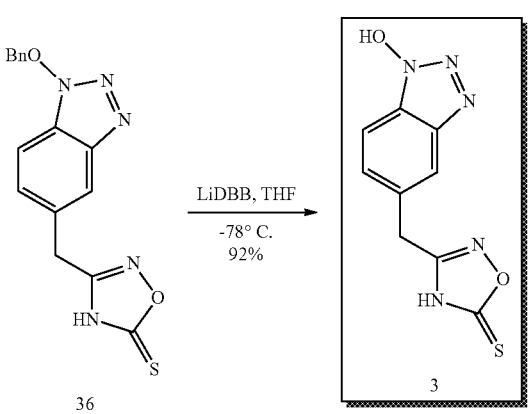

a. Preparation of Intermediate: 3-((1-(benzyloxy)-1H-benzo[d][1,2,3]triazol-5-yl)methyl)-1,2,4-oxadiazole-5(4H)-thione (Compound 36).

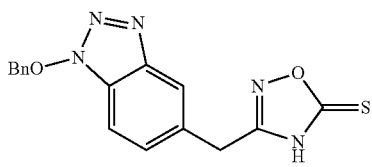

To a solution of 34 (prepared as described above; 380.0 mg, 1.28 mmol) in acetonitrile (10 ml), TCDI (356.6 mg, 1.92 mmol), DBU (778.9 g, 5.12 mmol) was added and reaction was stirred at room temperature for 4 h. The reaction mixture was diluted with water; its pH was adjusted to 4 by using 1 N HCl and extracted with EtOAc (20 mL×2). The extract was washed with water and brine, and dried over $Na_2SO_4$. The solvent was evaporated in vacuo. The obtained crude product was further purified by column chromatography (silica gel, DCM:MeOH=10:1) to give compound 36 (368.8 mg, 85% yield) as white solid: mp 164-166° C. $^1$H NMR (500 MHz, DMSO) δ 8.00 (s, 1H), 7.56 (dd, J=8.5, 4.0 Hz, 1H), 7.48 (m, 3H), 7.37 (m, 3H), 5.59 (s, 2H), 4.18 (s, 2H). $^{13}$C NMR (125 MHz, DMSO) δ 187.82, 161.28, 143.50, 133.96, 131.12, 130.83, 130.29, 130.27, 129.32, 127.41, 120.61, 110.30, 82.92, 29.89. MS (ESI) m/z=362.1 [M+Na]$^+$.

b. Preparation of 3-((1-hydroxy-1H-benzo[d][1,2,3]triazol-5-yl)methyl)-1,2,4-oxadiazole-5(4H)-thione (Compound 3).

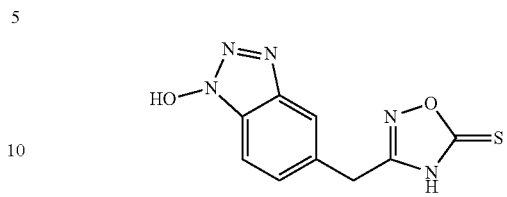

The procedure used to prepare 3 is the same as that to prepare 2 except 36 was used (82 mg, 0.24 mmol) instead of 35, afforded the desired product, 3, as a white solid (55 mg, 92% yield). $^1$H NMR (500 MHz, DMSO) δ 7.95 (s, 1H), 7.71 (d, J=8.6 Hz, 1H), 7.47 (d, J=8.6 Hz, 1H), 4.19 (s, 2H). $^{13}$C NMR (125 MHz, DMSO) δ 187.63, 161.22, 143.68, 130.67, 129.44, 127.91, 120.22, 110.67, 29.94. HRMS (ESI) m/z calcd. for $C_9H_6N_5O_2S$ [M–H]$^-$ 248.0242, found 248.0249.

5. Preparation of 5-(((1H-tetrazol-5-yl)methoxy)methyl)-1H-benzo[d][1,2,3]triazol-1-ol (Compound 4).

The overall synthesis scheme (Synthesis Scheme 4) for the preparation of Compound 4 is shown below. The synthesis proceeds through the intermediates indicated (Compounds 37, 38a, 38b, and 39). The yield for each synthetic step was as indicated.

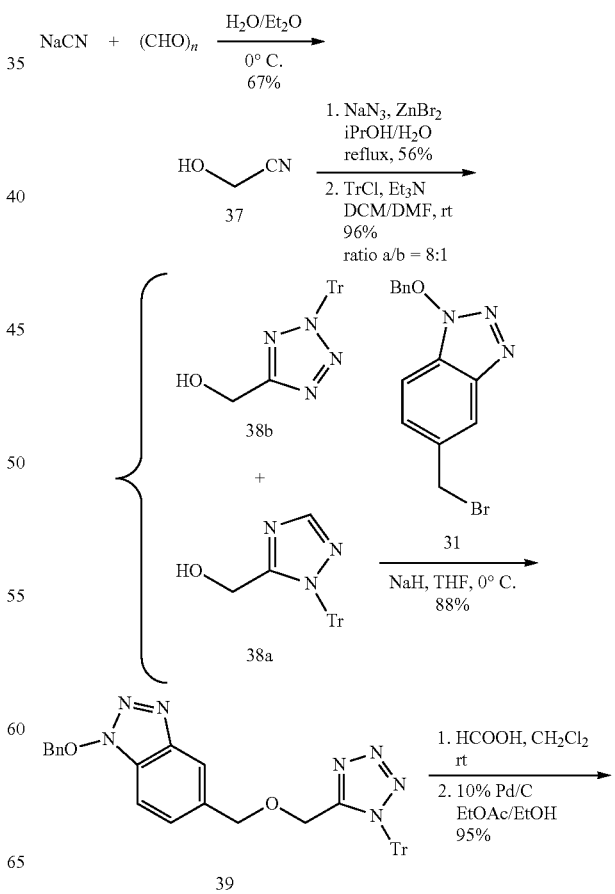

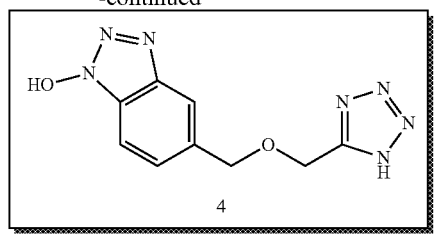

4 a. Preparation of 2-hydroxyacetonitrile (Compound 37).

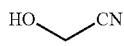

To a solution of NaCN (3.16 g, 64.6 mmol) in H$_2$O (10 mL) at 0° C. was added paraformaldehyde (1.96 g, 42.0 mmol). The reaction was stirred at 0° C. for 1 h at which time the PH was adjusted to 2.5 with concentrated H$_2$SO$_4$. The reaction mixture was extracted with Et$_2$O (100 mL×2). The extract was washed with water and brine, and dried over Na$_2$SO$_4$. The solvent was evaporated in vacuo. The obtained crude product 37 (1.60 g, 67% yield) as colorless oil that was directly used in next step without further purification.

b. Preparation of (1-trityl-1H-tetrazol-5-yl)methanol (Compounds 38a and 38b).

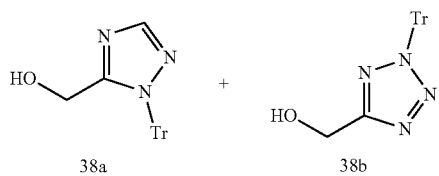

To a solution of 37 (1.60 g, 28.1 mmol) in 2-propanol (15 mL) and H$_2$O (30 mL) was added sodium azide (3.65 g, 56.1 mmol), zinc bromide (3.15 g, 14.0 mmol). The reaction mixture was stirred at reflux for 48 h. To the reaction were added 30 mL of 3 N HCl and of EtOAc (30 mL). The organic layer was isolated and the aqueous layer was extracted with EtOAc (20 mL×2). The combined organic layers were evaporated to yield the tetrazole as a solid (1.57 g, 56% yield). The crude tetrazole product was directly used in next step without further purification. To a solution of tetrazole (1.09 g, 10.9 mmol) in CH$_2$Cl$_2$ (20 mL) and DMF (5 mL) were added Et$_3$N (1.21 g, 12.0 mmol) and trityl chloride (3.04 g, 10.9 mmol). The resulting mixture was stirred at rt for 30 min, diluted with water, and extracted with CH$_2$Cl$_2$ (20 mL×2). The extract was washed with water and dried over Na$_2$SO$_4$. The solvent was evaporated in vacuo. The residue was purified by column chromatography (silica gel, hexanes:EtOAc=2:1) to yield 25b (411 mg, 11% yield) and 25a (3.18 g, 85% yield) as white solid: mp 162-163° C.

c. Preparation of 1-(benzyloxy)-5-(((1-trityl-1H-tetrazol-5-yl)methoxy)methyl)-1H-benzo[d][1,2,3]triazole (Compound 39).

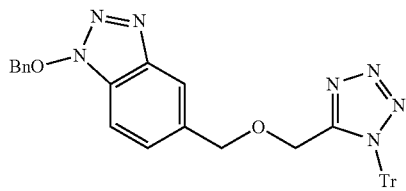

To a solution of 38a (880.0 mg, 2.56 mmol) in dry THF (15 mL) at 0° C. was added NaH 60% (112.8 mg, 2.82 mol) was added. Then the mixture was stirred for 1 h at −78° C. and a solution of 31 (814.1 mg, 2.56 mol) in THF (5 mL) was added dropwise over 10 min. The mixture was stirred at 0° C. for 15 min and warmed to rt over 1 h. aq. NH$_4$Cl was added to quench the reaction. The solution was extracted with EtOAc (20 mL×2). The organic layer was washed with brine, dried over anhydrous Na$_2$SO$_4$ and concentrated. The residue was purified by column chromatography (silica gel, hexanes:EtOAc=2:1) to yield 39 (1.02 g, 88% yield) as a colorless viscous oil. $^1$H NMR (300 MHz, CDCl$_3$) δ 7.86 (s, 1H), 7.33 (m, 17H), 7.10 (m, 5H), 5.51 (s, 2H), 4.84 (s, 2H), 4.69 (s, 2H). $^{13}$C NMR (75 MHz, CDCl$_3$) δ 162.10, 143.28, 141.09, 134.13, 133.00, 130.15, 129.95, 129.80, 128.81, 128.40, 128.30, 127.80, 127.68, 119.07, 108.82, 82.60, 72.17, 62.36. MS (ESI) m/z=602.2 [M+Na]$^+$.

d. Preparation of 5-(((1H-tetrazol-5-yl)methoxy)methyl)-1H-benzo[d][1,2,3]triazol-1-ol (Compound 4).

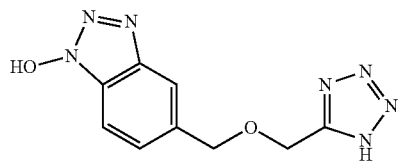 [SMILES: On1nnc2cc(COCc3nnn[nH]3)ccc21]

To a solution of 39 (250.0 mg, 0.43 mmol) in dry CH$_2$Cl$_2$ (4 mL) at 0° C. was added formic acid (6 mL). The resulting mixture was stirred for 2 h. The reaction mixture was concentrated and the residue was washed with solvent (hexanes:EtOAc=10:1) to afford the desired tetrazole (140 mg, 97% yield) as white solid: mp 159-159° C. A solution of tetrazole (140 mg, 0.42 mol) in EtOH (10 mL) was treated with 10 wt % Pd on carbon (15 mg). The reaction mixture was stirred at rt under a hydrogen atmosphere for 10 min. The catalyst was filtered through Celite. The Celite pad was washed with EtOH (10 mL×2). The combined filtrate was concentrated in vacuo to afford 4 (101 mg, 98% yield) as a white solid. $^1$H NMR (300 MHz, CD$_3$OD) δ 7.89 (m, 1H), 7.72 (dd, J=8.6, 0.8 Hz, 1H), 7.56 (dd, J=8.7, 1.3 Hz, 1H), 4.93 (s, 2H), 4.81 (s, 2H). $^{13}$C NMR (75 MHz, CD$_3$OD) δ 155.38, 141.89, 136.02, 128.03, 127.10, 116.45, 110.50, 72.50, 61.35. HRMS (ESI) m/z calcd. for C$_9$H$_9$N$_7$O$_2$Na [M+Na]$^+$ 270.0715, found 270.0713.

6. Preparation of 5-(2-(2H-tetrazol-5-yl)ethyl)-1H-benzo[d][1,2,3]triazol-1-ol (Compound 5).

The overall synthesis scheme (Synthesis Scheme 5) for the preparation of Compound 5 is shown below. The synthesis proceeds through the intermediates indicated (Compounds 31, 40, and 41). The yield for each synthetic step was as indicated.

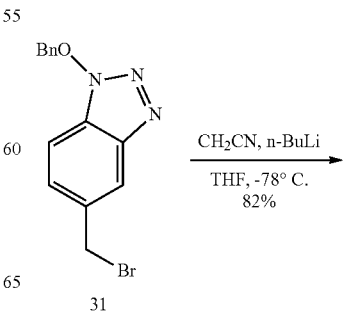

-continued

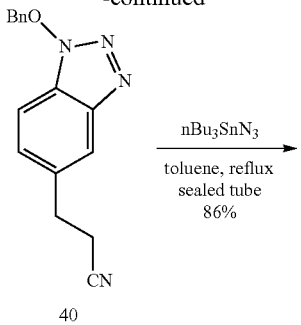

a. Preparation of 3-(1-(benzyloxy)-1H-benzo[d][1,2,3]triazol-5-yl)propanenitrile (Compound 40).

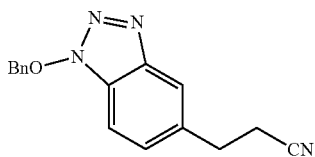 [SMILES: N#CCCc1ccc2c(c1)nnn2OCc1ccccc1]

Dry THF (5 mL) was cooled to −78° C. and 2.5 M n-BuLi (0.52 ml, 1.30 mmol) was added. A solution of CH₃CN (66.4 mg, 1.62 mmol) in dry THF (5 mL) was added dropwise over 10 min. Then the mixture was stirred for 1 h at −78° C. and a solution of 31 (prepared as described above; 344 mg, 1.08 mmol) in THF (5 mL) was added dropwise over 10 min. The mixture was stirred at −78° C. for 15 min and warmed to rt over 1 h. Aq NH₄Cl was added to quench the reaction. The solution was extracted with EtOAc (10 mL×2). The organic layer was washed with brine, dried over anhydrous Na₂SO₄ and concentrated. The residue was purified by column chromatography (silica gel, hexanes:EtOAc=2:1) to yield 40 (246 mg, 82% yield) as a pale yellow viscous oil.

b. Preparation of 5-(2-(2H-tetrazol-5-yl)ethyl)-1-(benzyloxy)-1H-benzo[d][1,2,3]triazole (Compound 41).

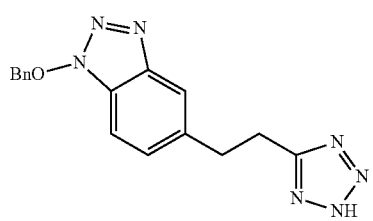 [SMILES: c1ccc(COn2nnc3cc(CCc4nn[nH]n4)ccc32)cc1]

The procedure used to prepare 41 was the same as that used to prepare 33 except 40 was used (149 mg, 0.54 mmol) instead of 32, afforded the desired product, 41, as a white solid (148 mg, 86% yield), mp: 152-154° C. ¹H NMR (500 MHz, CDCl₃) δ 7.80 (d, J=4.5 Hz, 1H), 7.44 (m, 3H), 7.35 (m, 4H), 5.54 (d, J=4.5 Hz, 1H), 3.23 (t, J=7.3 Hz, 2H), 3.17 (t, J=7.3 Hz, 2H). HRMS (ESI) m/z calcd. for C₁₆H₁₄N₇O [M−H]⁻ 320.1260, found 320.1265.

c. Preparation of 5-(2-(2H-tetrazol-5-yl)ethyl)-1H-benzo[d][1,2,3]triazol-1-ol (Compound 5).

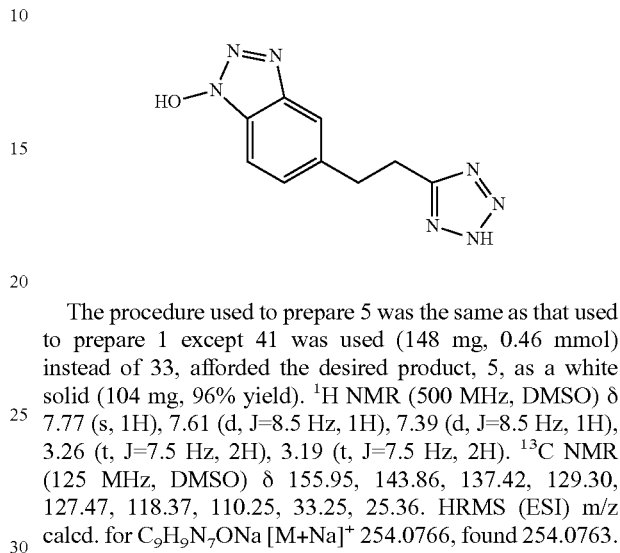

The procedure used to prepare 5 was the same as that used to prepare 1 except 41 was used (148 mg, 0.46 mmol) instead of 33, afforded the desired product, 5, as a white solid (104 mg, 96% yield). ¹H NMR (500 MHz, DMSO) δ 7.77 (s, 1H), 7.61 (d, J=8.5 Hz, 1H), 7.39 (d, J=8.5 Hz, 1H), 3.26 (t, J=7.5 Hz, 2H), 3.19 (t, J=7.5 Hz, 2H). ¹³C NMR (125 MHz, DMSO) δ 155.95, 143.86, 137.42, 129.30, 127.47, 118.37, 110.25, 33.25, 25.36. HRMS (ESI) m/z calcd. for C₉H₉N₇ONa [M+Na]⁺ 254.0766, found 254.0763.

7. Preparation of 3-(2-(1-hydroxy-1H-benzo[d][1,2,3]triazol-5-yl)ethyl)-1,2,4-oxadiazol-5(4H)-one (Compound 6).

The overall synthesis scheme (Synthesis Scheme 6) for the preparation of Compound 6 is shown below. The synthesis proceeds through the intermediates indicated (Compounds 40, 42, and 43). The yield for each synthetic step was as indicated.

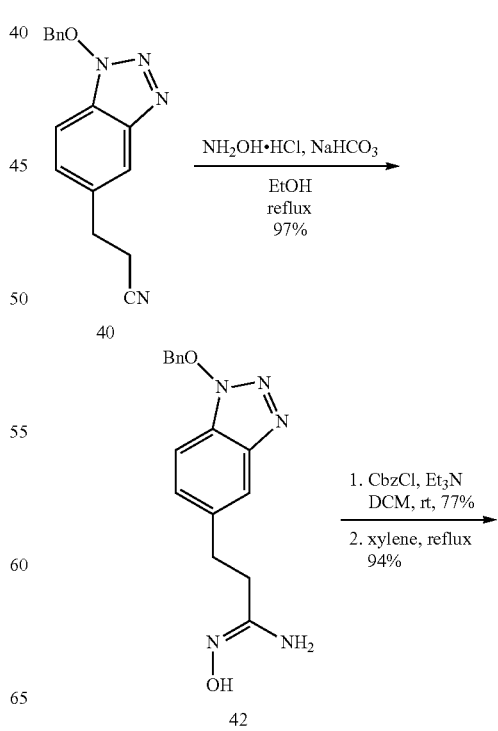

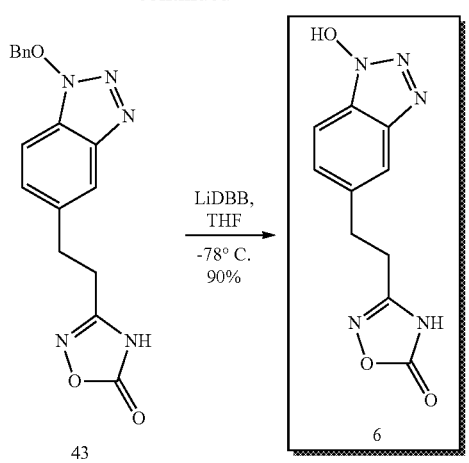

a. Preparation of (Z)-3-(1-(benzyloxy)-1H-benzo[d][1,2,3]triazol-5-yl)-N'-hydroxypropanimidamide (Compound 42).

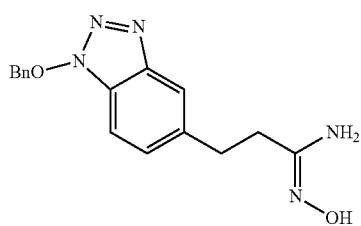 [SMILES: N/C(CCc1ccc2c(c1)nnn2OCc1ccccc1)=N\O]

The procedure used to prepare 42 was the same as that used to prepare 34 except 40 was used (prepared as decribed above; 444 mg, 1.60 mmol) instead of 32, afforded the desired product, 42, as a viscous colorless oil (477 mg, 96% yield).

b. Preparation of 3-(2-(1-(benzyloxy)-1H-benzo[d][1,2,3]triazol-5-yl)ethyl)-1,2,4-oxadiazol-5(4H)-one (Compound 43).

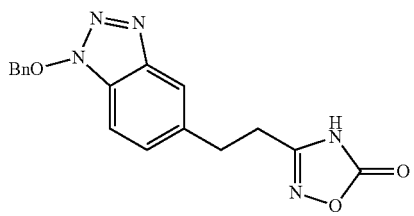 [SMILES: O=c1[nH]c(CCc2ccc3c(c2)nnn3OCc2ccccc2)no1]

The procedure used to prepare 43 was the same as that used to prepare 35 except 42 was used (147 mg, 0.47 mmol) instead of 34, afforded a white solid (115 mg, 72% yield for two steps): mp 157-158° C. $^1$H NMR (500 MHz, DMSO) δ 12.27 (br, 1H), 7.84 (s, 1H), 7.45 (m, 3H), 7.37 (m, 4H), 5.56 (s, 2H), 3.05 (t, J=7.5, 2H), 2.86 (t, J=7.5, 2H). $^{13}$C NMR (125 MHz, DMSO) δ 160.46, 159.87, 143.70, 137.34, 134.02, 130.11, 129.29, 127.00, 118.87, 109.89, 82.85, 30.98, 26.88. HRMS (ESI) m/z calcd. for $C_{17}H_{14}N_5O_3$ [M−H]⁻ 336.1097, found 336.1107.

c. Preparation of 3-(2-(1-hydroxy-1H-benzo[d][1,2,3]triazol-5-yl)ethyl)-1,2,4-oxadiazol-5(4H)-one (Compound 6).

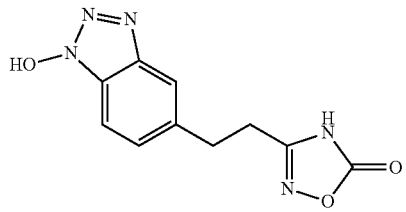 [SMILES: O=c1[nH]c(CCc2ccc3c(c2)nnn3O)no1]

The procedure used to prepare 6 was the same as that used to prepare 2 except 43 was used (46 mg, 0.14 mmol) instead of 35, afforded the desired product, 6, as a white solid (30 mg, 90% yield). $^1$H NMR (500 MHz, DMSO) δ 12.27 (br, 1H), 7.81 (s, 1H), 7.65 (d, J=8.0 Hz, 1H), 7.43 (d, J=8.0 Hz, 1H), 3.09 (t, J=7.5, 2H), 2.90 (t, J=7.5, 2H). $^{13}$C NMR (125 MHz, DMSO) δ 160.25, 159.72, 130.68, 130.10, 129.14, 127.36, 118.73, 109.76, 31.02, 26.85. HRMS (ESI) m/z calcd. for $C_{10}H_9N_5O_3Na$ [M+Na]⁺ 270.0603, found 270.0606.

8. Preparation of 3-(2-(1-hydroxy-1H-benzo[d][1,2,3]triazol-5-yl)ethyl)-1,2,4-oxadiazole-5(4H)-thione (Compound 7).

The overall synthesis scheme (Synthesis Scheme 7) for the preparation of Compound 7 is shown below. The synthesis proceeds through the intermediates indicated (Compounds 42 and 44). The yield for each synthetic step was as indicated.

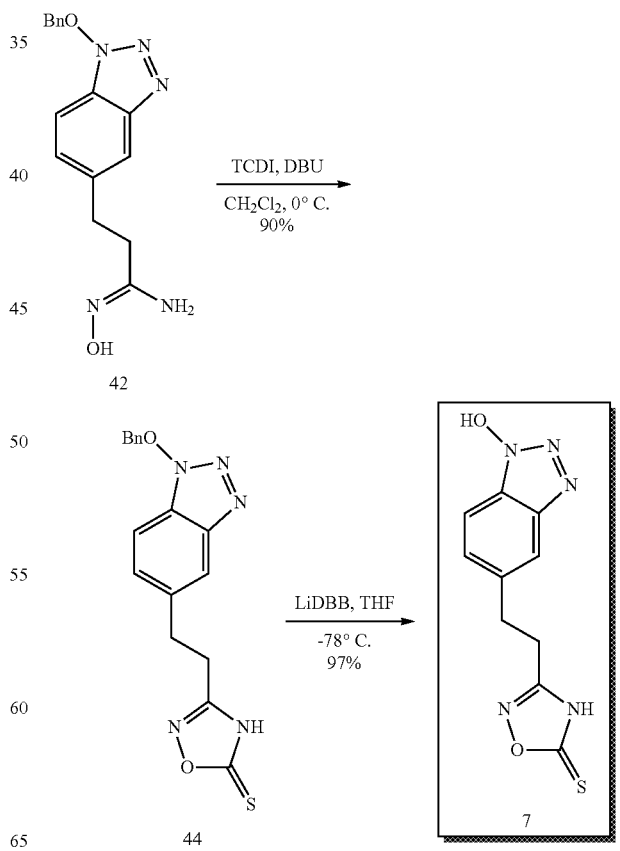

a. Preparation of 3-(2-(1-(benzyloxy)-1H-benzo[d][1,2,3]triazol-5-yl)ethyl)-1,2,4-oxadiazole-5(4H)-thione (Compound 44).

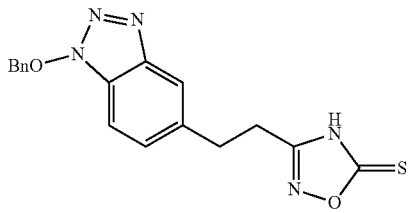 [SMILES: S=c1[nH]c(CCc2ccc3c(c2)nnn3OCc2ccccc2)no1]

The procedure used to prepare 44 was the same as that used to prepare 36 except 42 was used (220 mg, 0.71 mmol) instead of 34, afforded the desired product, 44, as a white solid (168 mg, 90% yield). mp 166-167° C. $^1$H NMR (500 MHz, DMSO) δ 7.84 (s, 1H), 7.45 (m, 3H), 7.37 (m, 4H), 5.56 (s, 2H), 3.09 (t, J=7.5, 2H), 2.99 (t, J=7.5, 2H). $^{13}$C NMR (125 MHz, DMSO) δ 187.44, 161.19, 143.68, 137.19, 134.00, 130.84, 130.81, 130.26, 129.30, 127.04, 118.92, 109.95, 31.14, 25.65. HRMS (ESI) m/z calcd. for $C_{17}H_{14}N_5O_2S$ [M–H]$^-$ 352.0868, found 352.0883.

b. Preparation of 3-(2-(1-hydroxy-1H-benzo[d][1,2,3]triazol-5-yl)ethyl)-1,2,4-oxadiazole-5(4H)-thione (Compound 7).

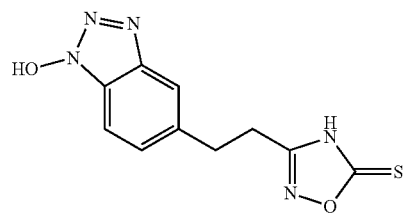 [SMILES: On1nnc2cc(CCc3noc(=S)[nH]3)ccc21]

The procedure used to prepare 7 is the same as that to prepare 36 except 44 was used (84 mg, 0.24 mmol) instead of 35, afforded the desired product, 7, as a white solid (61 mg, 97% yield). mp 190-193° C. $^1$H NMR (500 MHz, DMSO) δ 7.81 (s, 1H), 7.66 (d, J=8.5 Hz, 1H), 7.43 (d, J=8.5 Hz, 1H), 3.13 (t, J=7.5, 2H), 3.03 (t, J=7.5, 2H). $^{13}$C NMR (125 MHz, DMSO) δ 187.13, 160.98, 143.42, 130.58, 129.04, 127.28, 118.19, 110.11, 31.07, 25.50. HRMS (ESI) m/z calcd. for $C_{10}H_8N_5O_2S$ [M–H]$^-$ 262.0399, found 262.0417.

9. Preparation of 5-((2H-tetrazol-5-yl)methoxy)-1H-benzo[d][1,2,3]triazol-1-ol (Compound 8)

The overall synthesis scheme (Synthesis Scheme 8) for the preparation of Compound 8 is shown below. The synthesis proceeds through the intermediates indicated (Compounds 45, 46, 47 and 48). The yield for each synthetic step was as indicated.

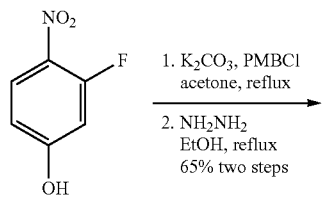

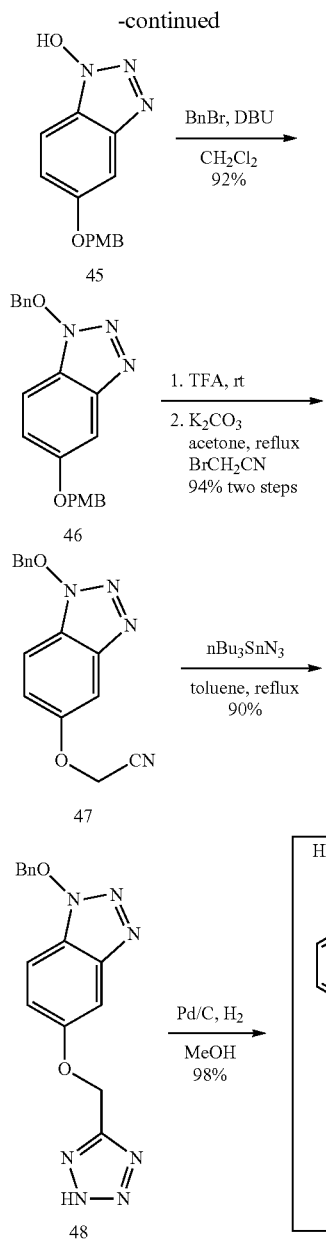

a. Preparation of 5-((4-methoxybenzyl)oxy)-1H-benzo[d][1,2,3]triazol-1-ol (Compound 45).

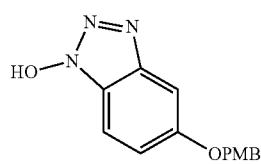

A mixture of phenol (5.0 g, 31.8 mmol), K$_2$CO$_3$ (13.0 mg, 95.5 mmol), and 2-bromoacetonitrile (5.7 mg, 36.6 mmol) in acetone (100 mL) was refluxed for 8 h and then was allowed to cool to room temperature. The reaction was filtered, and the residue washed with acetone. The combined filtrate and washings were concentrated in vacuo. The residue was purified by column chromatography (silica gel, hexanes: EtOAc=5:1) to yield nitrobenzene (7.5 g, 85% yield) as pale yellow solid: mp 119-120° C. To a solution of nitrobenzene (1.20 g, 4.33 mmol) in EtOH (50 mL) was added 65% hydrazine hydrate (1.92 g, 39.0 mmol, 9 equiv.). The mixture was stirred under reflux for 24 h, and then the solvent was removed by rotary evaporation. The residue was taken in 50 mL of cold water and acidified with HCl 1.5 M to pH 4. The product precipitated and was isolated by filtration. Drying under high vacuum at 40° C. gave the desired product, 45, (0.89 g, 76% yield) as a white solid.

b. Preparation of 1-(benzyloxy)-5-((4-methoxybenzyl)oxy)-1H-benzo[d][1,2,3]triazole (Compound 46).

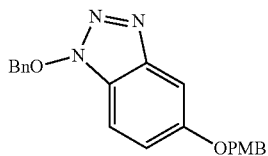

Benzyl bromide (107 mg, 0.63 mmol) was added dropwise to an ice-cooled mixture of 45 (154 mg, 0.57 mmol) and DBU (104 mg, 0.68 mmol) in $CH_2Cl_2$ (10 mL). The resulting mixture was stirred at rt for 30 min, diluted with water, and extracted with EtOAc (10 mL×2). The extract was washed with water and brine, and dried over $Na_2SO_4$. The solvent was evaporated in vacuo. The residue was purified by column chromatography (silica gel, hexanes:EtOAc=3:1) to yield 46 (189 mg, 92% yield) as a pale yellow solid: mp 99-101° C.

c. Preparation of 2-((1-(benzyloxy)-1H-benzo[d][1,2,3]triazol-5-yl)oxy)acetonitrile (Compound 47).

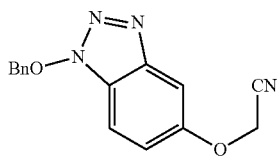 [SMILES: N#CCOc1ccc2c(c1)nnn2OCc1ccccc1]

To a solution of 46 (122 mg, 0.34 mmol) in dry $CH_2Cl_2$ (1 mL) at 0° C. was added TFA (2 mL). The resulting mixture was stirred for 2 h. The reaction mixture was concentrated and the residue was directly purified by column chromatography (silica gel, hexanes:EtOAc=3:1) to yield phenol (78 mg, 94% yield) as viscous yellow oil. A mixture of phenol (78 mg, 0.32 mmol), $K_2CO_3$ (133 mg, 0.96 mmol), and 2-bromoacetonitrile (58 mg, 0.48 mmol) in acetone (25 mL) was refluxed for 8 h and then was allowed to cool to room temperature. The reaction was filtered, and the residue washed with acetone. The combined filtrate and washings were concentrated in vacuo. The residue was purified by column chromatography (silica gel, hexanes:EtOAc=3:1) to yield 47 (89 mg, 99% yield) as a yellow oil.

d. Preparation of 5-((2H-tetrazol-5-yl)methoxy)-1-(benzyloxy)-1H-benzo[d][1,2,3]triazole (Compound 48).

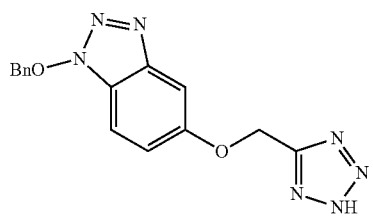 [SMILES: c1ccc(COn2nnc3cc(OCc4nn[nH]n4)ccc32)cc1]

The procedure used to prepare 48 was the same as that used to prepare 33 except 47 was used (70 mg, 0.25 mmol) instead of 32, afforded the desired product, 48, as a white solid (73 mg, 90% yield). mp 162-164° C. mp 162-164° C. $^1$H NMR (300 MHz, DMSO) δ 7.60 (d, J=2.1 Hz, 2H), 7.42 (m, 3H), 7.34 (m, 3H), 5.54 (m, 2H).

e. Preparation of 5-((2H-tetrazol-5-yl)methoxy)-1H-benzo[d][1,2,3]triazol-1-ol (Compound 8)

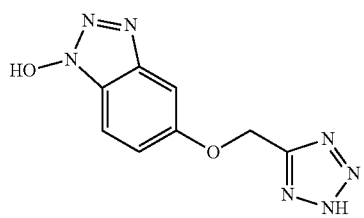 [SMILES: On1nnc2cc(OCc3nn[nH]n3)ccc21]

The procedure used to prepare 8 was the same as that used to prepare 1 except 48 was used (73 mg, 0.23 mmol) instead of 33, afforded the desired product, 8, as a white solid (51 mg, 98% yield). $^1$H NMR (300 MHz, DMSO) δ 7.67 (d, J=9.0 Hz, 1H), 7.58 (s, 1H), 7.26 (dd, J=9.0, 2.1 Hz, 1H), 5.59 (s, 2H). $^1$H NMR (300 MHz, DMSO) δ 7.67 (d, J=9.0 Hz, 1H), 7.58 (s, 1H), 7.26 (dd, J=9.0, 2.1 Hz, 1H), 5.59 (s, 2H). $^{13}$C NMR (75 MHz, DMSO) δ 155.88, 154.07, 124.51, 120.63, 111.56, 100.41, 60.55. HRMS (ESI) m/z calcd. for $C_8H_7N_7O_2Na$ [M+Na]$^+$ 256.0559, found 256.0563.

10. Preparation of 5-((2H-tetrazol-5-yl)methyl)-1H-indazol-1-ol (Compound 9)

The overall synthesis scheme (Synthesis Scheme 9) for the preparation of Compound 9 is shown below. The synthesis proceeds through the intermediates indicated (Compounds 49, 50, 51, 52 and 53). The yield for each synthetic step was as indicated.

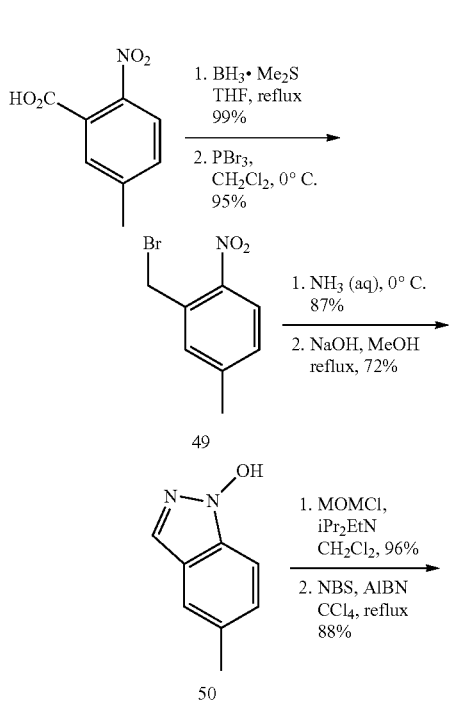

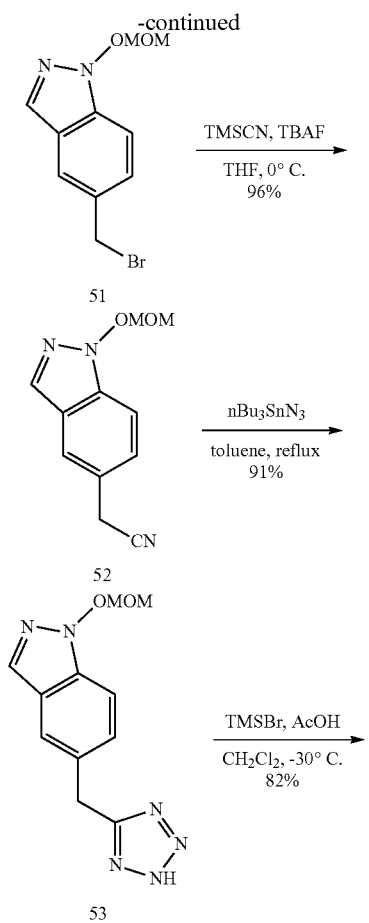

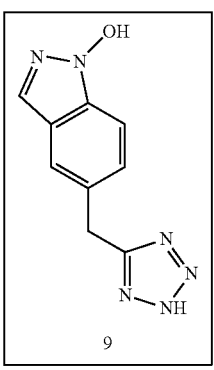

a. Preparation of 2-(bromomethyl)-4-methyl-1-nitrobenzene (Compound 49)

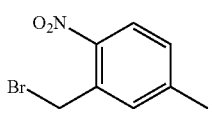

5-methyl-2-nitrobenzoic acid (10.0 g, 55.2 mmol) were dissolved in THF (100 mL) followed by dropping 2.0 M borane dimethlsulfide complex (110 mL, 221.1 mmol) and heating at 80° C. After 1.5 hours, 100 ml of 1 M HCl were dropped into this reaction system while cooling with ice and stirring. The system was extracted with ethyl acetate, and then was dried with Na2SO4 followed by concentration under reduced pressure and drying to obtain benzylic alcohol (9.1 g, 99% yield) as viscous colorless oil. (5-methyl-2-nitrophenyl) methanol (9.1 g, 54.5 mmol) were dissolved in dry $CH_2Cl_2$ (100 mL) followed by the addition of phosphorous tribromide (7.4 g, 27.3 mmol) and stirring at room temperature. After 30 minutes, saturated $NaHCO_3$ (aq. 100 mL) were added followed by stirring for 10 minutes and extracting with $CH_2Cl_2$ (200 ml×2). The organic phase was then concentrated under reduced pressure and dried to obtain the benzyl bromide analogue, 49, (11.9 g, 95% yield) as a white solid: mp 51-52° C.

b. Preparation of 5-methyl-1H-indazol-1-ol (Compound 50)

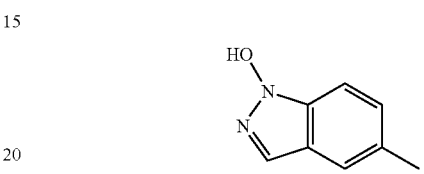

An aqueous solution of 25% w/v ammonia (100 mL) was treated with EtOH (200 mL) and cooled to −78° C. The mixture was slowly treated with a cooled (−78° C.) solution of the benzylbromide 49 (2.3 g, 10.0 mmol) in ethanol (100 mL). The mixture was then allowed to come to room temperature and stirred for 48 h. The mixtures were evaporated under reduced pressure and the residue solid was washed with $CH_2Cl_2$ afford 2-nitrobenzylamine (1.45 g, 87% yield) as white solid: mp 51-52° C. The 2-nitrobenzylamine (1.45 g, 8.73 mmol) was treated with a 1M methanolic solution of sodium hydroxide (20 mL) and heated at 80° C. overnight. The mixture was concentrated and $H_2O$ (50 mL) was added. The aqueous phase was washed with EtOAc (10 mL×2) and then was acidified with 1 N HCl to PH to 4. The aqueous phase was exacted with EtOAc (20 mL×2) and then was dried over $Na_2SO_4$ and concentrated to provide the product 50 (930 mg, 72% yield) as a pink solid.

c. Preparation of 5-(bromomethyl)-1-(methoxymethoxy)-1H-indazole (Compound 51)

To a solution of 50 (465 mg, 3.16 mmol) in $CH_2Cl_2$ (10 mL) at ° C., N,N-diisopropylethylamine (490 mg, 3.79 mmol) and MOMCl (293 mg, 3.64 mmol) were added, and the reaction solution was warmed to room temperature and stirred for an additional 1 h. After that, the mixture was diluted with water and extracted with EtOAc (10 mL×2). The extract was washed with water and brine, and dried over $Na_2SO_4$. The solvent was evaporated in vacuo. The residue was purified by column chromatography (silica gel, hexanes:EtOAc=4:1) to indazol ether (449 mg, 96%) as colorless oil. A solution of indazol ether (569 mg, 2.98 mmol) in $CCl_4$ (20 mL) was heated to reflux after which N-bromosuccinimide (679 mg, 3.43 mol) and AIBN (49 mg, 0.298 mol) were carefully added in a portionwise manner over 5 min. After 3 h the mixture was cooled to rt and the succinimide which resulted was filtered off and washed with $CCl_4$ (5 mL×3). The solvent was removed under reduced pressure and purified by column chromatography (silica gel hexanes:EtOAc=6:1) to give the desired product 51 (2.9 g, 9.1 mmol, 68% yield) as a viscous colorless oil.

d. Preparation of 2-(1-(methoxymethoxy)-1H-indazol-5-yl)acetonitrile (Compound 52)

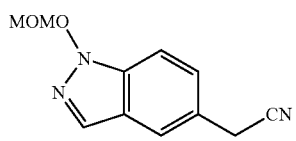

To a solution of 51 (823 mg, 3.05 mmol) in THF (5 mL), 1M TBAF (6.1 mL, 6.10 mmol) and TMSCN (605 mg, 0.728 mmol) was added at 0° C. The reaction mixture was stirred at room temperature for 1 h. The solvent was evaporated in vacuo. The residue was purified by column chromatography (silica gel hexanes:EtOAc=2:1) to give the desired product 52 (635 mg, 96% yield) as a viscous yellow oil.

e. Preparation of 5-((2H-tetrazol-5-yl)methyl)-1-(methoxymethoxy)-1H-indazole (Compound 53)

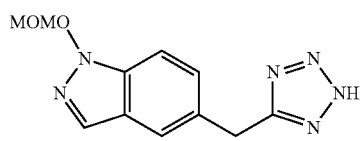

The procedure used to prepare 53 was the same as that used to prepare 33 except 52 was used (261 mg, 1.20 mmol) instead of 32, afforded the desired product, 53, as a viscous colorless oil (51 mg, 91% yield). $^1$H NMR (500 MHz, CDCl$_3$) δ 7.44 (s, 1H), 7.39 (d, J=8.6 Hz, 1H), 7.31 (s, 1H), 7.25 (m, 1H), 5.26 (s, 2H), 4.39 (s, 2H). $^{13}$C NMR (125 MHz, CDCl$_3$) δ 156.16, 134.62, 128.71, 127.90, 127.55, 121.29, 121.13, 109.43, 102.47, 57.99, 30.01. HRMS (ESI) m/z calcd. for $C_{11}H_{12}N_6O_2Na$ [M+Na]$^+$ 283.0919, found 283.0914.

f. Preparation of 5-((2H-tetrazol-5-yl)methyl)-1H-indazol-1-ol (Compound 9)

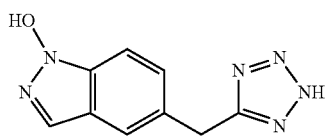 [SMILES: On1ncc2cc(Cc3nn[nH]n3)ccc21]

To a solution of 53 (136 mg, 0.52 mmol) in dry CH$_2$Cl$_2$ (2 mL) and AcOH (0.2 mL) at −30° C. was added TMSBr (398 mg, 2.6 mmol). The resulting mixture was stirred for 2 h, and the temperature was allowed to rise to 0° C. The reaction was quenched with saturated NH4Cl, and the mixture was diluted with EtOAc, washed with water and brine, and then dried over Na$_2$SO$_4$. The product was purified by chromatography (silica gel CH$_2$Cl$_2$:MeOH=10:1) to give 9 (92 mg, 82% yield) as a pale red solid. $^1$H NMR (500 MHz, DMSO) δ 12.24 (br, 1H), 7.75 (s, 1H), 7.59 (s, 1H), 7.47 (d, J=8.6 Hz, 1H), 7.27 (dd, J=1.0 Hz, 1H), 4.37 (s, 3H). $^{13}$C NMR (125 MHz, DMSO) δ 172.72, 133.96, 128.89, 128.18, 126.05, 121.68, 121.01, 109.76, 29.43. HRMS (ESI) m/z calcd. for $C_9H_7N_6O$ [M−H]$^-$ 215.0681, found 215.0688.

11. Preparation of 3-((1-hydroxy-1H-indazol-5-yl)methyl)-1,2,4-oxadiazol-5(4H)-one (Compound 10).

The overall synthesis scheme (Synthesis Scheme 10) for the preparation of Compound 10 is shown below. The synthesis proceeds through the intermediates indicated (Compounds 52, 54, and 55). The yield for each synthetic step was as indicated.

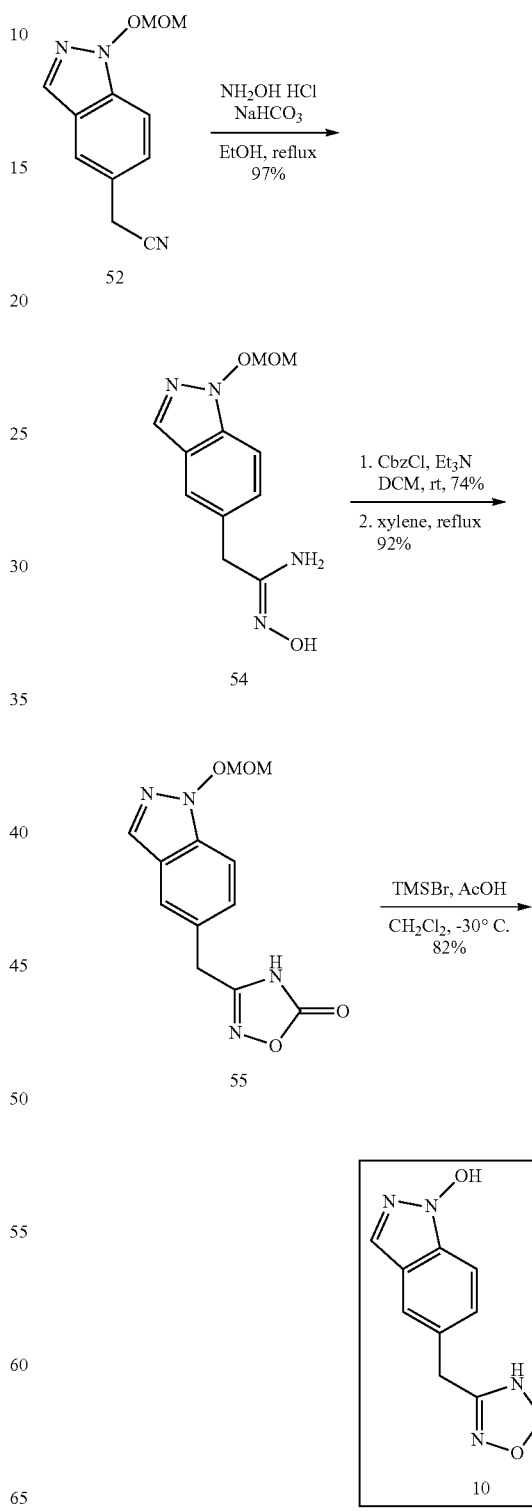

a. Preparation of (Z)—N'-hydroxy-2-(1-(methoxymethoxy)-1H-indazol-5-yl)acetimidamide (Compound 54).

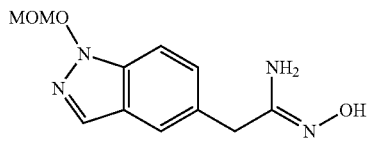

The procedure used to prepare 54 was the same as that used to prepare 34 except 52 was used (456 mg, 2.10 mmol) instead of 32, afforded the desired product, 54, as a colorless viscous oil (499 mg, 95% yield).

b. Preparation of 3-((1-(methoxymethoxy)-1H-indazol-5-yl)methyl)-1,2,4-oxadiazol-5(4H)-one (Compound 55).

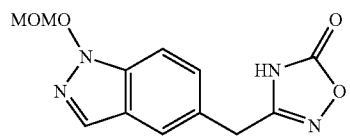

The procedure used to prepare 55 was the same as that used to prepare 35 except 54 was used (210 mg, 0.84 mmol) instead of 34, afforded the desired product, 55, as a pale yellow viscous oil (158 mg, 68% yield for two steps). $^1$H NMR (300 MHz, CDCl$_3$) δ 10.44 (br, 1H), 7.55 (s, 1H), 7.49 (s, 1H), 7.44 (d, J=8.7 Hz, 1H), 7.26 (dd, J=8.7, 1.5 Hz, 2H), 5.31 (s, 2H), 3.93 (s, 2H), 3.64 (s, 3H). $^{13}$C NMR (75 MHz, CDCl$_3$) δ 160.83, 158.36, 134.80, 127.94, 127.82, 125.55, 121.53, 121.30, 109.49, 102.28, 57.88, 31.34. HRMS (ESI) m/z calcd. for C$_{12}$H$_{12}$N$_4$O$_4$Na [M+Na]$^+$ 299.0756, found 299.0754.

c. Preparation of 3-((1-hydroxy-1H-indazol-5-yl)methyl)-1,2,4-oxadiazol-5(4H)-one (Compound 10).

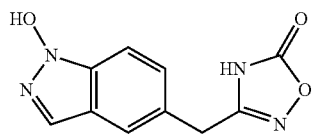 [SMILES: O=c1[nH]c(Cc2ccc3c(cnn3O)c2)no1]

The procedure used to prepare 10 is the same as that to prepare 9 except 55 was used (110 mg, 0.40 mmol) instead of 53, afforded the desired product, 10, as a pale yellow solid (76 mg, 82% yield). $^1$H NMR (500 MHz, DMSO) δ 12.28 (br, 1H), 7.78 (s, 1H), 7.65 (s, 1H), 7.49 (d, J=8.6 Hz, 1H), 7.31 (dd, J=8.6, 1.4 Hz, 1H), 3.97 (s, 2H). $^{13}$C NMR (125 MHz, DMSO) δ 159.91, 159.45, 133.37, 127.48, 126.04, 125.38, 120.95, 120.75, 109.00, 30.54. HRMS (ESI) m/z calcd. for C$_{10}$H$_7$N$_4$O$_3$[M−H]$^-$ 231.0518, found 231.0553.

12. Preparation of 3-((1-hydroxy-1H-indazol-5-yl)methyl)-1,2,4-oxadiazole-5(4H)-thione (Compound 11).

The overall synthesis scheme (Synthesis Scheme 11) for the preparation of Compound 11 is shown below. The synthesis proceeds through the intermediates indicated (Compounds 54 and 56). The yield for each synthetic step was as indicated.

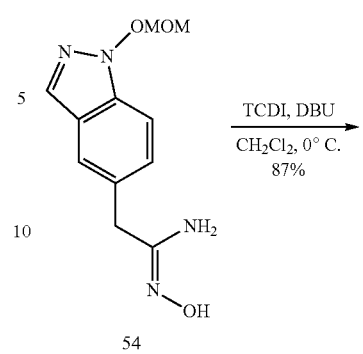

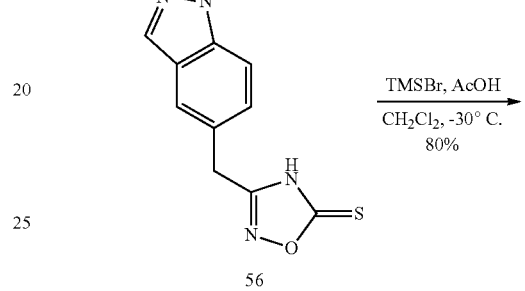

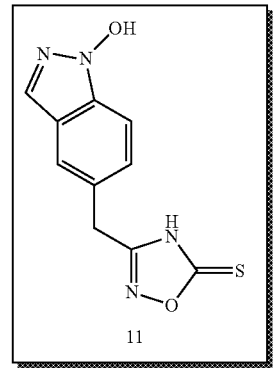

a. Preparation of 3-((1-(methoxymethoxy)-1H-indazol-5-yl)methyl)-1,2,4-oxadiazole-5(4H)-thione (Compound 56).

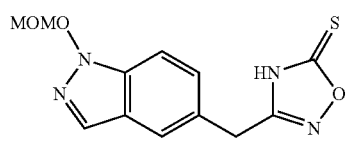

The procedure used to prepare 56 was the same as that used to prepare 36 except 54 was used (400 mg, 1.60 mmol) instead of 34, afforded the desired product, 56, as a pale yellow solid (406 mg, 87% yield), mp 136-138° C. $^1$H NMR (500 MHz, DMSO) δ 7.95 (s, 1H), 7.72 (s, 1H), 7.61 (d, J=8.6 Hz, 1H), 7.40 (dd, J=8.7, 1.4 Hz, 1H), 5.35 (s, 3H), 4.13 (s, 2H), 3.59 (s, 3H). $^{13}$C NMR (125 MHz, DMSO) δ 187.79, 161.63, 134.91, 129.16, 128.58, 127.41, 121.97, 121.94, 109.68, 102.35, 57.89, 29.89. HRMS (ESI) m/z calcd. for C$_{12}$H$_{11}$N$_4$O$_3$S [M−H]$^-$ 291.0552, found 291.0562.

b. Preparation of 3-((1-hydroxy-1H-indazol-5-yl)methyl)-1,2,4-oxadiazole-5(4H)-thione (Compound 11).

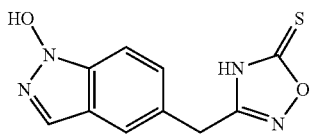

The procedure used to prepare 11 was the same as that used to prepare 9 except 56 was used (64 mg, 0.22 mmol) instead of 53, afforded the desired product, 11, as a pale yellow solid (44 mg, 80% yield). $^1$H NMR (500 MHz, DMSO) δ 12.27 (br, 1H), 7.77 (s, 1H), 7.65 (s, 1H), 7.48 (d, J=8.0 Hz, 1H), 7.40 (dd, J=8.0, 1.5 Hz, 1H), 4.09 (s, 2H). $^{13}$C NMR (125 MHz, DMSO) δ 187.81, 161.58, 134.08, 128.24, 126.48, 126.13, 121.66, 121.62, 109.75, 29.93. HRMS (ESI) m/z calcd. for $C_{10}H_7N_4O_2S$ [M−H]$^-$ 247.0290, found 247.0297.

13. Preparation of 5-(2-(2H-tetrazol-5-yl)ethyl)-1H-indazol-1-ol (Compound 12).

The overall synthesis scheme (Synthesis Scheme 12) for the preparation of Compound 12 is shown below. The synthesis proceeds through the intermediates indicated (Compounds 51, 57, and 58). The yield for each synthetic step was as indicated.

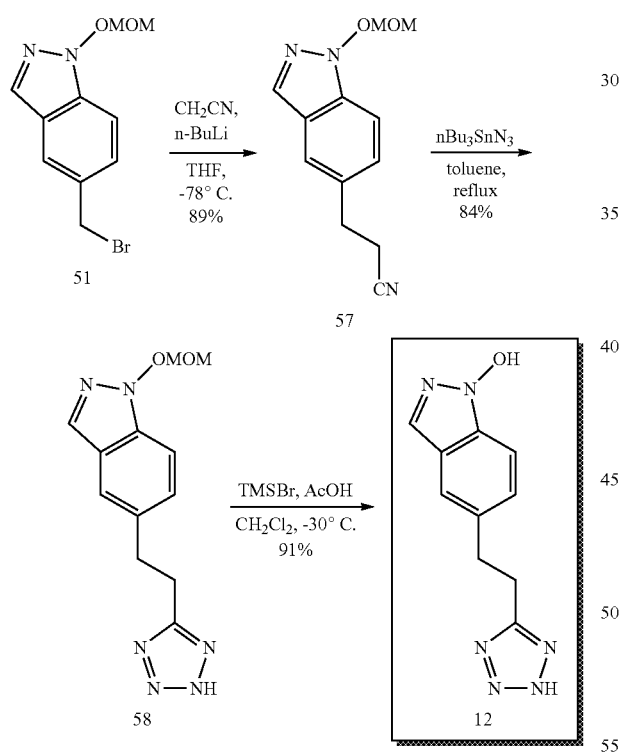

a. Preparation of 3-(1-(methoxymethoxy)-1H-indazol-5-yl)propanenitrile (Compound 57).

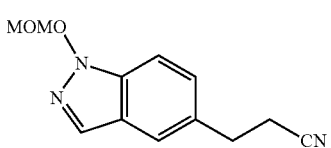

The procedure used to prepare 57 was the same as that used to prepare 40 except 51 was used (530 mg, 1.96 mmol) instead of 31, afforded the desired product, 57, as a colorless oil (403 mg, 89% yield).

b. Preparation of 5-(2-(2H-tetrazol-5-yl)ethyl)-1-(methoxymethoxy)-1H-indazole (Compound 58).

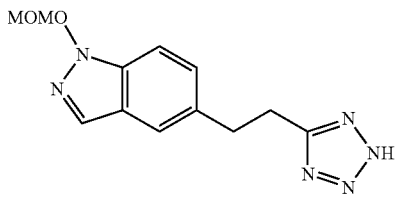

The procedure used to prepare 58 was the same as that used to prepare 33 except 57 was used (159 mg, 0.69 mmol) instead of 32, afforded the desired product, 58, as a colorless viscous oil (159 mg, 84% yield). $^1$H NMR (500 MHz, CDCl$_3$) δ 7.58 (s, 1H), 7.40 (s, 1H), 7.35 (d, J=8.6 Hz, 1H), 7.17 (d, J=8.6 Hz, 1H), 5.28 (s, 2H), 3.61 (s, 3H), 3.35 (t, J=7.5 Hz, 3H), 3.21 (t, J=7.4 Hz, 2H). $^{13}$C NMR (125 MHz, CDCl$_3$) δ 156.33, 134.61, 132.83, 128.47, 127.76, 121.69, 120.00, 108.88, 102.16, 57.84, 33.71, 25.88. HRMS (ESI) m/z calcd. for $C_{12}H_{14}N_6O_2Na$ [M+Na]$^+$ 297.1076, found 297.1073.

c. Preparation of 5-(2-(2H-tetrazol-5-yl)ethyl)-1H-indazol-1-ol (Compound 12).

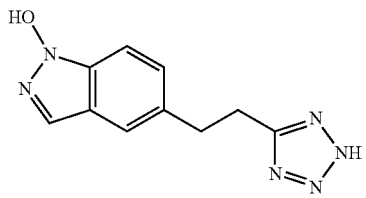 [SMILES: On1ncc2cc(CCc3nn[nH]n3)ccc21]

The procedure used to prepare 12 was the same as that used to prepare 9 except 58 was used (159 mg, 0.69 mmol) instead of 53, afforded the desired product, 12, as a colorless viscous oil (159 mg, 84% yield). $^1$H NMR (500 MHz, CDCl$_3$) δ 7.69 (s, 1H), 7.49 (s, 1H), 7.41 (d, J=9.0 Hz, 1H), 7.25 (d, J=9.0 Hz, 1H), 3.22 (t, J=7.4 Hz, 3H), 3.13 (t, J=7.4 Hz, 2H). $^{13}$C NMR (125 MHz, CDCl$_3$) δ 156.07, 133.85, 132.97, 128.14, 125.70, 121.69, 120.04, 109.35, 33.36, 25.71. HRMS (ESI) m/z calcd. for $C_{10}H_9N_6O$ [M−H]$^-$ 229.0838, found 229.0850.

14. Preparation of 3-(2-(1-hydroxy-1H-indazol-5-yl)ethyl)-1,2,4-oxadiazol-5(4H)-one (Compound 13).

The overall synthesis scheme (Synthesis Scheme 13) for the preparation of Compound 13 is shown below. The synthesis proceeds through the intermediates indicated (Compounds 57, 59, and 60). The yield for each synthetic step was as indicated.

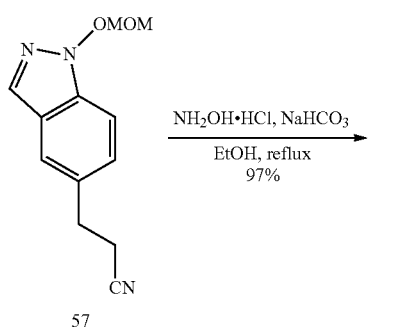

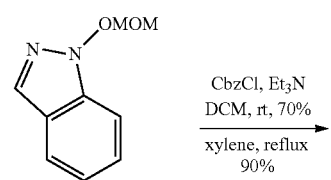

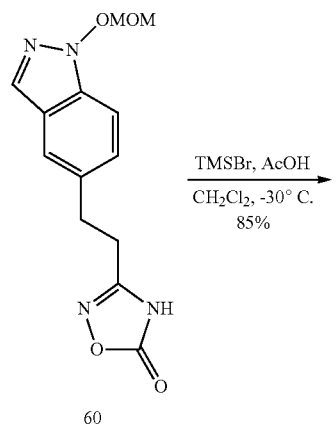

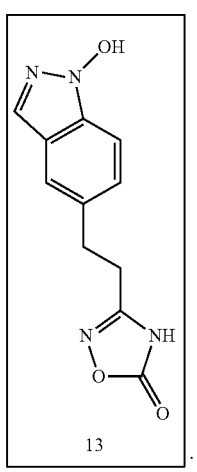

a. Preparation of (Z)—N'-hydroxy-3-(1-(methoxymethoxy)-1H-indazol-5-yl)propanimidamide (Compound 59).

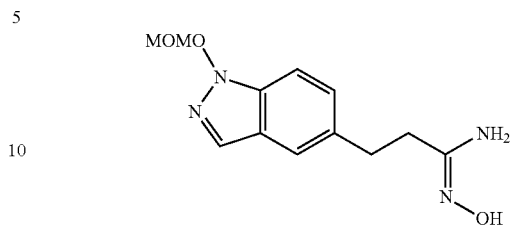

The procedure used to prepare 46 was the same as that used to prepare 34 except 57 was used (286 mg, 1.24 mmol) instead of 32, afforded the desired product, 46, as a colorless viscous oil (318 mg, 97% yield).

b. Preparation of 3-(2-(1-(methoxymethoxy)-1H-indazol-5-yl)ethyl)-1,2,4-oxadiazol-5(4H)-one (Compound 60).

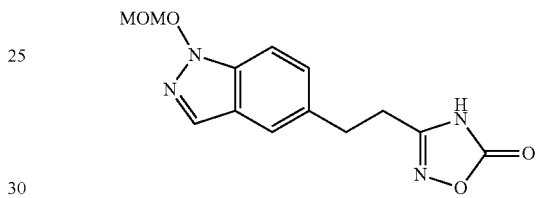

The procedure used to prepare 60 was the same as that used to prepare 35 except 59 was used (185 mg, 0.7 mmol) instead of 34, afforded the desired product, 60, as a pale yellow viscous oil (128 mg, 63% yield for two steps). $^1$H NMR (500 MHz, CDCl$_3$) δ 7.70 (s, 1H), 7.48 (s, 1H), 7.45 (d, J=8.6 Hz, 1H), 7.26 (dd, J=8.6, 1.5 Hz, 1H), 5.33 (s, 2H), 3.65 (s, 3H), 3.10 (t, J=7.7 Hz, 2H), 2.91 (t, J=7.7 Hz, 2H). $^{13}$C NMR (125 MHz, CDCl$_3$) δ 169.90, 161.22, 158.51, 134.70, 131.97, 128.03, 127.85, 121.85, 120.01, 109.10, 102.12, 57.84, 31.48, 27.19. HRMS (ESI) m/z calcd. for C$_{13}$H$_{14}$N$_4$O$_4$Na [M+Na]$^+$ 313.0913, found 313.0917.

c. Preparation of 3-(2-(1-hydroxy-1H-indazol-5-yl)ethyl)-1,2,4-oxadiazol-5(4H)-one (Compound 13).

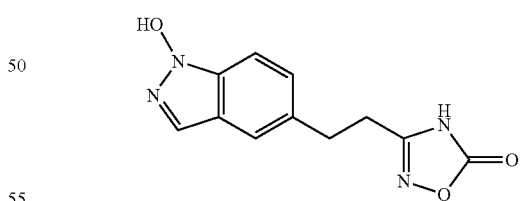

The procedure used to prepare 13 was the same as that used to prepare 9 except 60 was used (230 mg, 0.79 mmol) instead of 53, afforded the desired product, 13, as a pale yellow solid (165 mg, 85% yield). $^1$H NMR (500 MHz, DMSO) δ 12.19 (br, 1H), 7.72 (s, 1H), 7.53 (s, 1H), 7.45 (d, J=8.6 Hz, 1H), 7.28 (d, J=8.6 Hz, 1H), 3.02 (t, J=7.6 Hz, 3H), 2.84 (t, J=7.6 Hz, 3H). $^{13}$C NMR (125 MHz, DMSO) δ 160.43, 159.97, 133.90, 132.58, 128.11, 125.77, 121.72, 120.10, 109.45, 31.28, 27.36. HRMS (ESI) m/z calcd. for C$_{11}$H$_9$N$_4$O$_3$[M−H]$^-$ 245.0675, found 245.0680.

15. Preparation of 3-(2-(1-hydroxy-1H-indazol-5-yl)ethyl)-1,2,4-oxadiazole-5(4H)-thione (Compound 14)

The overall synthesis scheme (Synthesis Scheme 14) for the preparation of Compound 14 is shown below. The synthesis proceeds through the intermediates indicated (Compounds 59 and 61). The yield for each synthetic step was as indicated.

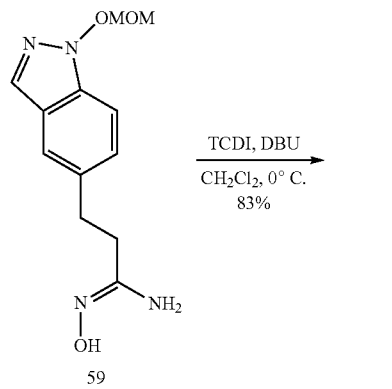

The procedure used to prepare 61 was the same as that used to prepare 36 except that 59 was used (94 mg, 0.37 mmol) instead of 34, afforded the desired product, 61, as a pale yellow viscous oil (90 mg, 83% yield). $^1$H NMR (500 MHz, acetone) δ 7.78 (s, 1H), 7.63 (s, 1H), 7.57 (d, J=8.5 Hz, 1H), 7.39 (dd, J=8.5, 1.5 Hz, 1H), 5.36 (s, 2H), 3.65 (s, 3H), 3.30 (t, J=7.7 Hz, 2H), 3.16 (t, J=7.7 Hz, 2H). $^{13}$C NMR (125 MHz, acetone) δ 189.8, 168.06, 128.43, 128.35, 127.57, 122.28, 120.17, 120.00, 109.06, 101.95, 57.17, 31.51, 27.17. HRMS (ESI) m/z calcd. for $C_{13}H_{13}N_4O_3S$ [M−H]$^−$ 305.0708, found 305.0714.

b. Preparation of 3-(2-(1-hydroxy-1H-indazol-5-yl)ethyl)-1,2,4-oxadiazole-5(4H)-thione (Compound 14).

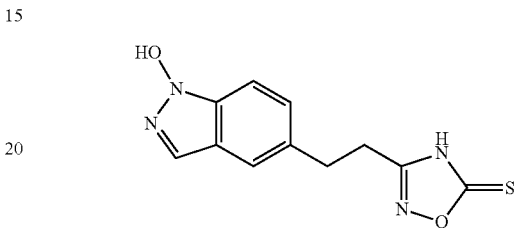

The procedure used to prepare 14 is the same as that to used prepare 9 except using 61 (85 mg, 0.28 mmol) instead of 53, afforded the desired product, 14, as a pale yellow solid (56 mg, 83% yield). $^1$H NMR (500 MHz, DMSO) δ 12.19 (br, 1H), 7.72 (s, 1H), 7.53 (s, 1H), 7.45 (d, J=8.5 Hz, 1H), 7.27 (dd, J=8.5, 1.5 Hz, 1H), 3.04 (t, J=7.5 Hz, 2H), 2.93 (t, J=7.5 Hz, 2H). $^{13}$C NMR (125 MHz, DMSO) δ 188.23, 162.39, 132.69, 128.12, 127.67, 125.76, 121.70, 120.08, 109.43, 31.66, 26.45. HRMS (ESI) m/z calcd. for $C_{11}H_9N_4O_2S$ [M−H]$^−$ 261.0446, found 261.0450.

16. Preparation of 5-(((1H-tetrazol-5-yl)methoxy)methyl)-1H-indazol-1-ol (Compound 15).

The overall synthesis scheme (Synthesis Scheme 15) for the preparation of Compound 15 is shown below. The synthesis proceeds through the intermediates indicated (Compounds 25a and 49). The yield for each synthetic step was as indicated.

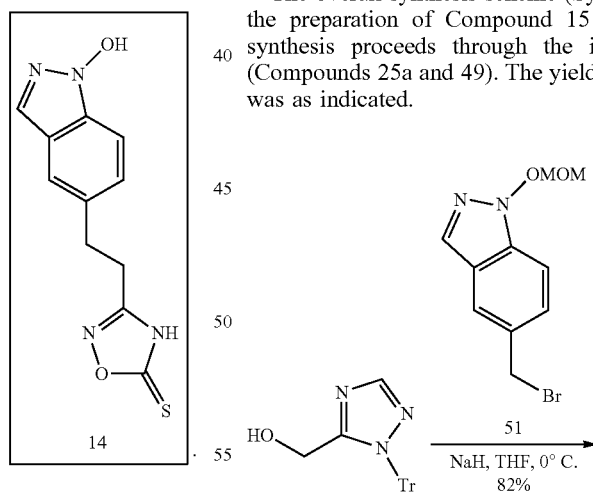

a. Preparation of 3-(2-(1-(methoxymethoxy)-1H-indazol-5-yl)ethyl)-1,2,4-oxadiazole-5(4H)-thione (Compound 61).

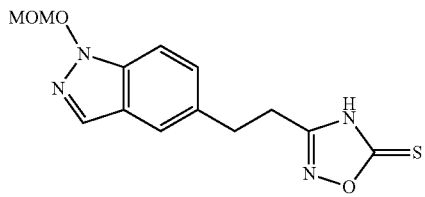

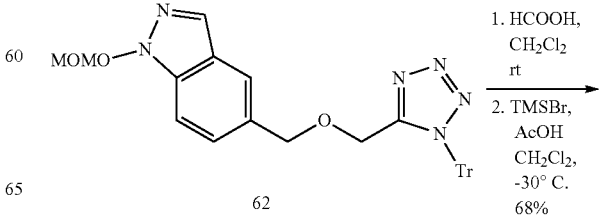

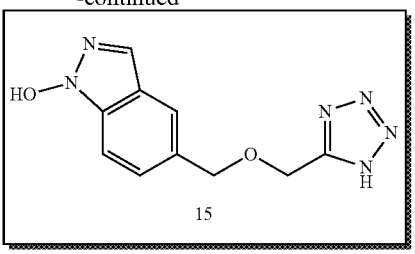

a. Preparation of 1-(methoxymethoxy)-5-(((1-trityl-1H-tetrazol-5-yl)methoxy)methyl)-1H-indazole (Compound 62).

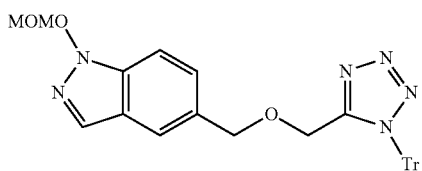

The procedure used to prepare 62 was the same as that used to prepare 39 except 51 was used (315 mg, 1.17 mmol) instead of 31, afforded the desired product, 62, as a colorless viscous oil (511 mg, 82% yield).

b. Preparation of 5-(((1H-tetrazol-5-yl)methoxy)methyl)-1H-indazol-1-ol (Compound 15).

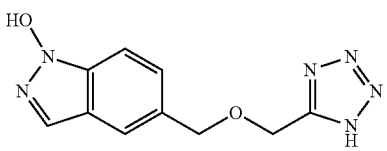 [SMILES: On1ncc2cc(COCc3nnn[nH]3)ccc21]

The procedure used to prepare 15 was the same as that used to prepare 4 except 62 was used (265 mg, 0.50 mmol) instead of 39, afforded the desired product, as a pale yellow solid (84 mg, 68% yield for two steps). $^1$H NMR (300 MHz, DMSO) δ 8.07 (s, 1H), 7.76 (s, 1H), 7.53 (d, J=8.4 Hz, 1H), 7.36 (d, J=8.4 Hz, 1H), 4.85 (s, 2H), 4.67 (s, 2H). $^{13}$C NMR (75 MHz, DMSO) δ 154.51, 140.24, 134.21, 129.74, 127.39, 123.31, 120.85, 110.81, 73.26, 60.94. HRMS (ESI) m/z calcd. for $C_{10}H_9N_6O_2[M-H]^-$ 245.0787, found 245.0801.

17. Preparation of 5-(2-(2H-tetrazol-5-yl)ethyl)-1H-indazole (Compound 16).

The overall synthesis scheme (Synthesis Scheme 16) for the preparation of Compound 16 is shown below. The synthesis proceeds through the intermediates indicated (Compounds 63, 64, 65, 66, 67, 68, and 69). The yield for each synthetic step was as indicated.

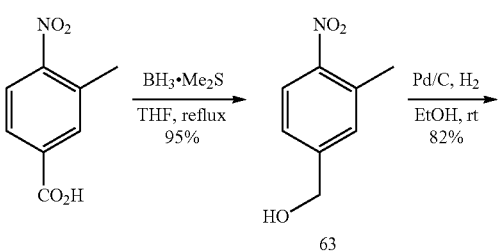

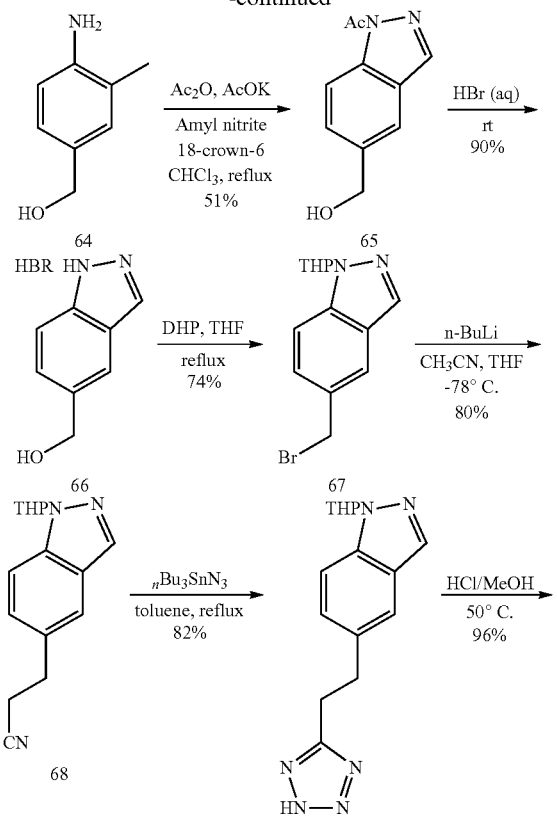

a. Preparation of 5-(bromomethyl)-1-(tetrahydro-2H-pyran-2-yl)-1H-indazole (Compound 67).

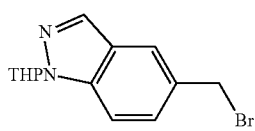

Compound 66 was prepared as previously described (Sun, J.-H., Teleha, C. A., Yan, J.-S., et al. *J. Org. Chem.* 62 (1997) 5627-5629). A mixture of 66 (880 mg, 3.03 mmol) and 3,4-dihydro-2H-pyran (511 g, 6.07 mmol) in THF (20 mL) was refluxed for 2 h, and then stirred overnight at room temperature. The reaction solution was diluted with 20 mL of $CH_2Cl_2$, washed with saturated $NaHCO_3$, water, and brine; dried ($MgSO_4$); and the solvent evaporated. Column chromatography (silica gel hexanes:EtOAc=8:1) gave 67 as a white solid (661 mg, 74% yield). mp 66-68° C.

b. Preparation of 3-(1-(tetrahydro-2H-pyran-2-yl)-1H-indazol-5-yl)propanenitrile (Compound 68).

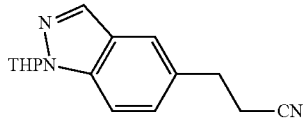

The procedure used to prepare 68 is the same as that to prepare 40 except that 67 (258 mg, 0.88 mmol) was used instead of 31, afforded the desired product, 68, as a colorless oil (369 mg, 80% yield).

c. Preparation of 5-(2-(2H-tetrazol-5-yl)ethyl)-1-(tetrahydro-2H-pyran-2-yl)-1H-indazole (Compound 69).

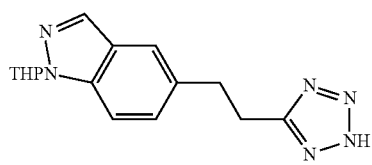

The procedure used to prepare 69 was the same as that to used prepare 33, except that 68 (369 mg, 1.45 mmol) was used instead of 32, afforded the desired product, 69, as a white solid (354 mg, 82% yield). $^1$HNMR (300 MHz, CDCl$_3$) δ 7.77 (s, 1H), 7.36 (m, 2H), 7.08 (d, J=8.7 Hz, 1H), 5.61 (dd, J=9.9, 2.1 Hz, 1H), 3.97 (d, J=11.6 Hz, 1H), 3.68 (t, J=9.1 Hz, 1H), 3.22 (t, J=6.8 Hz, 2H), 3.11 (m, 2H), 2.41 (m, 1H), 1.98 (m, 3H), 1.65 (m, 2H). $^{13}$C NMR (75 MHz, CDCl$_3$) δ 155.70, 138.35, 133.61, 132.42, 127.84, 124.53, 120.01, 110.03, 85.23, 67.84, 33.44, 29.59, 25.57, 24.91, 22.60.

d. Preparation of 5-(2-(2H-tetrazol-5-yl)ethyl)-1H-indazole (Compound 16).

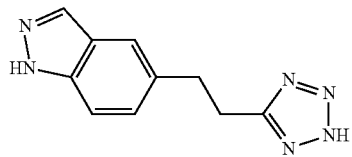 [SMILES: c1cc2[nH]ncc2cc1CCc1nn[nH]n1]

A solution of 69 (100 mg, 0.34 mmol) in EtOH (2 mL) was added 1 M HCl in MeOH (0.67 mL, 0.67 mmol). The resulting mixture was refluxed for 4 h. The reaction mixture was concentrated and the residue was directly purified by column chromatography (silica gel, CH$_2$Cl2:MeOH=10:1) to yield 17 (70 mg, 96% yield) as a white solid. $^1$H NMR (500 MHz, DMSO) δ 11.53 (br, 1H), 8.01 (dd, J=14.7, 1.8 Hz, 1H), 7.53 (s, 1H), 7.45 (m, 1H), 7.22 (m, 1H), 3.22 (t, J=7.3 Hz, 2H), 3.13 (t, J=7.3 Hz, 2H). $^{13}$C NMR (125 MHz, DMSO) δ 156.01, 139.54, 133.32, 132.80, 128.26, 123.46, 110.96, 33.40, 25.78. HRMS (ESI) m/z calcd. for C$_{10}$H$_{10}$N$_6$Na [M+Na]$^+$ 237.0865, found 237.0870.

18. Preparation of 5-(((2H-tetrazol-5-yl)methyl)amino)-1H-indazol-1-ol (Compound 17).

The overall synthesis scheme (Synthesis Scheme 17) for the preparation of Compound 17 is shown below. The synthesis proceeds through the intermediates indicated (Compounds 70, 71, 72, 73, 74, and 75). The yield for each synthetic step was as indicated.

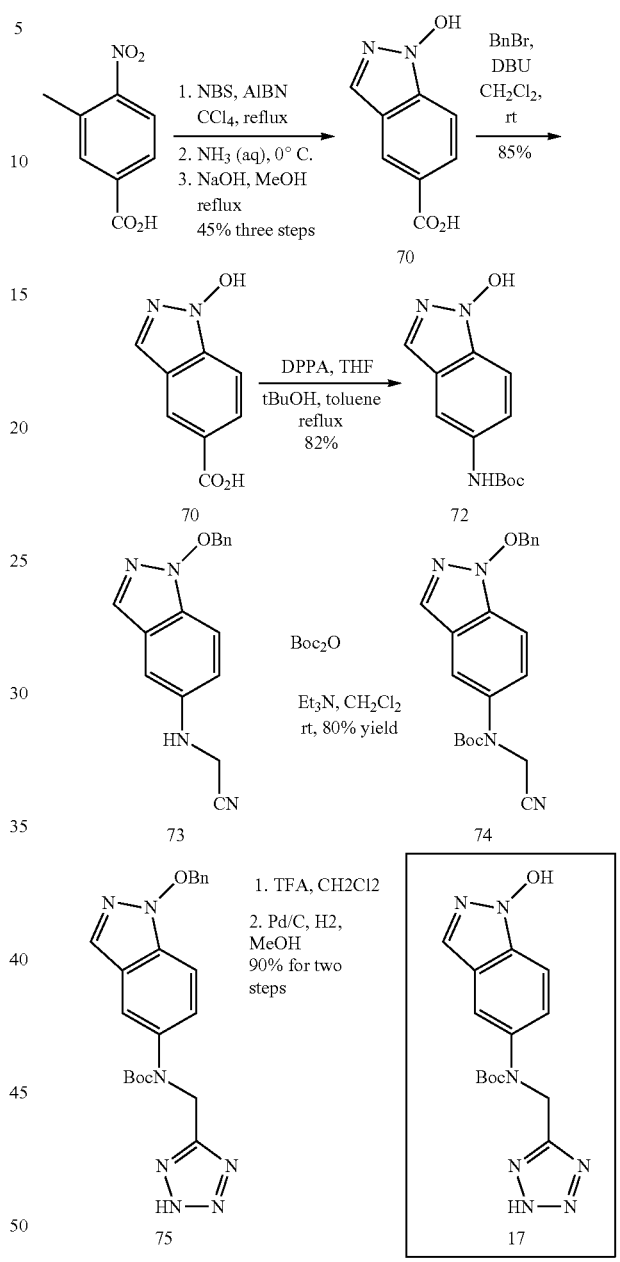

a. Preparation of 1-hydroxy-1H-indazole-5-carboxylic acid (Compound 70).

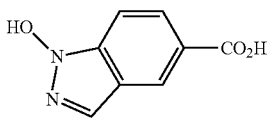 [SMILES: O=C(O)c1ccc2c(cnn2O)c1]

A solution of 3-methyl-4-nitrobenzoic acid (539 mg, 2.98 mmol) in benzene (20 mL) was heated to reflux in a sealed tube after which N-bromosuccinimide (679 mg, 3.43 mol) and AIBN (49 mg, 0.298 mol) were carefully added in a portion wise manner over 5 min. After 12 h the mixture was cooled to room temperature, and the succinimide was filtered off and washed with benzene (5 mL×3). The solvent was removed under reduced pressure and purified by column chromatography to give the desired product 3-(bromomethyl)-4-nitrobenzoic acid (553 mg, 68% yield) as a viscous yellow oil.

An aqueous solution of 25% w/v ammonia (100 mL) was treated with EtOH (200 mL) and cooled to −78° C. The mixture was slowly treated with a cooled (−78° C.) solution of the benzylbromide (2.58 g, 10.0 mmol) in ethanol (100 mL). The mixture was then allowed to come to room temperature and stirred for 48 h. The mixtures were evaporated under reduced pressure and the residue solid was washed with CH$_2$Cl$_2$ to afford 3-(aminomethyl)-4-nitrobenzoic acid (1.7 g, 87% yield).

The 3-(aminomethyl)-4-nitrobenzoic acid (1.71 g, 8.73 mmol) was treated with a 1M methanolic solution of sodium hydroxide (20 mL) and heated at 80° C. overnight. The mixture was concentrated and H$_2$O (50 mL) was added. The aqueous phase was washed with EtOAc (10 mL×2), and then was acidified with 1 N HCl to pH 4. The aqueous phase was extracted with EtOAc (20 mL×2), and then was dried over Na$_2$SO$_4$ and concentrated to provide product 70 (1.18 g, 76% yield) as a pink solid.

b. Preparation of 1-(benzyloxy)-1H-indazole-5-carboxylic acid (Compound 71).

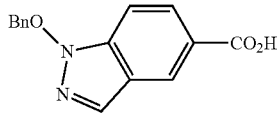 [SMILES: O=C(O)c1ccc2c(cnn2OCc2ccccc2)c1]

Benzyl bromide (481.3 mg, 2.81 mmol) was added dropwise to an ice-cooled mixture of 70 (477 mg, 2.68 mmol) and DBU (427.5 mg, 2.81 mmol) in CH$_2$Cl$_2$ (20 mL). The resulting mixture was stirred at room temperature for 30 min, diluted with water, and then extracted with EtOAc (10 mL×2). The extract was washed with water and brine, and dried over Na$_2$SO$_4$. The solvent was evaporated in vacuo. The residue was purified by column chromatography to yield the desired product, 71, as a colorless oil (610.0 mg, 85% yield).

c. Preparation of tert-butyl (1-(benzyloxy)-1H-indazol-5-yl)carbamate (Compound 72).

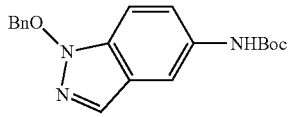

The compound prepared as described above, 71, was dissolved (713 mg, 2.66 mmol) in t-BuOH (10 mL)/toluene (10 mL) over 4 Å molecular sieves. To this solution was added Et$_3$N (467 μL, 3.35 mmol) and diphenylphosphorylazide (602 μL, 2.79 mmol). The reaction mixture was warmed to reflux under Ar and stirred for 14 h. The mixture was then filtered through Celite to remove the molecular sieves and concentrated under reduced pressure. The residue was diluted with 10% aqueous HCl and extracted with EtOAc (3×20). The organic extracts were combined and washed with H$_2$O and saturated aqueous NaCl. The organic phase was dried over Na$_2$SO$_4$ and concentrated under reduced pressure. Flash chromatography provided the desired product, 72, (739 mg, 82%).

d. Preparation of 2-((1-(benzyloxy)-1H-indazol-5-yl)amino)acetonitrile (Compound 73).

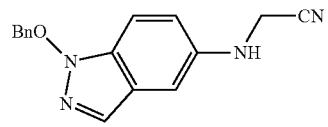 [SMILES: N#CCNc1ccc2c(cnn2OCc2ccccc2)c1]

To a solution of 72 (115 mg, 0.34 mmol) in dry CH$_2$Cl$_2$ (1 mL) at 0° C. was added TFA (5 mL). The resulting mixture was stirred for 2 h. The reaction mixture was concentrated and the residue was directly used in next step. The residue was dissolved in DMF, and to the solution was added NaH (60% in mineral oil; 27 mg, 0.68 mmol) at 0° C. After 20 min 2-bromoacetonitrile (119 mg, 0.51 mmol) was added into the mixture. The reaction mixture was warmed to 60° C. for 8 h and then was allowed to cool to room temperature. The reaction mixture was concentrated in vacuo, and the residue was treated with EtOAc. The organic extracts were combined and washed with H$_2$O and saturated aqueous NaCl. The organic phase was dried over Na$_2$SO$_4$ and concentrated under reduced pressure. Flash chromatography provided the desired product, 73, (52 mg, 55% in two steps).

e. Preparation of tert-butyl (1-(benzyloxy)-1H-indazol-5-yl)(cyanomethyl)carbamate (Compound 74).

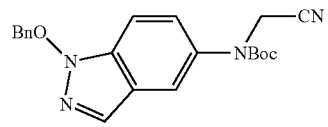

Boc$_2$O (481.3 mg, 2.81 mmol) was added dropwise to an ice-cooled mixture of 73 (477 mg, 2.68 mmol) and Et$_3$N (427.5 mg, 2.81 mmol) in CH$_2$Cl$_2$ (20 mL). The resulting mixture was stirred at room temperature for 30 min, diluted with water, and extracted with EtOAc (10 mL×2). The extract was washed with water and brine, and dried over Na$_2$SO$_4$. The solvent was evaporated in vacuo. The residue was purified by column chromatography to yield the desired product, 74, as a colorless oil (610.0 mg, 85% yield).

f. Preparation of tert-butyl ((2H-tetrazol-5-yl)methyl)(1-(benzyloxy)-1H-indazol-5-yl)carbamate (Compound 75).

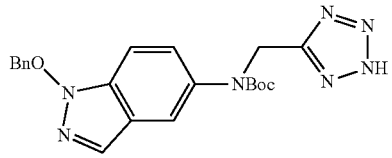 [SMILES: CC(C)(C)OC(=O)N(Cc1nn[nH]n1)c1ccc2c(cnn2OCc2ccccc2)c1]

The procedure used to prepare 75 was the same as the procedure used to prepare 33 except that 74 (211 mg, 0.56 mmol) was used instead of 32, afforded the desired product, 75, (183 mg, 78% yield). $^1$H NMR (300 MHz, CDCl$_3$) δ 7.73 (s, 1H), 7.37 (m, 1H), 7.32 (m, 5H), 7.02 (t, J=7.9 Hz, 2H), 5.35 (s, 2H), 4.99 (s, 2H), 1.36 (s, 6H).

g. Preparation of 5-(((2H-tetrazol-5-yl)methyl)amino)-1H-indazol-1-ol (Compound 17).

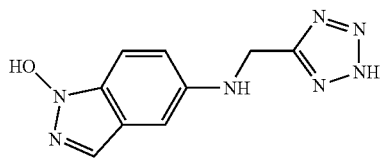 [SMILES: On1ncc2cc(NCc3nn[nH]n3)ccc21]

To a solution of 75 (63 mg, 0.15 mmol) in dry CH$_2$Cl$_2$ (1 mL) at 0° C. was added TFA (5 mL). The resulting mixture was stirred for 2 h. The reaction mixture was concentrated and the residue was separated by column chromatography to yield N-((2H-tetrazol-5-yl)methyl)-1-(benzyloxy)-1H-indazol-5-amine (43.3 mg, 90%).

To a solution of N-((2H-tetrazol-5-yl)methyl)-1-(benzyloxy)-1H-indazol-5-amine (43 mg, 0.14 mmol) in dry MeOH (10 mL) was added 10% Pd on charcoal (5 mg). The reaction was stirred under hydrogen atmosphere overnight, and then the solution was filtered over filter paper. Solvent was removed using a rotatory evaporator to provide the desired product, 76, (32 mg, 0.14 mmol) as a pale green solid in quantitative yield. $^1$H NMR (500 MHz, DMSO) δ 7.95 (s, 1H), 7.72 (s, 1H), 7.60 (d, J=8.5 Hz, 1H), 7.02 (dd, J=1.5, 8.5 Hz, H), 5.35 (s, 2H). $^{13}$C NMR (125 MHz, DMSO) δ 155.90, 140.24, 134.21, 129.74, 127.39, 123.31, 120.85, 110.81, 60.94. MS (ESI, CH$_3$OH): [C$_9$H$_9$N$_7$O]m/z 232.1 ([M+H]$^+$).

19. Preparation of N-((2H-tetrazol-5-yl)methyl)-N-(1-hydroxy-1H-indazol-5-yl)-3,5-dimethylisoxazole-4-carboxamide (Compound 18).

The overall synthesis scheme (Synthesis Scheme 18) for the preparation of Compound 18 is shown below. The synthesis proceeds through the intermediates indicated (Compounds 74, 77, and 78). The yield for each synthetic step was as indicated.

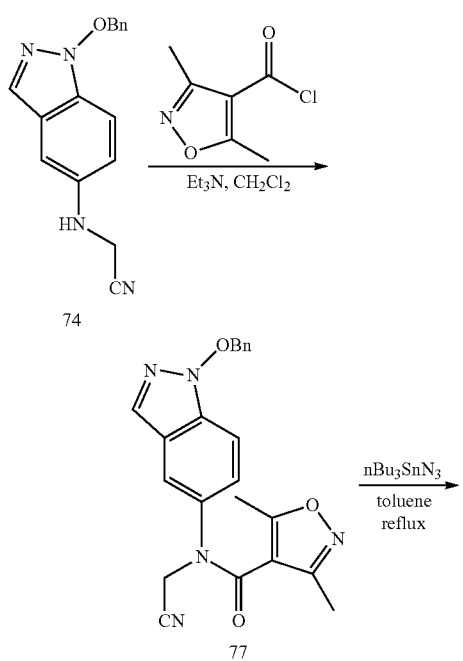

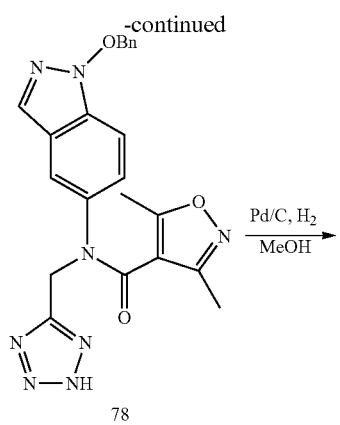

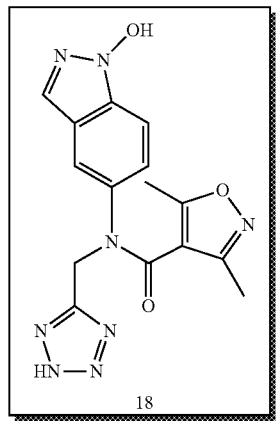

a. Preparation of N-(1-(benzyloxy)-1H-indazol-5-yl)-N-(cyanomethyl)-3,5-dimethylisoxazole-4-carboxamide (Compound 77).

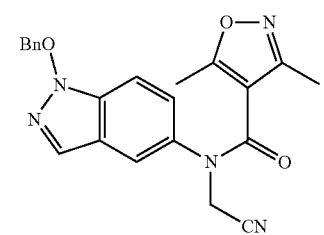 [SMILES: Cc1noc(C)c1C(=O)N(CC#N)c1ccc2c(cnn2OCc2ccccc2)c1]

3,5-Dimethylisoxazole-4-carbonyl chloride (118 mg, 0.74 mmol) was added dropwise to an ice-cooled mixture of 74 (206 mg, 0.74 mmol) and Et$_3$N (150 mg, 1.48 mmol) in CH$_2$C$_2$ (10 mL). The resulting mixture was stirred at room temperature over night, diluted with water, and extracted with ethyl acetate. The extract was washed with brine and dried over Na$_2$SO$_4$. The solvent was evaporated in vacuo. The residue was purified by column chromatography to yield the desired product, 77, (208 mg, 70% yield) as colorless oil.

b. Preparation of N-((2H-tetrazol-5-yl)methyl)-N-(1-(benzyloxy)-1H-indazol-5-yl)-3,5-dimethylisoxazole-4-carboxamide (Compound 78).

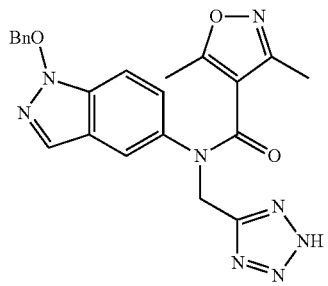 [SMILES: Cc1noc(C)c1C(=O)N(Cc1nn[nH]n1)c1ccc2c(cnn2OCc2ccccc2)c1]

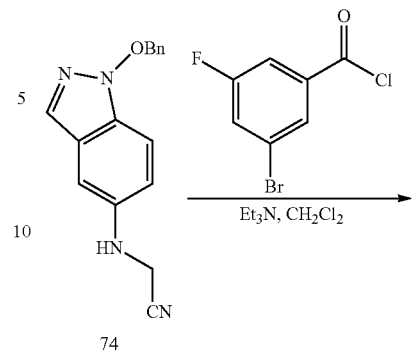

The procedure used to prepare 78 was the same as that to used prepare 33 except that 77 (100 mg, 0.25 mmol) was used instead of 32, afforded the desired product, 78, (98.8 mg, 89% yield). $^1$H NMR (500 MHz, CDCl$_3$) δ 7.70 (s, 1H), 7.30 (m, 2H), 7.24 (m, 4H), 6.88 (dd, J=20.0, 8.8 Hz, 2H), 5.32 (s, 2H), 5.18 (s, 2H), 2.01 (s, 3H), 1.91 (s, 3H).

c. Preparation of N-((2H-tetrazol-5-yl)methyl)-N-(1-hydroxy-1H-indazol-5-yl)-3,5-dimethylisoxazole-4-carboxamide (Compound 18).

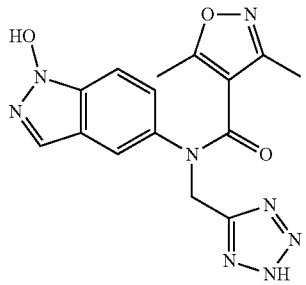 [SMILES: Cc1noc(C)c1C(=O)N(Cc1nn[nH]n1)c1ccc2c(cnn2O)c1]

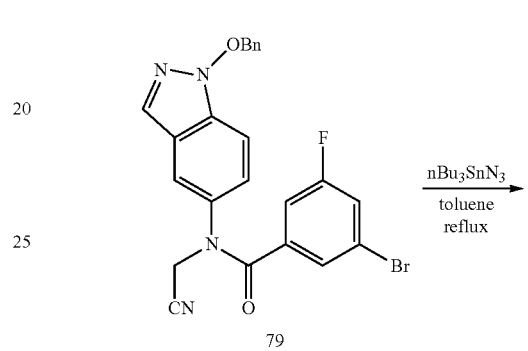

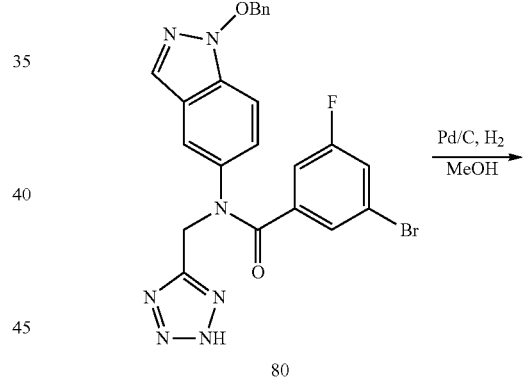

To a solution of 78 (112 mg, 0.25 mmol) in dry MeOH (10 mL) was added 10% Pd on charcoal (10 mg). The reaction was stirred under hydrogen atmosphere overnight, and then the solution was filtered over filter paper. Solvent was removed using a rotatory evaporator to afford the desired product, 18, (434 mg, 1.4 mmol) as a pale red solid in quantitative yield. $^1$H NMR (500 MHz, DMSO) δ 7.76 (d, J=0.9 Hz, 1H), 7.65 (d, J=1.9 Hz, 1H), 7.41 (d, J=8.9 Hz, 1H), 7.28 (dd, J=8.7, 1.7 Hz, 1H), 5.29 (s, 3H), 2.58 (s, 3H), 2.31 (s, 3H). MS (ESI, CH$_3$OH): [C$_{15}$H$_{14}$N$_8$O$_3$]m/z 355.4 ([M+H]$^+$).

20. Preparation of N-((2H-tetrazol-5-yl)methyl)-3-bromo-5-fluoro-N-(1-hydroxy-1H-indazol-5-yl)benzamide (Compound 19).

The overall synthesis scheme (Synthesis Scheme 19) for the preparation of Compound 19 is shown below. The synthesis proceeds through the intermediates indicated (Compounds 74, 79, and 80). The yield for each synthetic step was as indicated.

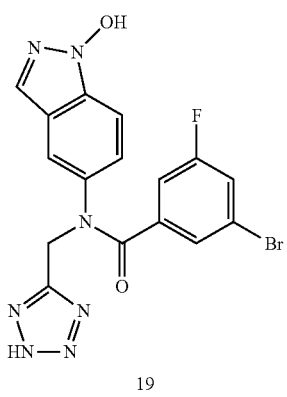

a. Preparation of N-(1-(benzyloxy)-1H-indazol-5-yl)-3-bromo-N-(cyanomethyl)-5-fluorobenzamide (Compound 79).

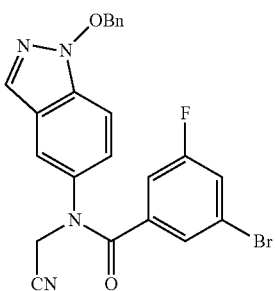 [SMILES: N#CCN(C(=O)c1cc(F)cc(Br)c1)c1ccc2c(cnn2OCc2ccccc2)c1]

The procedure used to prepare 62 was the same as that used to prepare 39 except 51 was used (315 mg, 1.17 mmol) instead of 31, afforded the desired product, 62, as a colorless viscous oil (511 mg, 82% yield).

b. Preparation of N-((2H-tetrazol-5-yl)methyl)-N-(1-(benzyloxy)-1H-indazol-5-yl)-3-bromo-5-fluorobenzamide (Compound 80).

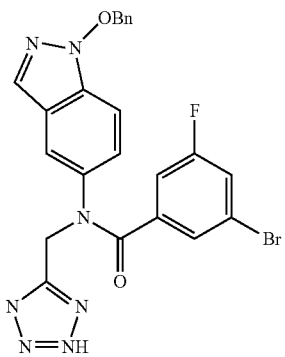 [SMILES: O=C(c1cc(F)cc(Br)c1)N(Cc1nnn[nH]1)c1ccc2c(cnn2OCc2ccccc2)c1]

The procedure used to prepare 15 was the same as that used to prepare 4 except 62 was used (265 mg, 0.50 mmol) instead of 39, afforded the desired product, as a pale yellow solid (84 mg, 68% yield for two steps).

c. Preparation of N-((2H-tetrazol-5-yl)methyl)-3-bromo-5-fluoro-N-(1-hydroxy-1H-indazol-5-yl)benzamide (Compound 19).

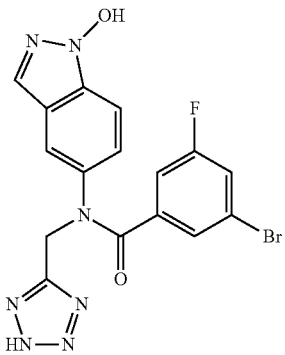 [SMILES: O=C(c1cc(F)cc(Br)c1)N(Cc1nn[nH]n1)c1ccc2c(cnn2O)c1]

The procedure used to prepare 15 was the same as that used to prepare 4 except 62 was used (265 mg, 0.50 mmol) instead of 39, afforded the desired product, as a pale yellow solid (84 mg, 68% yield for two steps).

21. Preparation of N-((2H-tetrazol-5-yl)methyl)-3-chloro-N-(1-hydroxy-1H-indazol-5-yl)benzamide (Compound 20).

The overall synthesis scheme (Synthesis Scheme 20) for the preparation of Compound 20 is shown below. The synthesis proceeds through the intermediates indicated (Compounds 74, 81, and 82). The yield for each synthetic step was as indicated.

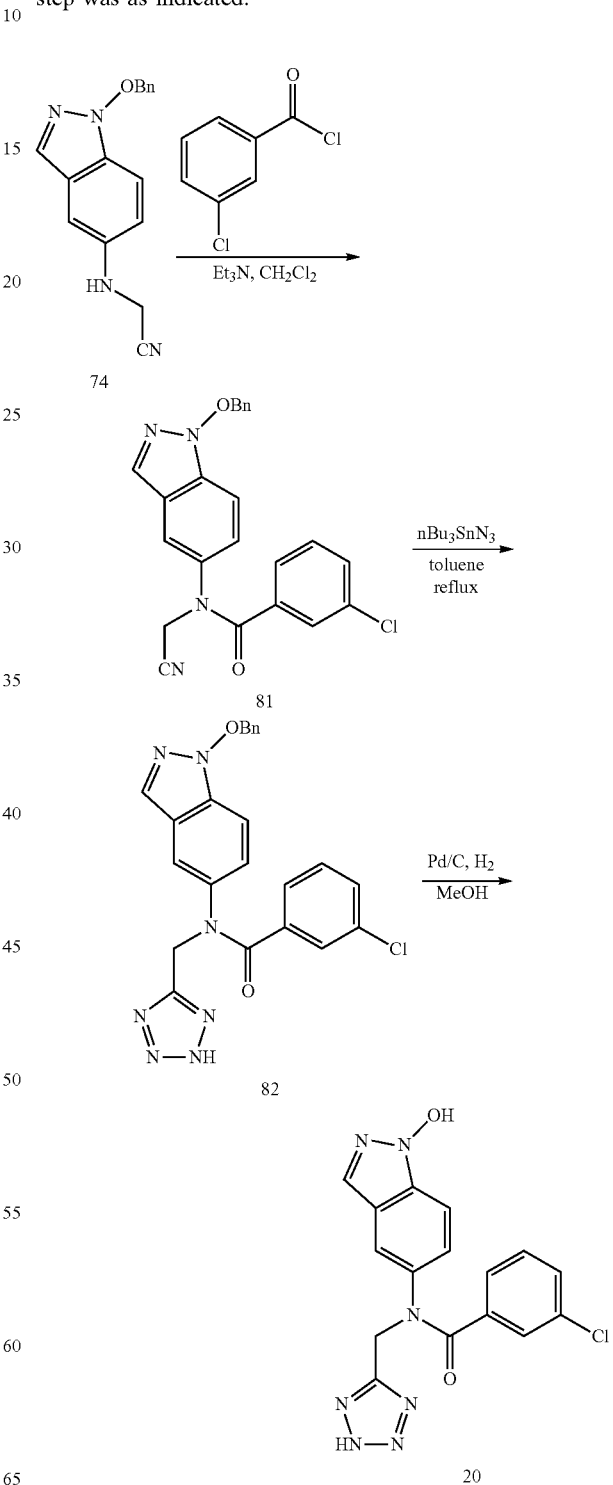

a. Preparation of N-(1-(benzyloxy)-1H-indazol-5-yl)-3-chloro-N-(cyanomethyl)benzamide (Compound 81).

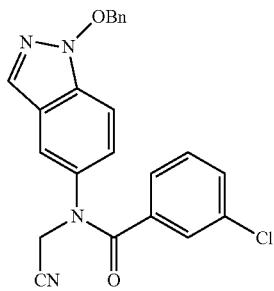 [SMILES: N#CCN(C(=O)c1cccc(Cl)c1)c1ccc2c(cnn2OCc2ccccc2)c1]

The procedure used to prepare 81 was the same as that used to prepare 77 except that 3-chlorobenzoyl chloride (95.2 mg, 0.55 mmol) was used instead of 3,5-dimethyl-isoxazole-4-carbonyl chloride, afforded the desired product, 81, (149 mg, 65% yield).

b. Preparation of N-((2H-tetrazol-5-yl)methyl)-N-(1-(benzyloxy)-1H-indazol-5-yl)-3-chlorobenzamide (Compound 82).

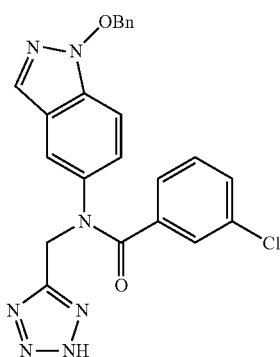 [SMILES: O=C(c1cccc(Cl)c1)N(Cc1nn[nH]n1)c1ccc2c(cnn2OCc2ccccc2)c1]

The procedure used to prepare 82 was the same as that used to prepare 33 except that 81 (91.5 mg, 0.22 mmol) was instead of 32, afforded the desired product, 82, (95.9 mg, 95% yield) as a solid. $^1$H NMR (500 MHz, CDCl$_3$) δ 7.69 (s, 1H), 7.31 (m, 3H), 7.26 (m, 4H), 7.22 (m, 2H), 7.02 (dd, J=7.4, 5.1 Hz, 2H), 6.94 (dd, J=6.5, 4.7 Hz, 2H), 5.32 (s, 2H), 5.30 (s, 2H). $^{13}$C NMR (125 MHz, CDCl$_3$) δ 170.89, 135.72, 135.20, 134.25, 133.73, 133.44, 130.90, 129.85, 129.43, 129.32, 128.92, 128.66, 128.11, 126.77, 125.99, 120.79, 119.70, 110.16, 80.51.

c. Preparation of N-((2H-tetrazol-5-yl)methyl)-3-chloro-N-(1-hydroxy-1H-indazol-5-yl)benzamide (Compound 20).

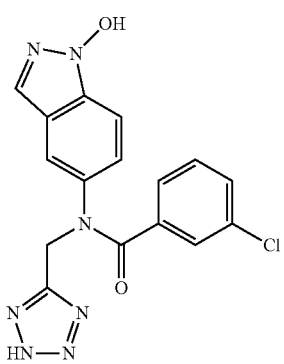 [SMILES: O=C(c1cccc(Cl)c1)N(Cc1nn[nH]n1)c1ccc2c(cnn2O)c1]

The procedure used to prepare 20 was the same as that used to prepare 18 except that 82 (114.7 mg, 0.25 mmol) was used instead of 78, afforded the desired product, 20, as a solid (92.3 mg, 99% yield). $^1$H NMR (500 MHz, DMSO) δ 12.30 (br, 1H), 7.72 (s, 1H), 7.58 (s, 1H), 7.38 (m, 2H), 7.29 (m, 2H), 7.18 (m, 2H), 5.33 (s, 2H). $^{13}$C NMR (125 MHz, DMSO) δ 169.08, 154.68, 136.12, 133.12, 130.44, 130.15, 128.70, 127.49, 126.68, 121.04, 120.93, 110.06, 40.67. MS (ESI, CH$_3$OH): [C$_{16}$H$_{12}$ClN$_7$O$_2$]m/z 370.3 ([M+H]$^+$).

22. Preparation of N-((2H-tetrazol-5-yl)methyl)-N-(1-hydroxy-H-indazol-5-yl)nicotinamide (Compound 21).

The overall synthesis scheme (Synthesis Scheme 21) for the preparation of Compound 21 is shown below. The synthesis proceeds through the intermediates indicated (Compounds 74, 83, and 84). The yield for each synthetic step was as indicated.

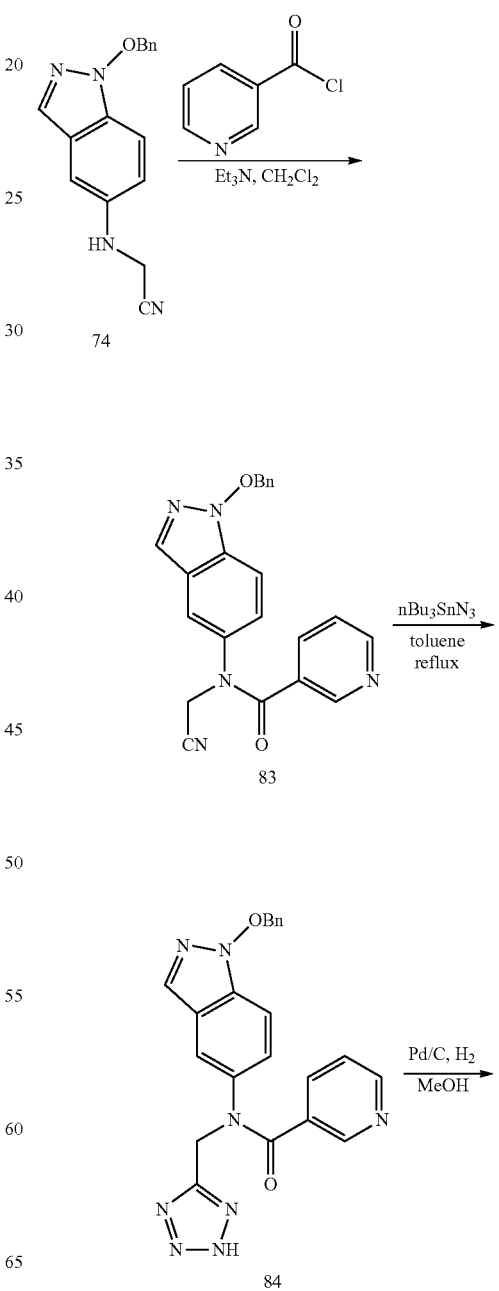

c. Preparation of N-((2H-tetrazol-5-yl)methyl)-N-(1-hydroxy-1H-indazol-5-yl)nicotinamide (Compound 21).

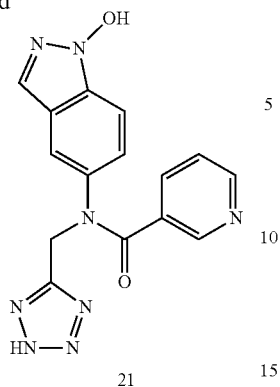

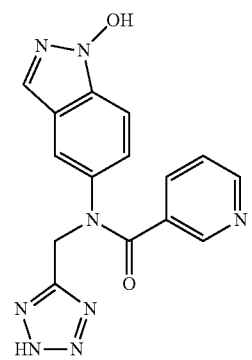

a. Preparation of N-(1-(benzyloxy)-1H-indazol-5-yl)-N-(cyanomethyl)nicotinamide (Compound 83).

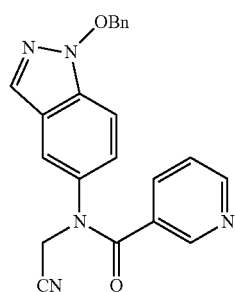 [SMILES: N#CCN(C(=O)c1cccnc1)c1ccc2c(cnn2OCc2ccccc2)c1]

The procedure used to prepare 83 was the same as that used to prepare 77 except that nicotinoyl chloride (94.5 mg, 0.67 mmol) was used instead of 3,5-dimethylisoxazole-4-carbonyl chloride, afforded the desired product, 83, (174 mg, 68% yield).

b. Preparation of N-((2H-tetrazol-5-yl)methyl)-N-(1-(benzyloxy)-1H-indazol-5-yl)nicotinamide (Compound 84).

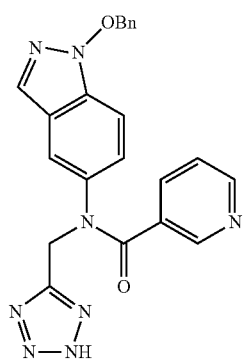 [SMILES: O=C(c1cccnc1)N(Cc1nn[nH]n1)c1ccc2c(cnn2OCc2ccccc2)c1]

The procedure used to prepare 84 was the same as that used to prepare 33 except that 83 (134 mg, 0.35 mmol) was used instead of 32, afforded the desired product, 84, as a solid (118 mg, 79% yield). $^1$H NMR (500 MHz, CDCl3) δ 8.62 (s, 1H), 8.50 (d, J=3.9 Hz, 1H), 7.67 (s, 1H), 7.51 (d, J=7.6 Hz, 1H), 7.39 (s, 1H), 7.29 (m, 6H), 7.08 (m, 1H), 6.99 (q, J=8.8 Hz, 2H), 5.34 (s, 2H), 5.31 (s, 3H). $^{13}$C NMR (125 MHz, CDCl3) δ 169.01, 150.49, 149.28, 136.69, 135.40, 133.64, 133.42, 130.31, 129.81, 129.39, 128.64, 128.09, 126.21, 122.99, 120.81, 120.17, 110.26.

The procedure used to prepare 21 was the same as that used to prepare 18 except that 84 (76.7 mg, 0.18 mmol) was used instead of 78, afforded the desired product, 21, as a solid (60.5 mg, 100% yield). $^1$H NMR (300 MHz, DMSO) δ 8.46 (s, 1H), 8.38 (d, J=4.2 Hz, 1H), 7.74 (s, 1H), 7.67 (m, 1H), 7.63 (s, 1H), 7.42 (d, J=8.8 Hz, 1H), 7.32 (d, J=1.8, 6.0 Hz, 1H), 7.24 (m, 2H). $^{13}$C NMR (125 MHz, DMSO) δ 168.49, 154.09, 150.69, 149.14, 136.78, 135.81, 133.17, 132.12, 127.51, 126.74, 123.80, 121.26, 121.07, 110.27, 44.36. MS (ESI, CH$_3$OH): [C$_{15}$H$_{12}$N$_8$O$_2$]m/z 337.2 ([M+H]$^+$).

23. Preparation of N-((2H-tetrazol-5-yl)methyl)-N-(1-hydroxy-1H-indazol-5-yl)-3-phenylpropanamide (Compound 22).

The overall synthesis scheme (Synthesis Scheme 22) for the preparation of Compound 22 is shown below. The synthesis proceeds through the intermediates indicated (Compounds 74, 85, and 86). The yield for each synthetic step was as indicated.

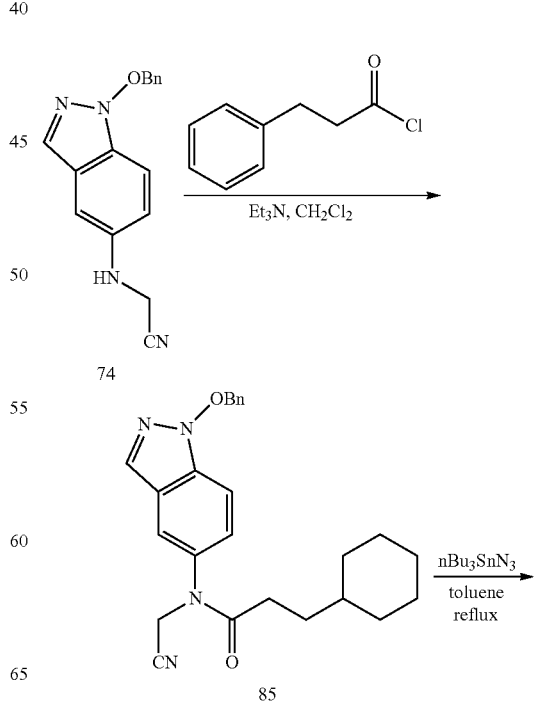

-continued

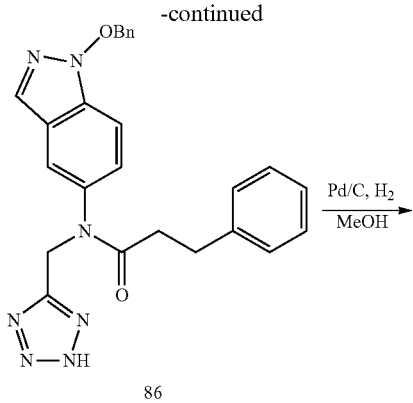

86

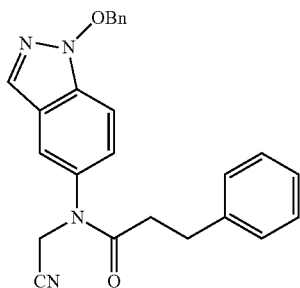 [SMILES: N#CCN(C(=O)CCc1ccccc1)c1ccc2c(cnn2OCc2ccccc2)c1]

a. Preparation of N-(1-(benzyloxy)-1H-indazol-5-yl)-N-(cyanomethyl)-3-phenylpropanamide (Compound 85).

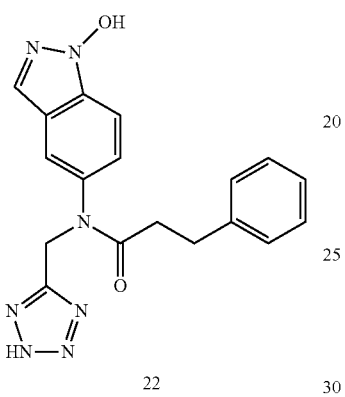

The procedure used to prepare 85 was the same as that used to prepare 77 except that 3-phenylpropanoyl chloride (155 mg, 0.92 mmol) was used instead of 3,5-dimethylisoxazole-4-carbonyl chloride, afforded the desired product, 85, (254 mg, 65% yield).

b. Preparation of N-((2H-tetrazol-5-yl)methyl)-N-(1-(benzyloxy)-1H-indazol-5-yl)-3-phenylpropanamide (Compound 86).

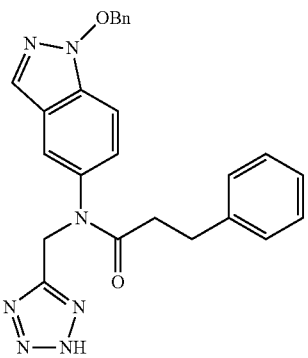 [SMILES: O=C(CCc1ccccc1)N(Cc1nn[nH]n1)c1ccc2c(cnn2OCc2ccccc2)c1]

The procedure used to prepare 86 was the same as that used to prepare 33 except that 85 (287 mg, 0.70 mmol) was instead of 32, afforded the desired product, 86, as a solid (206 mg, 65% yield). $^1$H NMR (300 MHz, CDCl$_3$) δ 7.73 (s, 1H), 7.29 (td, J=8.0, 2.3 Hz, 5H), 7.17 (m, 3H), 7.04 (m, 2H), 6.94 (s, 2H), 6.75 (d, J=9.1 Hz, 1H), 5.35 (s, 2H), 5.07 (s, 2H), 2.89 (t, J=7.4 Hz, 2H), 2.40 (t, J=7.4 Hz, 2H).

c. Preparation of N-((2H-tetrazol-5-yl)methyl)-N-(1-hydroxy-1H-indazol-5-yl)-3-phenylpropanamide (Compound 22).

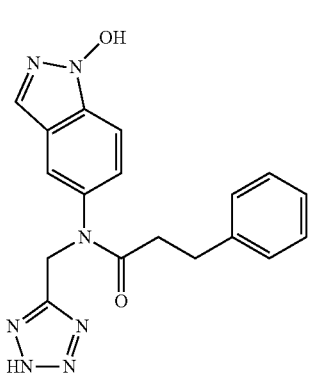 [SMILES: O=C(CCc1ccccc1)N(Cc1nn[nH]n1)c1ccc2c(cnn2O)c1]

The procedure used to prepare 22 was the same as that used to prepare 18 except that 86 (90.6 mg, 0.20 mmol) was used instead of 78, afforded the desired product, 22, as a solid (72.6 mg, 100% yield). $^1$H NMR (300 MHz, DMSO) δ 7.79 (s, 1H), 7.47 (s, 1H), 7.33 (m, 5H), 7.17 (d, J=8.7 Hz, 1H), 7.02 (dd, J=8.7, 1.8 Hz, 1H), 5.11 (s, 2H). MS (ESI, CH$_3$OH): [C$_{18}$H$_{17}$N$_7$O$_2$]m/z 364.4 ([M+H]$^+$).

24. Preparation of N-((2H-tetrazol-5-yl)methyl)-3-cyclopentyl-N-(1-hydroxy-1H-indazol-5-yl)propanamide (Compound 23).

The overall synthesis scheme (Synthesis Scheme 23) for the preparation of Compound 23 is shown below. The synthesis proceeds through the intermediates indicated (Compounds 74, 87, and 88). The yield for each synthetic step was as indicated.

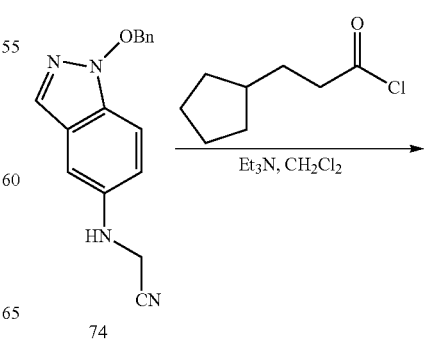

74

-continued

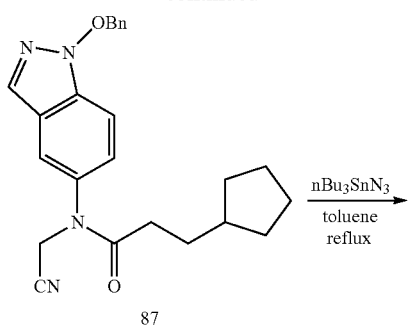
87

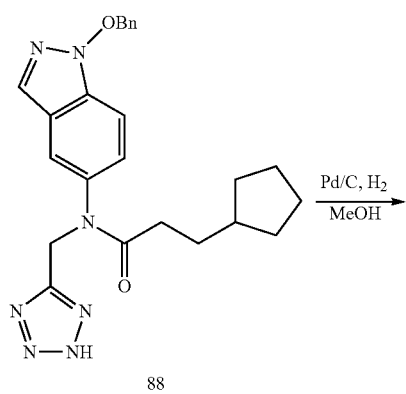
88

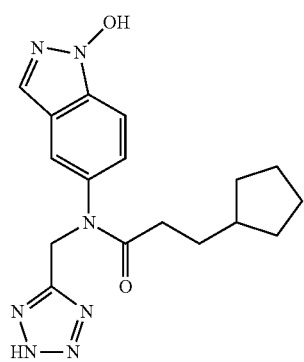
23 a. Preparation of N-(1-(benzyloxy)-1H-indazol-5-yl)-N-(cyanomethyl)-3-cyclopentylpropanamide (Compound 87).

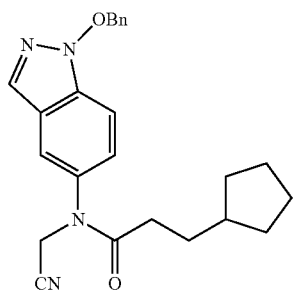 [SMILES: N#CCN(C(=O)CCC1CCCC1)c1ccc2c(cnn2OCc2ccccc2)c1]

The procedure used to prepare 87 was the same as that used to prepare 77 except that 3-cyclopentylpropanoyl chloride (168 mg, 1.05 mmol) was used instead of 3,5-dimethylisoxazole-4-carbonyl chloride, afforded the desired product, 87, (287 mg, 68% yield).

b. Preparation of N-((2H-tetrazol-5-yl)methyl)-N-(1-(benzyloxy)-1H-indazol-5-yl)-3-cyclopentylpropanamide (Compound 88).

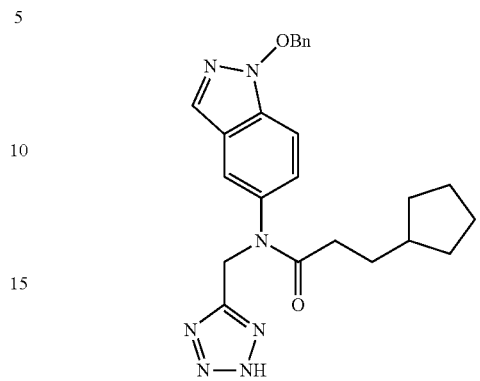

The procedure used to prepare 88 was the same as that used to prepare 33 except that 87 (68.3 mg, 0.17 mmol) was used instead of 32, afforded the desired product, 88, as a solid (69.6 mg, 92% yield). $^1$H NMR (300 MHz, CDCl$_3$) δ 7.81 (d, J=0.8 Hz, 1H), 7.46 (dd, J=5.8, 4.7 Hz, 1H), 7.32 (m, 5H), 7.15 (dd, J=8.8, 0.7 Hz, 1H), 7.01 (m, 1H), 5.38 (s, 2H), 5.13 (s, 2H), 2.09 (m, 2H), 1.45 (m, 11H). $^{13}$C NMR (75 MHz, CDCl$_3$) δ 176.05, 135.06, 133.90, 133.75, 129.86, 129.37, 128.63, 128.14, 126.31, 121.09, 120.13, 110.29, 80.49, 43.40, 39.42, 33.33, 32.19, 31.61, 27.71, 24.86.

c. Preparation of N-((2H-tetrazol-5-yl)methyl)-3-cyclopentyl-N-(1-hydroxy-1H-indazol-5-yl)propanamide (Compound 23).

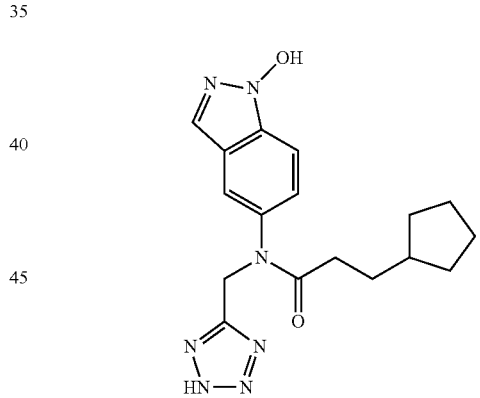

The procedure used to prepare 23 was the same as that used to prepare 18 except that 88 (88.4 mg, 0.22 mmol) was used instead of 78, afforded the desired product, 23, as a solid (78.1 mg, 100% yield). $^1$H NMR (300 MHz, DMSO) δ 8.13 (d, J=7.4 Hz, 1H), 7.75 (m, 1H), 7.55 (t, J=8.2 Hz, 2H), 7.36 (s, 1H), 5.10 (s, 2H), 2.01 (m, 2H), 1.37 (m, 11H). MS (ESI, CH$_3$OH): [C$_{18}$H$_{17}$N$_7$O$_2$]m/z 356.5 ([M+H]$^+$).

25. Preparation of N-((2H-tetrazol-5-yl)methyl)-N-(1-hydroxy-1H-indazol-5-yl)cyclopropanecarboxamide (Compound 24).

The overall synthesis scheme (Synthesis Scheme 24) for the preparation of Compound 24 is shown below. The synthesis proceeds through the intermediates indicated (Compounds 74, 89, and 90). The yield for each synthetic step was as indicated.

b. Preparation of N-(1-(benzyloxy)-1H-indazol-5-yl)-N-(cyanomethyl)cyclopropanecarboxamide (Compound 90).

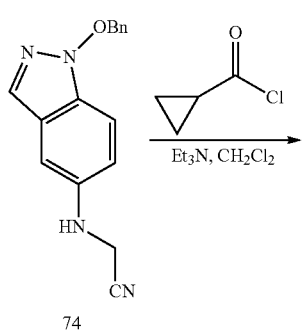

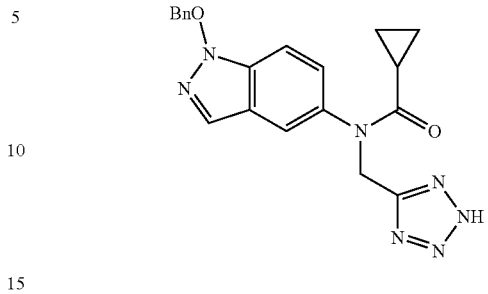

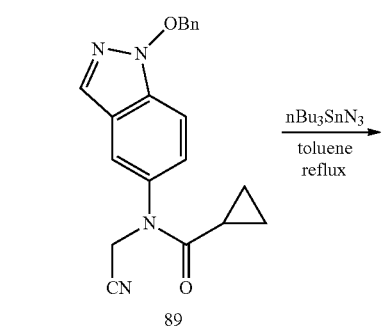

The procedure used to prepare 90 was the same procedure as that used to prepare 33 except that 89 (86.5 mg, 0.25 mmol) was used instead of 32, afforded the desired product, 90, as a solid (75.7 mg, 78% yield). $^1$H NMR (300 MHz, CDCl$_3$) δ 9.03 (d, J=14.6 Hz, 1H), 8.87 (d, J=17.4 Hz, 1H), 8.57 (m, 6H), 8.43 (q, J=8.9 Hz, 2H), 6.63 (m, 2H), 6.38 (s, 2H), 2.54 (dd, J=13.6, 5.0 Hz, 1H), 2.25 (m, 2H), 1.95 (t, J=9.6 Hz, 2H). $^{13}$C NMR (75 MHz, CDCl$_3$) δ 176.10, 152.70, 135.14, 133.83, 133.75, 129.82, 129.34, 128.63, 128.17, 126.64, 121.19, 120.32, 110.21, 80.50, 43.57, 12.70, 9.47.

c. Preparation of N-((2H-tetrazol-5-yl)methyl)-N-(1-hydroxy-1H-indazol-5-yl)cyclopropanecarboxamide (Compound 24).

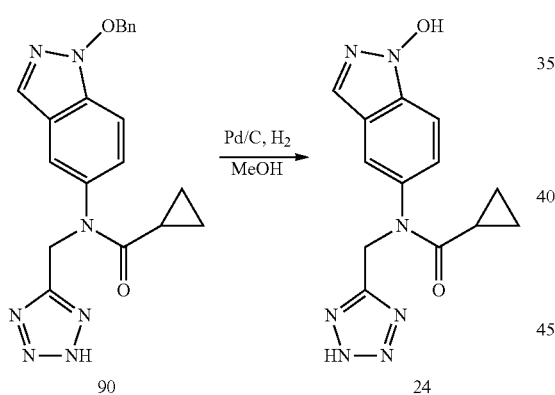

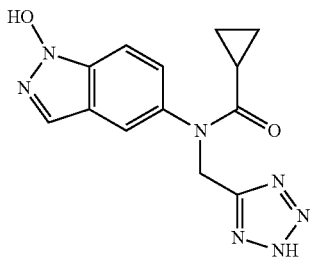

a. Preparation of N-(1-(benzyloxy)-1H-indazol-5-yl)-N-(cyanomethyl)cyclopropanecarboxamide (Compound 89).

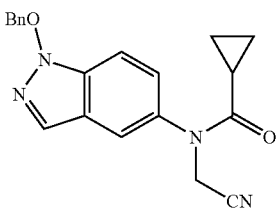 [SMILES: N#CCN(C(=O)C1CC1)c1ccc2c(cnn2OCc2ccccc2)c1]

The procedure used to prepare 89 was the same procedure as that used to prepare 77 except that cyclopropanecarbonyl chloride (104 mg, 1 mmol) was used instead of 3,5-dimethylisoxazole-4-carbonyl chloride, afforded the desired product, 89, (249 mg, 72% yield).

The procedure used to prepare 24 was the same procedure as that used to prepare 18 except that 90 (74 mg, 0.19 mmol) was used instead of 78, afforded the desired product, 24, as a solid (56.8 mg, 100% yield). $^1$H NMR (500 MHz, DMSO) δ 7.83 (s, 1H), 7.76 (s, 1H), 7.54 (d, J=8.8 Hz, 1H), 7.38 (d, J=8.7 Hz, 1H), 5.13 (s, 2H), 1.29 (m, 1H), 0.79 (m, 2H), 0.61 (d, J=3.8 Hz, 2H). MS (ESI, CH$_3$OH): [C$_{13}$H$_{13}$N$_7$O$_2$]m/z 300.4 ([M+H]$^+$).

26. Preparation of N-((2H-tetrazol-5-yl)methyl)-N-(1-hydroxy-1H-indazol-5-yl)propionamide (Compound 25).

The overall synthesis scheme (Synthesis Scheme 25) for the preparation of Compound 25 is shown below. The synthesis proceeds through the intermediates indicated (Compounds 74, 91, and 92). The yield for each synthetic step was as indicated.

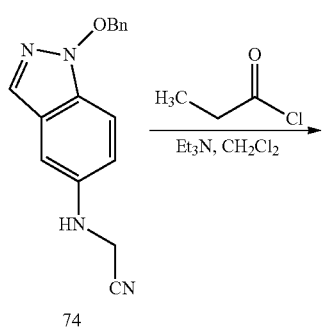

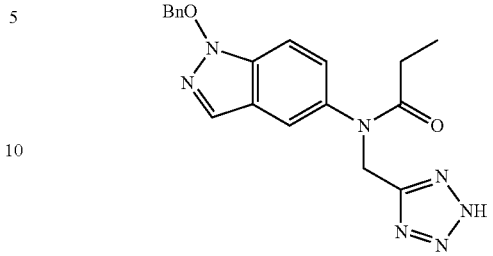

b. Preparation of N-(1-(benzyloxy)-1H-indazol-5-yl)-N-(cyanomethyl)propionamide (Compound 92).

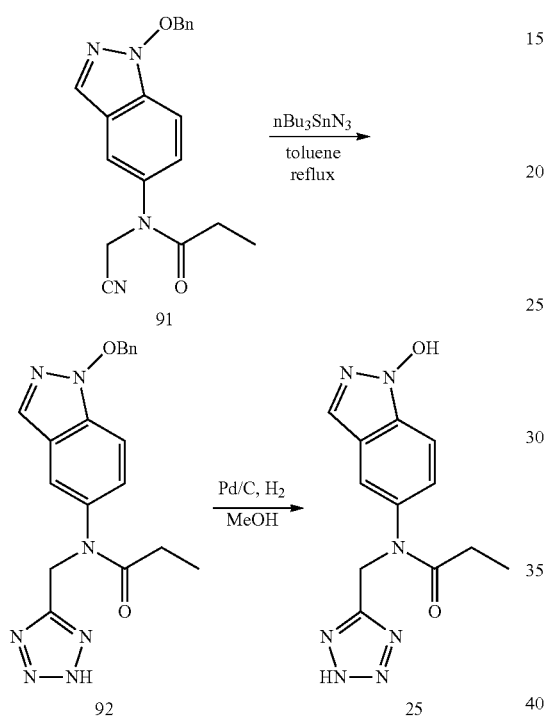

The procedure used to prepare 92 was the same procedure as that used to prepare 33 except that 91 (100.2 mg, 0.30 mmol) was used instead of 32, afforded the desired product, 92, as a solid (94.8 mg, 84% yield). $^1$H NMR (300 MHz, CDCl$_3$) δ 7.79 (s, 1H), 7.47 (s, 1H), 7.33 (d, J=1.2 Hz, 5H), 7.16 (d, J=8.7 Hz, 1H), 7.03 (dd, J=8.8, 1.8 Hz, 1H), 5.33 (d, J=20.2 Hz, 2H), 5.11 (s, 2H), 2.10 (q, J=7.3 Hz, 2H), 1.00 (t, J=7.4 Hz, 2H). $^{13}$C NMR (75 MHz, CDCl$_3$) δ 176.96, 152.84, 135.23, 134.21, 134.01, 130.13, 129.67, 128.94, 128.47, 126.53, 121.44, 120.47, 110.68, 80.82, 43.73, 27.85, 9.68.

c. Preparation of N-((2H-tetrazol-5-yl)methyl)-N-(1-hydroxy-1H-indazol-5-yl)propionamide (Compound 25).

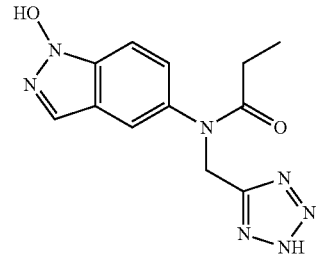

The procedure used to prepare 25 was the same procedure as that used to prepare 18 except that 92 (112.8 mg, 0.30 mmol) was used instead of 78, afforded the desired product, 25, as a solid (83.4 mg, 100% yield). $^1$H NMR (500 MHz, DMSO) δ 7.79 (d, J=3.2 Hz, 1H), 7.69 (s, 1H), 7.51 (s, 1H), 7.32 (s, 1H), 5.08 (d, J=3.3 Hz, 2H), 3.14 (m, 2H), 2.00 (d, J=3.4 Hz, 3H). MS (ESI, CH$_3$OH): [C$_{12}$H$_{13}$N$_7$O$_2$]m/z 288.2 ([M+H]$^+$).

27. Beta-Catenin Protein Expression and Purification

β-Catenin (residues 138-686) was cloned into a pEHISTEV vector carrying a N-terminal 6× histidine (a gift from Dr. Hanting Liu, St. Andrew University, UK) and transformed into *E. Coli* BL21 DE3 (Novagen). Cells were cultured in LB medium with 30 g/mL kanamycin until the OD$_{600}$ was approximately 0.8, and then protein expression was induced with 400 μM of IPTG at 20° C. overnight. Cells were lysed by sonication and the proteins were purified by Ni-NTA affinity chromatography (Qiagen 30210) and dialyzed against a buffer containing 20 mM of HEPES (pH=7.5), 200 mM of NaCl, 10% glycerol, and 5 mM of DTT. Proteins were aliquoted and stored at −80° C.

28. AlphaScreen Assay

Experiments were performed in white opaque 384-well plates from PerkinElmer (Waltham, Mass.), and the samples were read on a Synergy 2 plate reader (Biotek, Winooski, Vt.) with a sensitivity setting of 200 using AlphaScreen a. Preparation of N-(1-(benzyloxy)-1H-indazol-5-yl)-N-(cyanomethyl)propionamide (Compound 91).

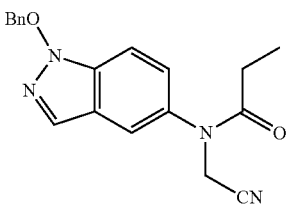 [SMILES: CCC(=O)N(CC#N)c1ccc2c(cnn2OCc2ccccc2)c1]

The procedure used to prepare 91 was the same procedure as that used to prepare 77 except that propionyl chloride (92 mg, 1 mmol) was used instead of 3,5-dimethylisoxazole-4-carbonyl chloride, afforded the desired product, 91, (224 mg, 67% yield). $^1$H NMR (300 MHz, CDCl$_3$) δ 7.81 (d, J=11.8 Hz, 1H), 7.58 (d, J=1.8 Hz, 1H), 7.32 (m, 5H), 7.20 (d, J=8.8 Hz, 1H), 7.07 (dt, J=19.5, 9.8 Hz, 1H), 5.33 (s, 2H), 4.53 (s, 2H), 2.02 (dd, J=14.8, 7.4 Hz, 2H), 1.05 (dd, J=17.1, 9.7 Hz, 3H). $^{13}$C NMR (75 MHz, CDCl3) δ 174.16, 133.99, 133.72, 129.85, 129.38, 128.62, 128.11, 126.35, 121.24, 120.50, 115.55, 110.53, 80.51, 37.17, 27.31, 9.13.

protocol with excitation at 680 nm and emission at 570 nm. All dilutions were made in 1× assay buffer containing 25 mM HEPES (pH 7.4), 100 mMNaCl and 0.1% BSA to minimize nonspecific interactions. For inhibitor competition experiment, 5 nM of C-terminal biotinylated Tcf4 45-mer, 20 nM of N-terminal His$_6$-tagged β-catenin and inhibitors at different concentration were incubated in 20 μL of assay buffer for 2 h. Donor and acceptor beads were added to a final concentration of 10 μg/mL in 25 μL of assay buffer. The mixture was incubated at room temperature for 1 h. For each inhibitor competition assay, the negative controls (equivalent to 0% inhibition) refer to 5.0 nM of biotinylated Tcf4 45-mer, 20 nM of β-catenin, 10 g/mL donor and acceptor beads, but no tested peptide inhibitor was presented. The positive controls (equivalent to 100% inhibition) refer to only 5.0 nM of biotinylated Tcf4 45-mer and 10 g/mL donor and acceptor beads in a final volume of 25 μL. The IC$_{50}$ value was determined by nonlinear least-square analysis of GraphPad Prism 5.0. Experiments were performed in triplicate and carried out in the presence of 1% DMSO.

29. Fluorescence Polarization ("FP") Assay

Experiments were performed in 96-well Microfluor 2 black plates (Waltham, Mass.), and the samples were read by a Synergy 2 plate reader (Biotek, Winooski, Vt.). The fluorescence polarization ("FP") was measured at room temperature with an excitation wavelength at 485 nm and an emission wavelength at 535 nm. The FP saturation experiment was performed in an assay buffer of 137 mM of NaCl, 2.7 mM of KCl, 10 mM of Na$_2$HPO$_4$, 2 mM of KH$_2$PO$_4$, 100 μg/mL of bovine gamma globulin, and 0.01% Triton-X 100. The final reaction volume is 100 μL. The polarization values were expressed in milliploarization units (mP), calculated using the following formula:

$$mP = \frac{1000(I_s - GI_p)}{I_s + GI_p}$$

In the above equation, $I_s$ and $I_p$ are the parallel and perpendicular emission intensity of the sample, respectively. G, the G factor, was determined to be 0.993.

The competitive FP assays used 2.5 nM of Tcf4 fluorescence tracer, 10 nM of β-catenin, and different concentrations of the tested inhibitors in 100 μL of assay buffer. Each assay plate was covered black and gently mixed on an orbital shaker for 3 h to reach equilibrium before polarization values were read. For each inhibitor competition assay, the negative controls (equivalent to 0% inhibition) refer to 2.5 nM of Tcf4 fluorescence tracer and 10 nM of β-catenin, but no tested peptide inhibitor was presented. The positive controls (equivalent to 100% inhibition) refer to only 2.5 nM of Tcf4 fluorescence tracer in a final volume of 100 μL.

The percent (%) inhibition was calculated using the equation:

$$\% \text{ Inhibition} = 100 \times \left[1 - \frac{mP - mP_{free}}{mP_{bound} - mP_{free}}\right]$$

In the foregoing equation, $mP_{free}$ is the signal of the positive control; $mP_{bound}$ is the signal of the negative control; and mP is the signal of the tested inhibitor compound. The IC$_{50}$ values were determined by nonlinear least-square analysis using GraphPad Prism 5.0. Experiments were performed in triplicate and carried out in the presence of 1% DMSO.

30. Competitive Inhibition Assay

A competitive inhibition assay was used to determine inhibitor selectivities for β-catenin/Tcf over β-catenin/E-cadherin and β-catenin/APC-R3 interactions. For the β-catenin/Tcf inhibition assay, 10 nM human β-catenin (residues 138-686) was incubated with 2.5 nM of C-terminally fluorescent-labeled human Tcf4 (residues 7-51) in assay buffer for 30 min at 4° C. Different concentrations of the tested compounds in the assay buffer were added to each test plates to make a final volume of 100 μL. For the β-catenin/E-cadherin inhibition assay, 150 nM human β-catenin (residues 138-686) was incubated with 5 nM of C-terminally fluorescent-labeled human E-cadherin (residues 819-873) in assay buffer for 30 min at 4° C. Different concentrations of the tested compounds in the assay buffer were added to each test plates to make a final volume of 100 μL. For the β-catenin/APC-R3 inhibition assay, 1440 nM human β-catenin (residues 138-686) was incubated with 5 nM of C-terminally fluorescent-labeled human APC-R3 (residues 1477-1519) in assay buffer for 30 min at 4° C. Different concentrations of the tested compounds in the assay buffer were added to each test plates to make a final volume of 100 μL. Each assay plate was covered black and gently mixed on an orbital shaker at 4° C. for 2.5 h to reach equilibrium before the polarization values were read. The IC$_{50}$ values were determined by nonlinear least-square analyses (the variable slope equation, Y=Bottom+(Top−Bottom)/(1+10$^{(Log\ IC50-X) \times Hill\ slope}$)) using GraphPad Prism 5.0. All of the experiments were performed in triplicate. The results were expressed as mean±standard deviation. The Tcf/cahderin selectivity ratios were calculated based on the respective $K_i$ value of β-catenin/E-cadherin interactions over that of β-catenin/Tcf4 interactions. The Tcf/APC selectivity ratios were calculated based on the respective $K_i$ value of β-catenin/APC-R3 interactions over that of β-catenin/Tcf4 interactions.

31. Cell Proliferation Inhibition Assay

HCT116 colon cancer cell line (ATCC CCL-247) was purchased from American Type Culture Collection (ATCC, Manassas, Va.). HEK293 human embryonic kidney cell line was a kind gift from of Dr. Katharine S. Ullman of the Hunstman Cancer Institute at the University of Utah. The cell proliferation agent, 3-(4,5-dimethylthiazol-2-yl)-5-(3-carboxymethoxyphenyl)-2-(4-sulfophenyl)-2H-tetrazolium ("MTS"), was purchased from Promega (Madison, Wis.) and phenazinemethosulfate from Sigma-Aldrich (St. Louis, Mo.). Cultured cell lines were seeded in 96-well plates at 3×10$^3$ cells/well, maintained overnight at 37° C., and incubated in the presence of the tested compounds at various concentrations. Final DMSO concentrations in all assays did not exceed 0.2%. Cell viability and density were monitored after 72 h using a freshly prepared mixture of 1 part of phenazinemethosulfate solution (0.92 mg/mL) and 19 parts of MTS solution (2 mg/mL). Cells were incubated in 10 μL of this solution at 37° C. for 3 h and the UV absorption at 490 nm was measured. Vehicle-treated cells was used as the negative control. The IC$_{50}$ values and the Hill slopes were generated using Graphpad Prism 5.0. All data were expressed as mean±SD.

32. IC$_{50}$ Data for Representative Disclosed Compounds

The inhibitory activities of six known β-catenin/Tcf inhibitors (PKF115-584, CGP049090, PNU-74654, iCRT3, iCRT5, and iCRT14) were determined and compared under the same assay conditions, as shown in Table 2, for representative disclosed compounds (compound numbers 1-25). A comparison of the results obtained with representative disclosed compounds with the known inhibitors suggests that the representative disclosed compounds are more potent. The data in Table 2 are expressed as mean±standard deviation (n=3).

TABLE 2

| Compound | Structure | $K_i$ (μM) FP* | $K_i$ (μM) AlphaScreen |
|---|---|---|---|
| PKF115-584 | 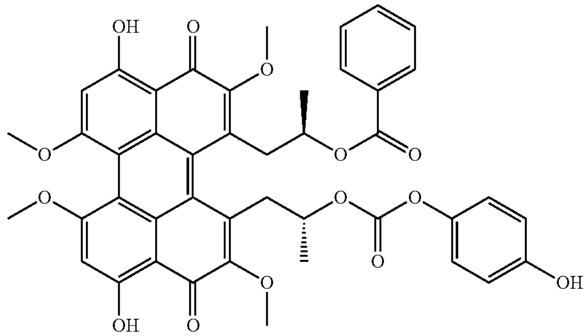 [SMILES: COc1c(C[C@@H](C)OC(=O)Oc2ccc(O)cc2)c2c3c(C[C@@H](C)OC(=O)c4ccccc4)c(OC)c(=O)c4c(O)cc(OC)c(c5c(OC)cc(O)c(c1=O)c52)c43] | 17.78 ± 2.13 | —[a] |
| CGP049090 | 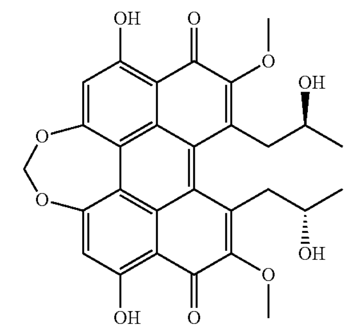 [SMILES: COc1c(C[C@H](C)O)c2c3c(C[C@H](C)O)c(OC)c(=O)c4c(O)cc5c(c6c(cc(O)c(c1=O)c62)OCO5)c43] | 35.56 ± 4.4 | —[a] |
| PKF118-310 | 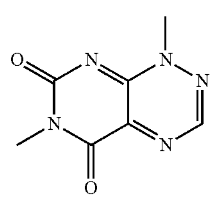 | 5.82 ± 0.24 | 3.65 ± 0.68 |
| PNU-74654 | 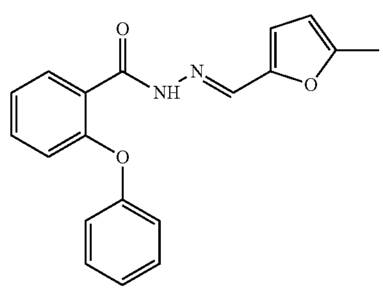 [SMILES: Cc1ccc(/C=N/NC(=O)c2ccccc2Oc2ccccc2)o1] | 180.99 ± 0.68 | 24.39 ± 0.74 |
| iCRT3 | 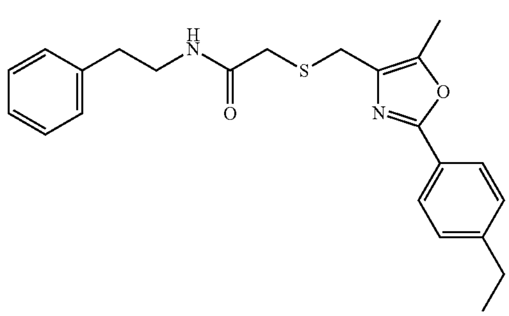 [SMILES: CCc1ccc(-c2nc(CSCC(=O)NCCc3ccccc3)c(C)o2)cc1] | 364.71 ± 6.32 | 195.47 ± 0.87 |

TABLE 2-continued
| Compound | Structure | $K_i$ (μM) FP* | AlphaScreen |
|---|---|---|---|
| iCRT5 | 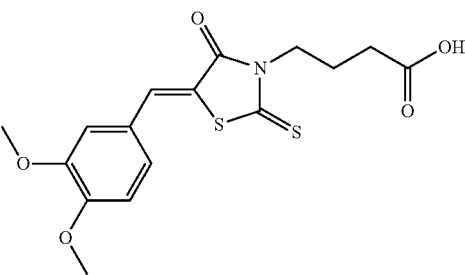 [SMILES: COc1ccc(/C=C2\SC(=S)N(CCCC(=O)O)C2=O)cc1OC] | 80.34 ± 4.17 | 46.81 ± 2.10 |
| iCRT14 | 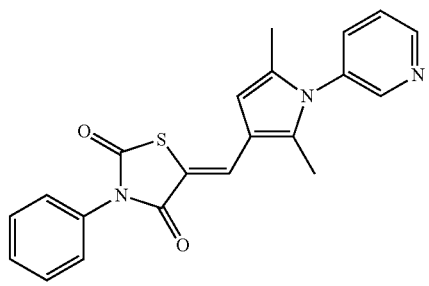 [SMILES: Cc1cc(/C=C2\SC(=O)N(c3ccccc3)C2=O)c(C)n1-c1cccnc1] | 53.51 ± 5.24 | 40.67 ± 1.02 |
| 1 | 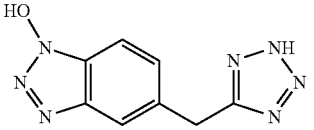 [SMILES: On1nnc2cc(Cc3nn[nH]n3)ccc21] | 1304 ± 2.03 | N.D.[b] |
| 2 | 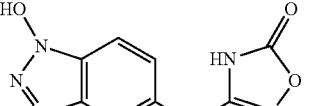 | 165.4 ± 1.45 | N.D.[b] |
| 3 | 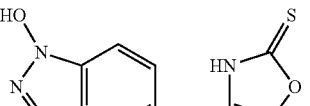 | 105.9 ± 0.18 | N.D.[b] |
| 4 | 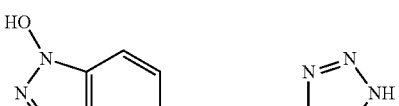 | 155.1 ± 1.17 | N.D.[b] |
| 5 | 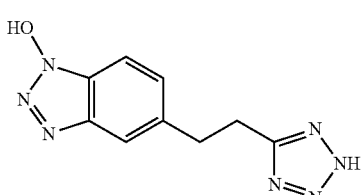 | 54.2 ± 0.36 | N.D.[b] |
| 6 | 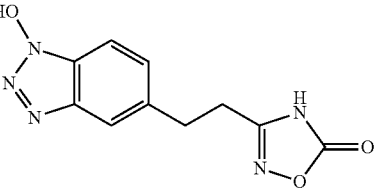 | 551.25 ± 0.897 | N.D.[b] |

TABLE 2-continued

| Compound | Structure | $K_i$ (μM) FP* | AlphaScreen |
|---|---|---|---|
| 7 | 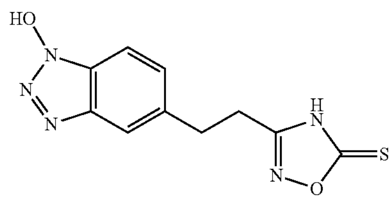 | 24.36 ± 0.63 | N.D.[b] |
| 8 | 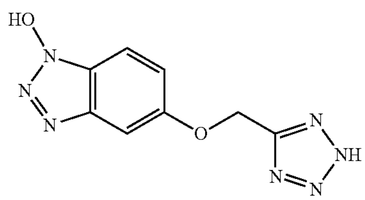 [SMILES: On1nnc2cc(OCc3nn[nH]n3)ccc21] | 50.4 ± 3.11 | N.D.[b] |
| 9 | 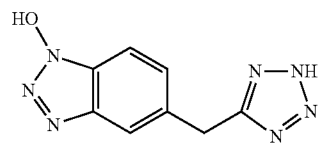 [SMILES: On1nnc2cc(Cc3nn[nH]n3)ccc21] | 94.4 ± 0.76 | N.D.[b] |
| 10 | 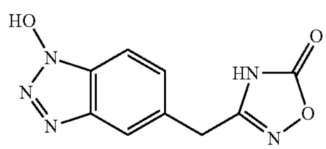 [SMILES: O=c1[nH]c(Cc2ccc3c(c2)nnn3O)no1] | 125.1 ± 1.30 | N.D.[b] |
| 11 | 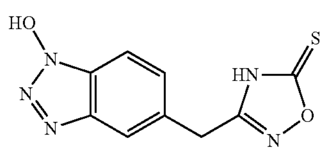 [SMILES: On1nnc2cc(Cc3noc(=S)[nH]3)ccc21] | 22.4 ± 0.97 | 42.02 ± 4.00 |
| 12 | 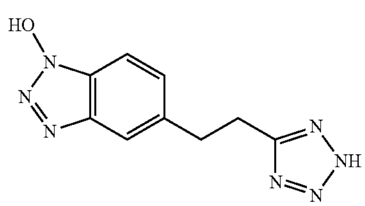 | 3.14 ± 0.48 | 7.60 ± 1.67, 3.83 ± 0.45 |
| 13 | 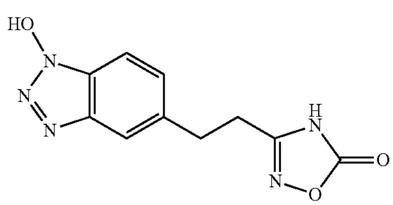 [SMILES: O=c1[nH]c(CCc2ccc3c(c2)nnn3O)no1] | 97.7 ± 0.45 | N.D.[b] |
| 14 | 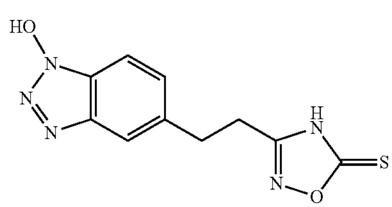 [SMILES: On1nnc2cc(CCc3noc(=S)[nH]3)ccc21] | 7.24 ± 0.13 | 70.37 ± 1.82 |

TABLE 2-continued

| Compound | Structure | K$_i$ (μM) FP* | AlphaScreen |
|---|---|---|---|
| 15 | 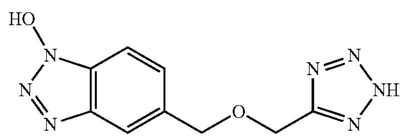 [SMILES: On1nnc2cc(COCc3nn[nH]n3)ccc21] | 13.55 ± 0.19 | N.D.[b] |
| 16 | 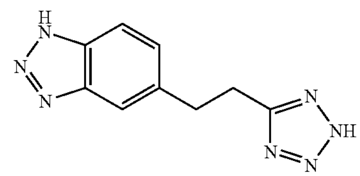 [SMILES: c1cc2[nH]nnc2cc1CCc1nn[nH]n1] | 179.93 ± 2.91 | N.D.[b] |
| 17 | 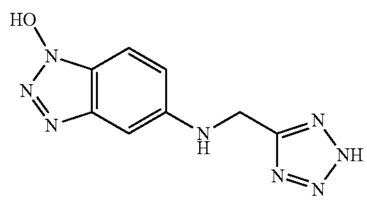 [SMILES: On1nnc2cc(NCc3nn[nH]n3)ccc21] | 3.38 ± 0.61 | N.D.[b] |
| 18 | 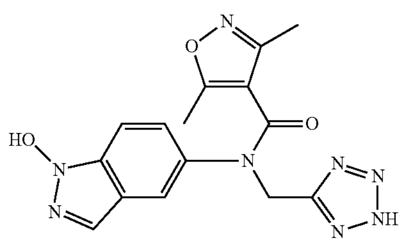 [SMILES: Cc1noc(C)c1C(=O)N(Cc1nn[nH]n1)c1ccc2c(cnn2O)c1] | 16.57 ± 0.73 | N.D.[b] |
| 19 | 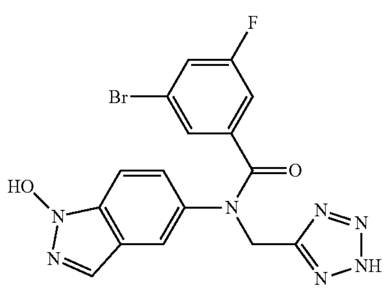 [SMILES: O=C(c1cc(F)cc(Br)c1)N(Cc1nn[nH]n1)c1ccc2c(cnn2O)c1] | 28.74 ± 0.86 | N.D.[b] |
| 20 | 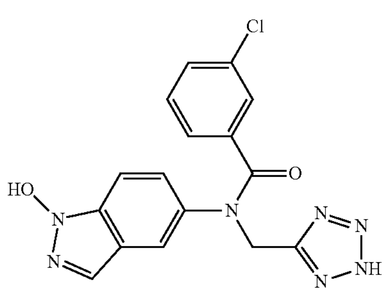 [SMILES: O=C(c1cccc(Cl)c1)N(Cc1nn[nH]n1)c1ccc2c(cnn2O)c1] | 33.14 ± 2.97 | N.D.[b] |

TABLE 2-continued

| Compound | Structure | $K_i$ (μM) | |
| --- | --- | --- | --- |
| | | FP* | AlphaScreen |
| 21 | 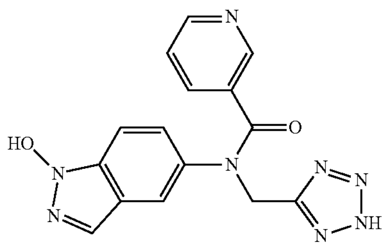 [SMILES: O=C(c1cccnc1)N(Cc1nn[nH]n1)c1ccc2c(cnn2O)c1] | 179.93 ± 2.91 | N.D.[b] |
| 22 | 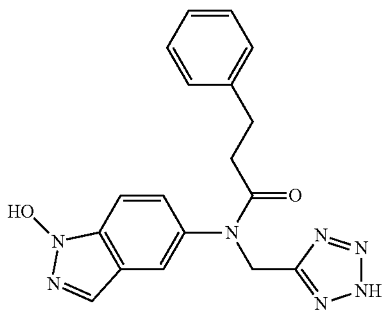 [SMILES: O=C(CCc1ccccc1)N(Cc1nn[nH]n1)c1ccc2c(cnn2O)c1] | N.D.[b] | N.D.[b] |
| 23 | 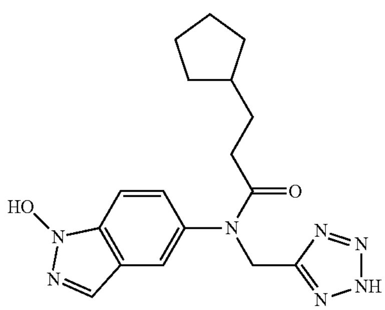 [SMILES: O=C(CCC1CCCC1)N(Cc1nn[nH]n1)c1ccc2c(cnn2O)c1] | N.D.[b] | N.D.[b] |
| 24 | 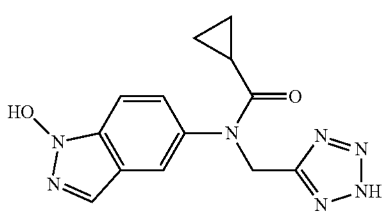 [SMILES: O=C(C1CC1)N(Cc1nn[nH]n1)c1ccc2c(cnn2O)c1] | N.D.[b] | N.D.[b] |
| 25 | 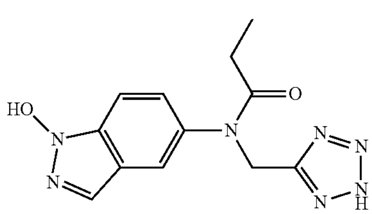 [SMILES: CCC(=O)N(Cc1nn[nH]n1)c1ccc2c(cnn2O)c1] | N.D.[b] | N.D.[b] |

*"FP" means "Fluorescence Polarization Assay."
[a]PKF115-584 and CGPP049090 interfere with the AlphaScreen assay.
[b]"N.D". indicates that assay value is "not determined."

Selectivity data are shown as determined using the Alphascreen assay (Table III) and the fluorescence polarization (FP) assay (Table IV).

The membrane is washed 5 times with PBST and blots were imaged using an Odyssey Infrared Imaging System (LI-COR Biosciences).

TABLE III

| Compounds | $K_i \pm SD$ (µM) | | | Selectivity | |
| --- | --- | --- | --- | --- | --- |
| | β-catenin/Tcf4 | β-catenin/E-cadherin | β-catenin/APC-R3 | Tcf/cadherin | Tcf/APC |
| CGPC049090 | 5.87 ± 0.96 | 11.67 ± 1.48 | 8.31 ± 1.05 | 2.0 | 1.4 |
| PKF118-310 | 3.65 ± 0.68 | 19.94 ± 1.71 | 66.23 ± 3.39 | 5.5 | 18.2 |
| 12 | 3.83 ± 0.45 | 105.35 ± 2.25 | 170.65 ± 7.20 | 27.5 | 44.6 |

TABLE IV

| Compounds | $K_i \pm SD$ (µm) | | | Selectivity | |
| --- | --- | --- | --- | --- | --- |
| | β-catenin/Tcf4 | β-catenin/E-cadherin | β-catenin/APC-R3 | Tcf/cadherin | Tcf/APC |
| PKF115-584 | 17.78 ± 2.13 | 13.04 ± 0.31 | 53.85 ± 0.08 | 0.7 | 3.0 |
| CGP049090 | 35.56 ± 4.43 | 14.39 ± 0.32 | 62.49 ± 0.05 | 0.4 | 1.8 |
| PKF118-310 | 5.82 ± 0.24 | 13.30 ± 0.11 | 171.25 ± 0.13 | 2.3 | 29.4 |
| 12 | 3.14 ± 0.48 | 103.64 ± 0.42 | 176.04 ± 0.12 | 33.0 | 56.0 |

33. Inhibition of Cell Proliferation by Representative Disclosed Compounds

Figure 2:
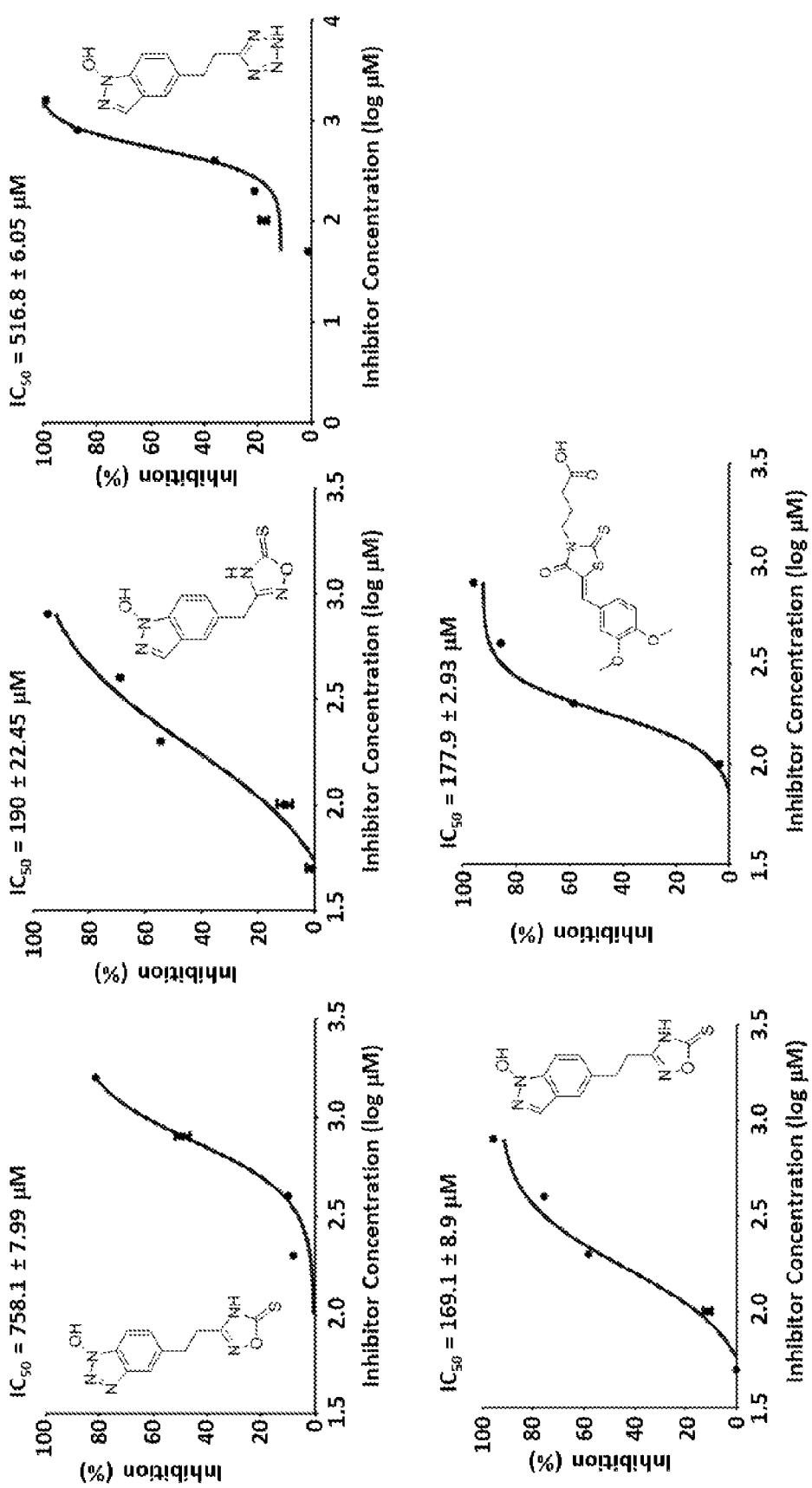
FIG. 2 shows representative data for inhibition of growth of a colon cancer cell line by representative disclosed compounds.

Cell-based assay was performed to assess the ability of compounds 7, 11, 12, and 14 to inhibit the growth of colon cancer cell HCT116 using the MTS-based cell proliferation assay described above. It was found that the four compounds can inhibit the proliferation of colon cancer cell line HCT116 in a dose-dependent as shown in FIG. 2. The potency of 14 is similar to iCRT5 (IC$_{50}$=177.9±2.93 µM) measured in the same assay.

34. Prophetic Western Blot Assay

The following example of an in vitro effect of the disclosed compounds is prophetic. HCT116 cells bear a deletion of codon S45 in β-catenin that makes the protein refractory to phosphorylation and degradation. It results in Wnt targets such as Cylin D1 and c-myc are thus overexpressed. To test the inhibitory effect of compounds on the expression of endogenous Wnt/β-catenin target genes in HCT116 cells, a Western blot assay for Cyclin D1 can be performed. Briefly, HCT116 cells are seeded at 10$^6$ cells/plate, cultured overnight at 37° C., treated with different concentrations of compounds for 24 h and washed by PBS. Cells are lysed in buffer A (150 mM NaCl, 1% NP-40, 50 mM TrisHCl, pH 8.0, 5 mM EDTA, 1 mM PMSF, 5 µM pepstatin, 10 µM Bestatin, and 5 µM E64) for 30 min. Protein concentration was determined by BCA assay. 25 µg protein is resolved by 12% SDS-PAGE. The separated proteins are transferred to a PDVF membrane. After transfer, the membrane is saturated by incubation at 4° C. for 1 h with blocking buffer (LI-COR Biosciences) and then incubated with primary antibody cyclin D1Ab (sc753, Santa Cruz) or β-tubulin Ab (sc55529, Santa Cruz) overnight at 4° C. After washing with PBST, the membrane is incubated with secondary antibody IRDye 800CW goat anti-rabbit IgG (LI-COR Biosciences, cat. #827-08365) for cyclin D1 or IRDye 680LT goat anti-mouse IgG (LI-COR Biosciences, cat. #827-11080) for β-tubulin for 60 min at room temperature.

For example, compounds having a structure represented by a formula:

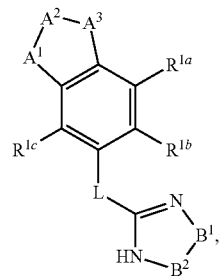

wherein $A^1$ is selected from —N═, —NH—, and —CR$^{2a}$═; wherein $A^2$ is selected from ═N—, (C═O), (C═S), and ═CR$^{2b}$—; wherein $A^3$ is selected from —N(OH)— and —O—; provided that valency is satisfied for $A^1$, $A^2$, and $A^3$; wherein L is selected from —CH$_2$—, —(CH$_2$)$_2$—, —(CH$_2$)$_3$—, —OCH$_2$—, —NHCH$_2$—, —CH$_2$NHCH$_2$—, and —CH$_2$OCH$_2$—; wherein B$^1$ is selected from ═N═, —O—, and —S—; wherein B$^2$ is selected from ═N—, (C═O), and (C═S); provided that valency is satisfied for B$^1$ and B$^2$; wherein each of R$^{1a}$, R$^{1b}$, and R$^{1c}$ is independently selected from hydrogen, halogen, —OH, —NH$_2$, C1-C3 haloalkyl, C1-C3 polyhaloalkyl, and C1-C3 alkoxy; and wherein each of R$^{2a}$ and R$^{2b}$ is independently selected from hydrogen, halogen, —OH, —NH$_2$, C1-C3 haloalkyl, C1-C3 polyhaloalkyl, and C1-C3 alkoxy; or pharmaceutically acceptable salt, ester, hydrate, solvate, or polymorph thereof 35. Prophetic In Vivo Activity in a Tumor Xenograft Model The following example of the in vivo effect of the disclosed compounds is prophetic. Generally agents which inhibit the Wnt pathway, including β-catenin/Tcf protein-protein interaction inhibitors, are expected to display efficacy in preclinical models of cancer. In vivo effects of the compounds described in the preceding examples are expected to be shown in various animal models of cancer known to the skilled person, such as tumor xenograft models. These models are typically conducted in rodent, most often in mouse, but may be conducted in other animal species as is convenient to the study goals. Compounds, products, and compositions disclosed herein are expected to show in vivo effects in various animal models of cancer known to the skilled person, such as mouse tumor xenograft models.

In vivo effects of compounds can be assessed with in a mouse tumor xenograft study, one possible study protocol is described herein. Briefly, cells (2 to 5×10⁶ in 100 µl culture media) were implanted subcutaneously in the right hind flank athymic nu/nu nude mice (5 to 6 weeks old, 18-22 g). For test compounds of the present invention, a typical cell-line used for the tumor xenograft study can be HCT116 cells (a colon cancer cell line; ATCC CCL-247, ATCC, Manassas, Va.). Other suitable cell-lines for these studies are breast or prostate cancer cell lines available from ATCC. The cells are cultured prior to harvesting for this protocol as described herein.

Following implantation, the tumors are allowed to grow to 100 mm³ before the animals are randomized into treatment groups (e.g. vehicle, positive control and various dose levels of the test compound; the number of animals per group is typically 8-12. Day 1 of study corresponds to the day that the animals receive their first dose. The efficacy of a test compound can be determined in studies of various length dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis.

For example, compounds having a structure represented by a formula:

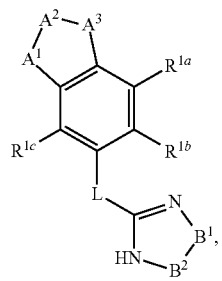

wherein A¹ is selected from —N═, —NH—, and —CR²ᵃ═; wherein A² is selected from ═N—, (C═O), (C═S), and ═CR²ᵇ—; wherein A³ is selected from —N(OH)— and —O—; provided that valency is satisfied for A¹, A², and A³; wherein L is selected from —CH₂—, —(CH₂)₂—, —(CH₂)₃—, —OCH₂—, —NHCH₂—, —CH₂NHCH₂—, and —CH₂OCH₂—; wherein B¹ is selected from —N═, —O—, and —S—; wherein B² is selected from ═N—, (C═O), and (C═S); provided that valency is satisfied for B¹ and B²; wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy; or pharmaceutically acceptable salt, ester, hydrate, solvate, or polymorph thereof.

36. Prophetic Pharmaceutical Composition Examples

"Active ingredient" as used herein throughout these examples relates to one or more disclosed compounds, or a product of a disclosed method of making, or a pharmaceutically acceptable salt, solvate, polymorph, hydrate and the stereochemically isomeric form thereof. The following examples of the formulation of the compounds of the present invention in tablets, suspension, injectables and ointments are prophetic.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention.

Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press). The disclosure of this reference is hereby incorporated herein by reference.

a. Pharmaceutical Composition for Oral Administration

A tablet can be prepared as follows:

| Component | Amount |
| --- | --- |
| Active ingredient | 10 to 500 mg |
| Lactose | 100 mg |
| Crystalline cellulose | 60 mg |
| Magnesium stearate | 5 mg |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
| --- | --- |
| Active ingredient | 10 to 500 mg |
| Sodium carbonate | 560 mg* |
| Sodium hydroxide | 80 mg* |
| Distilled, sterile water | Quantity sufficient to prepare total volumen indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 m) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this Example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

[chemical structure]

wherein $A^1$ is selected from —N═, —NH—, and —$CR^{2a}$═;

wherein $A^2$ is selected from ═N—, (C═O), (C═S), and ═$CR^{2b}$—;

wherein $A^3$ is selected from —N(OH)— and —O—; provided that valency is satisfied for $A^1$, $A^2$, and $A^3$;

wherein $B^1$ is selected from —N═, —O—, and —S—;

wherein $B^2$ is selected from ═N—, (C═O), (C═S), and (S═O);

provided that valency is satisfied for $B^1$ and $B^2$;

wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy;

wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$;

wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy;

wherein $Ar^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein $Cy^1$ is C3-C6 cycloalkyl or C2-C5 heterocycloalkyl substituted with 0-3 substituents independently selected from halogen, —OH, —NH$_2$, C1-C3 haloalkyl, C1-C3 polyhaloalkyl, and C1-C3 alkoxy;

or pharmaceutically acceptable salt thereof.

2. A method for the treatment of a mammal having a disorder of uncontrolled cellular proliferation associated with a Wnt signaling pathway dysregulation comprising the step of administering to the mammal an effective amount of at least one compound having a structure represented by a formula:

[chemical structure]

wherein A¹ is selected from —N=, —NH—, and —CR²ᵃ=;

wherein A² is selected from =N—, (C=O), (C=S), and =CR²ᵇ—;

wherein A³ is selected from —N(OH)— and —O—;

provided that valency is satisfied for A¹, A², and A³;

wherein L is selected from —CH₂—, —(CH₂)₂—, —(CH₂)₃—, —OCH₂—, —NHCH₂—, —CH₂NHCH₂—, and —CH₂OCH₂—;

wherein B¹ is selected from —N=, —O—, and —S—; wherein B² is selected from =N—, (C=O), and (C=S);

provided that valency is satisfied for B¹ and B²;

wherein each of R¹ᵃ, R¹ᵇ, and R¹ᶜ is independently selected from hydrogen, halogen, —OH, —NH₂, C1-C3 haloalkyl, C1-C3 polyhaloalkyl, and C1-C3 alkoxy; and wherein each of R²ᵃ and R²ᵇ is independently selected from hydrogen, halogen, —OH, —NH₂, C1-C3 haloalkyl, C1-C3 polyhaloalkyl, and C1-C3 alkoxy;

or pharmaceutically acceptable salt thereof.

3. The method of claim 2, wherein the mammal has been diagnosed with a need for treatment of a disorder prior to the administering step.

4. The method of claim 2, further comprising the step of identifying a mammal in need of treatment of the disorder.

5. The method of claim 2, wherein the disorder of uncontrolled cellular proliferation is a cancer.

6. The method of claim 5, wherein the cancer is selected from a colorectal cancer, breast cancer, prostate cancer, hepatic carcinoma, a melanoma, and lung cancer.

7. The method of claim 2, wherein the disorder is characterized by fibrosis.

8. The method of claim 7, wherein the fibrotic disorder is selected from pulmonary fibrosis, liver fibrosis, and polycystic kidney disease.

9. The compound of claim 1, wherein the compound has a structure represented by a formula:

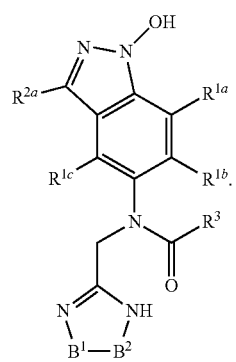

10. The compound of claim 1, wherein the compound has a structure represented by a formula:

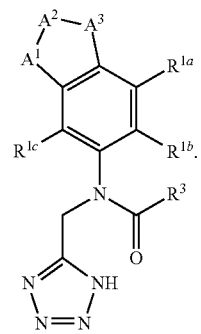

11. The compound of claim 1, wherein the compound is selected from:

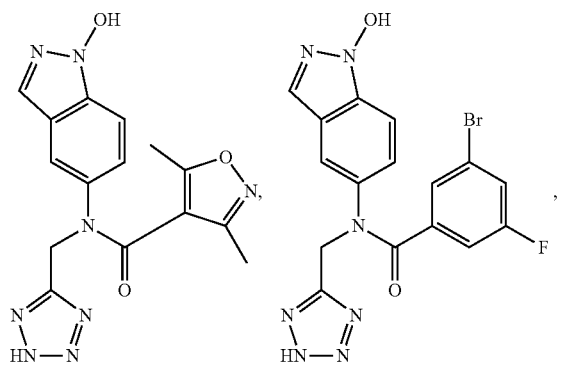

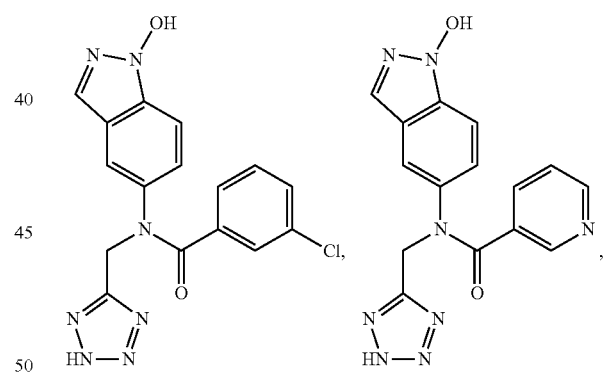

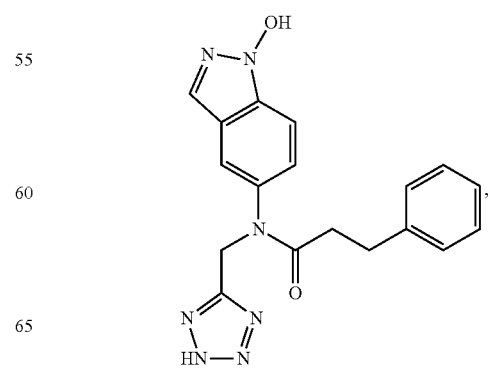

-continued
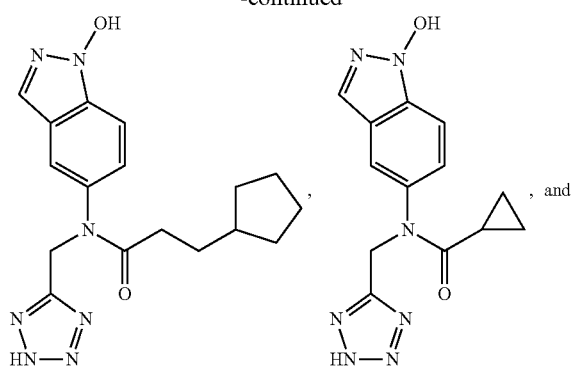
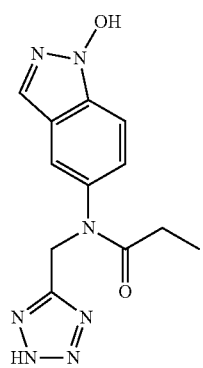
12. The method of claim 2, wherein the compound is selected from:
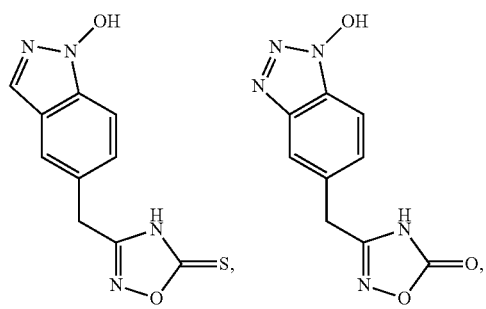
-continued
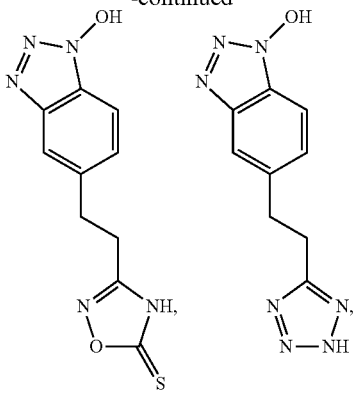
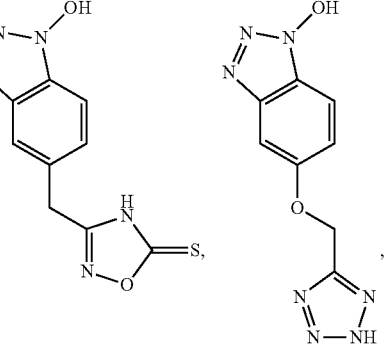
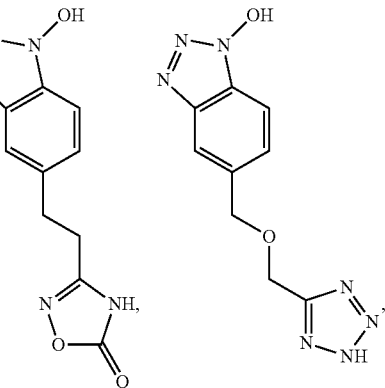
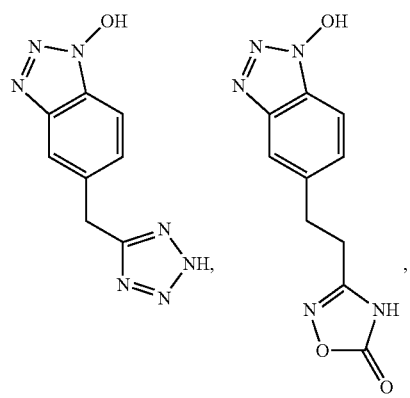
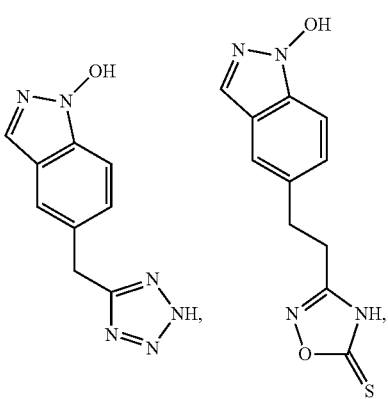

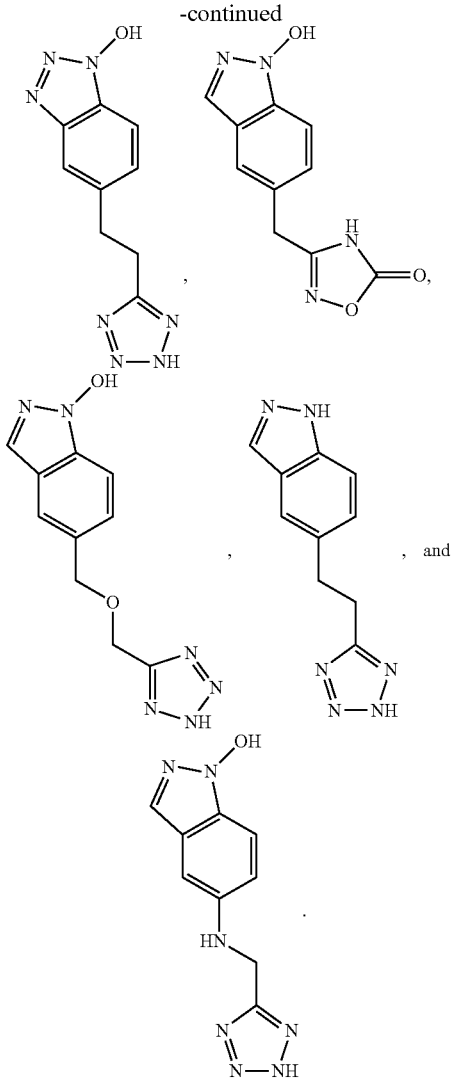

, and

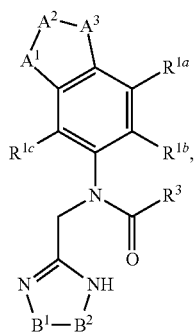

13. A method for the treatment of a mammal having a disorder of uncontrolled cellular proliferation associated with β-catenin/Tcf protein-protein interaction dysfunction or associated with a Wnt signaling pathway dysregulation, the method comprising the step of administering to the mammal an effective amount of at least one compound having a structure represented by a formula:

wherein $A^1$ is selected from —N═, —NH—, and —$CR^{2a}$═;

wherein $A^2$ is selected from ═N—, (C═O), (C═S), and ═$CR^{2b}$—;

wherein $A^3$ is selected from —N(OH)— and —O—;
provided that valency is satisfied for $A^1$, $A^2$, and $A^3$;

wherein $B^1$ is selected from —N═, —O—, and —S—;
wherein $B^2$ is selected from ═N—, (C═O), (C═S), and (S═O);
provided that valency is satisfied for $B^1$ and $B^2$;

wherein each of $R^{1a}$, $R^{1b}$, and $R^{1c}$ is independently selected from hydrogen, halogen, —OH, —NH$_2$, C1-C3 haloalkyl, C1-C3 polyhaloalkyl, and C1-C3 alkoxy; and wherein each of $R^{2a}$ and $R^{2b}$ is independently selected from hydrogen, halogen, —OH, —NH$_2$, C1-C3 haloalkyl, C1-C3 polyhaloalkyl, and C1-C3 alkoxy;

wherein $R^3$ is selected from C1-C6 alkyl, C1-C6 monohaloalkyl, C1-C6 polyhaloalkyl, $Ar^1$, $Ar^2$, $Cy^1$, —(C1-C6)-$Ar^1$, —(C1-C6)-$Ar^2$, and —(C1-C6)-$Cy^1$;

wherein $Ar^1$ is phenyl substituted with 0-3 substituents independently selected from halogen, —OH, —NH$_2$, C1-C3 haloalkyl, C1-C3 polyhaloalkyl, and C1-C3 alkoxy;

wherein $Ar^2$ is monocyclic heteroaryl substituted with 0-3 substituents independently selected from halogen, —OH, —NH$_2$, C1-C3 haloalkyl, C1-C3 polyhaloalkyl, and C1-C3 alkoxy; and wherein $Cy^1$ is C3-C6 cycloalkyl or C2-5 heterocycloalkyl substituted with 0-3 substituents independently selected from halogen, —OH, —NH$_2$, C1-C3 haloalkyl, C1-C3 polyhaloalkyl, and C1-C3 alkoxy;

or pharmaceutically acceptable salt thereof.

14. The method of claim 13, wherein the mammal has been diagnosed with a need for treatment of a disorder prior to the administering step.

15. The method of claim 13, further comprising the step of identifying a mammal in need of treatment of the disorder.

16. The method of claim 13, wherein the disorder of uncontrolled cellular proliferation is a cancer.

17. The method of claim 13, wherein the cancer is selected from a colorectal cancer, breast cancer, prostate cancer, hepatic carcinoma, a melanoma, and lung cancer.

18. The method of claim 13, wherein the disorder is characterized by fibrosis.

19. The method of claim 13, wherein the fibrotic disorder is selected from pulmonary fibrosis, liver fibrosis, and polycystic kidney disease.

20. The method of claim 13, wherein the compound is selected from:

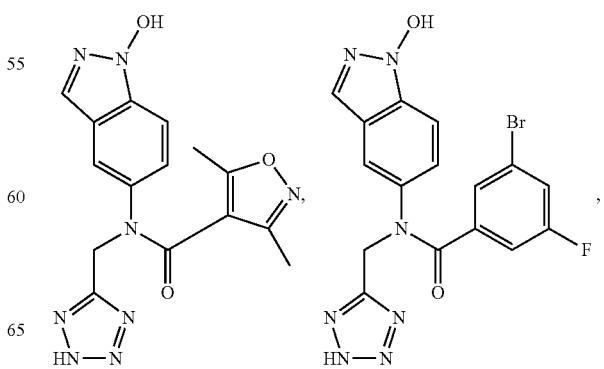

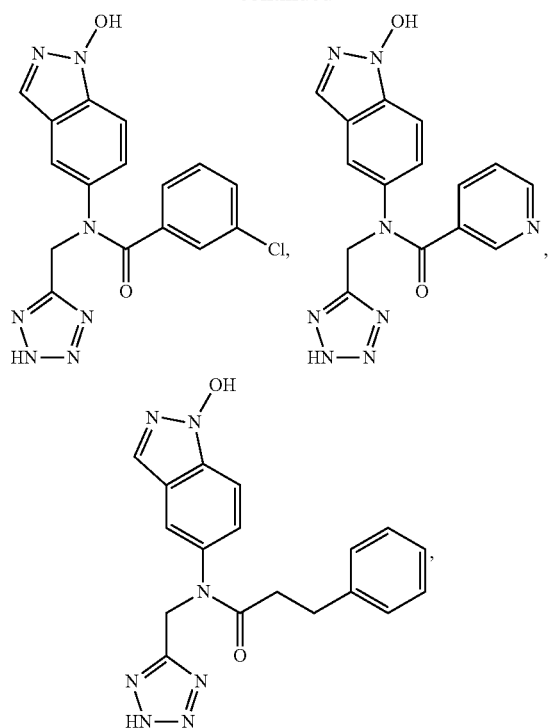
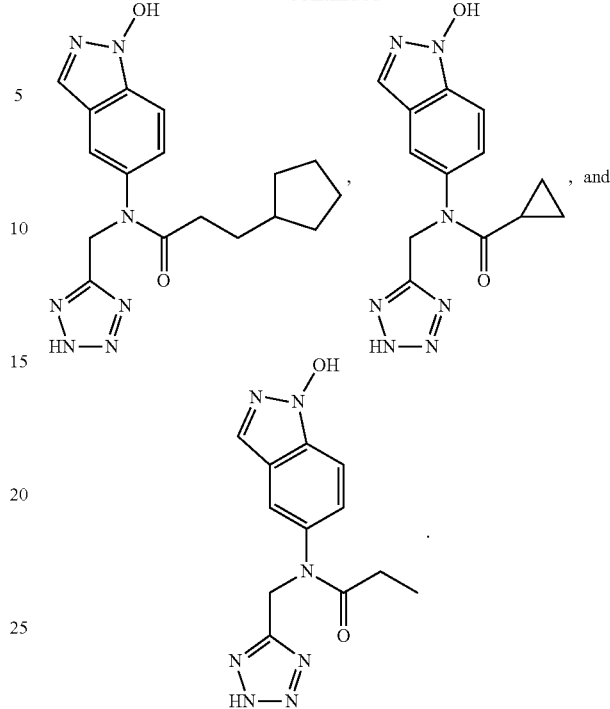
* * * * *